United States Patent
Kapoor et al.

(10) Patent No.: US 11,192,893 B2
(45) Date of Patent: Dec. 7, 2021

(54) PYRAZOLOQUINAZOLINONE ANTITUMOR AGENTS

(71) Applicant: The Rockefeller University, New York, NY (US)

(72) Inventors: Tarun M. Kapoor, New York, NY (US); Moriteru Asano, Tokushima (JP); Kazuyoshi Aso, Kanagawa (JP); Michael A. Foley, New York, NY (US); Yoshiyuki Fukase, Edgewater, NJ (US); Hideki Furukawa, Chigasaki (JP); Yashuhiro Hirata, Kanagawa (JP); Sachie Takashima, Kanagawa (JP); Tomohiro Okawa, Kanagawa (JP); Yuta Tanaka, Kanagawa (JP); Yayoi Yoshitomi, Kanagawa (JP)

(73) Assignee: The Rockefeller University, New York, NY (US)

( * ) Notice: Subject to any disclaimer, the term of this patent is extended or adjusted under 35 U.S.C. 154(b) by 17 days.

(21) Appl. No.: 16/614,621

(22) PCT Filed: May 18, 2018

(86) PCT No.: PCT/US2018/033402
§ 371 (c)(1),
(2) Date: Nov. 18, 2019

(87) PCT Pub. No.: WO2018/213712
PCT Pub. Date: Nov. 22, 2018

(65) Prior Publication Data
US 2020/0148687 A1 May 14, 2020

Related U.S. Application Data

(60) Provisional application No. 62/507,857, filed on May 18, 2017.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC ................. C07D 487/04; A61P 35/00
See application file for complete search history.

(56) References Cited

U.S. PATENT DOCUMENTS

| | | |
|---|---|---|
| 4,247,555 A | 1/1981 | Sircar et al. |
| 4,261,997 A | 4/1981 | Sircar et al. |

(Continued)

FOREIGN PATENT DOCUMENTS

| | | |
|---|---|---|
| CN | 104987747 B | 3/2017 |
| EP | 2666775 A1 | 11/2013 |

(Continued)

OTHER PUBLICATIONS

Al-Etaibi, et al., Stereoselective synthesis of dihydrothiadiazinoazines and dihydrothiadiazinoazoles and their pyrolytic desulfurization ring contraction, Tetrahedron, 67(34), 6259-6274 (2011). (Year: 2011).*

(Continued)

*Primary Examiner* — Erich A Leeser
(74) *Attorney, Agent, or Firm* — Heslin Rothenberg Farley & Mesiti P.C.

(57) ABSTRACT

Compounds of formula:

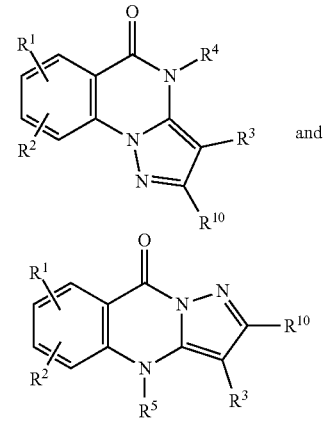

are useful as antitumor agents. In these compounds, $R^{10}$ is (a) $(C_1-C_{10})$ hydrocarbyl, $(C_1-C_{10})$halohydrocarbyl, $(C_1-C_6)$ hydroxyalkyl, or

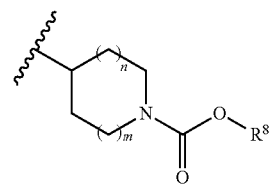

or $R^{10}$ is (b)

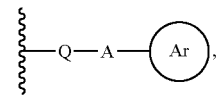

in which Q and A are linkers and Ar is optionally substituted monocyclic or bicyclic aryl or heteroaryl.

20 Claims, No Drawings

(56) References Cited

U.S. PATENT DOCUMENTS

| | | | |
|---|---|---|---|
| 2015/0105381 A1 | 4/2015 | Mayer et al. | |
| 2016/0272646 A1* | 9/2016 | Sturino | ............... C07D 401/06 |

FOREIGN PATENT DOCUMENTS

| | | | |
|---|---|---|---|
| WO | 2007144669 A1 | 12/2007 | |
| WO | 2007149907 A2 | 12/2007 | |
| WO | 2008090379 A1 | 7/2008 | |
| WO | WO 2009/119412 * | 1/2009 | ............ C09B 29/46 |
| WO | 2012099916 A1 | 7/2012 | |
| WO | 2016046404 A1 | 3/2016 | |

OTHER PUBLICATIONS

Zhou et al. "Iodine-catalyzed synthesis of 2-arylpyrazolo[5,1-b]quinazolin-9(3H)—one derivatives in ionic liquids via domino reaction" Tedrahedron, vol. 70, pp. 3440-3446. 2014.

Sircar et al. "Pyrazolo[5,1-b]quinazolin-9-ones: A New Series of Antiallergic Agents", J. Med. Chem, vol. 24, pp. 735-742. 1981.

Ibrahim et al. "Pyrolytic desulfurization ring contraction of condensed thiadiazines as a general route towards pyrazoloazines and pyrazoloazoles with a bridgehead (ring junction) nitrogen atom", Tetrahedron, vol. 64, p. 10365-10374. 2008.

Extended European Search Report in European Application No. 18802058.0, dated Oct. 19, 2020.

Taliani et al. "Phenylpyrazolo[1,5-a]quinazolin-5(4H)—one: A Suitable Scffold for the Development of Noncamptothecin Topoisomerase I (Top1) Inhibitors" Journal of Medicinal Chemistry, vol. 56, pp. 7458-7462. 2013.

Abdel-Wahab et al. "Production of Pyrans, Pyridazines, Pyrimidines, Pyrazines and Triazine Compounds Using Benzoylacetonitriles as a Precursor" J. Iran Chem Coc. pp. 1-19. Apr. 4, 2013.

Pubchem SID 50130134, pp. 1-5. Aug. 18, 2008.

International Search Report in International Application No. PCT/US18/33402, dated Sep. 19, 2018.

Written Opinion in International Application No. PCT/US18/33402, dated Sep. 19, 2018.

* cited by examiner

PYRAZOLOQUINAZOLINONE ANTITUMOR AGENTS

CROSS REFERENCE TO RELATED APPLICATIONS

This application is a 371 National Phase of International Application No. PCT/US2018/033402 filed May 18, 2018 which claims priority from U.S. provisional application 62/507,857, filed May 18, 2017, which is incorporated herein by reference in its entirety.

FEDERALLY SPONSORED RESEARCH

The following invention was made with government support under contracts numbers R01_CA009673-37, R01_GM71772 and R01_GM65933 awarded by the National Cancer Institute and the National Institutes of Health. The Government has certain rights in this invention.

FIELD OF THE INVENTION

The invention relates to 2-substituted-pyrazolo[5,1-b]quinazolin-9(4H)-ones and 2-substituted-pyrazolo[1,5-a]quinazolin-5(4H)-ones that are selective inhibitors of members of the family of AAA+ ATPases. The compounds are useful as anticancer agents and as probes of the function of dynein-dependent systems.

BACKGROUND OF THE INVENTION

The AAA+(ATPases associated with diverse cellular activities) superfamily of enzymes couples ATP hydrolysis with the generation of mechanical force to regulate diverse aspects of prokaryote and eukaryote biology. These complex proteins typically form ring-shaped hexamers with a central pore, and ATP-dependent conformational changes that propagate through these molecular machines can promote DNA replication, the disassembly of membrane-fusing complexes during organelle biogenesis and vesicular transport, the trafficking of cellular cargos along microtubules, and the unfolding of proteins for proteolysis. One of the subclasses of AAA+ ATPases includes dynein 1 and dynein 2. Cytoplasmic dynein 1 acts in concert with dynactin and the nuclear protein NuMA to crosslink and focus the minus ends of microtubules within the mitotic spindle. These actions create the canonical fusiform shape and localize γ-tubulin-containing, microtubule-nucleating complexes to the spindle poles. Cytoplasmic dynein 1 inhibition, by blocking antibodies or dominant negative constructs, disrupts mitotic spindle assembly, resulting in splayed microtubule ends and reduced γ-tubulin recruitment. Dynein 2 is integral in protein trafficking mechanisms within the primary cilium, where it is involved in moving macromolecules along the axoneme. Intraflagellar retrograde trafficking, utilizes cytoplasmic dynein 2 and the IFTA complex. Dynein 2 is required for assembly and length regulation of the primary cilium and loss of its function blocks Hedgehog signaling. Selective small molecule inhibitors of dyneins are therefore useful both as probes of dynein function and as potential antitumor agents.

SUMMARY OF THE INVENTION

In one aspect, the invention relates to pyrazolo[5,1-b]quinazolin-9(4H)-ones of formula I and pyrazolo[1,5-a]quinazolin-5(4H)-ones of formula II:

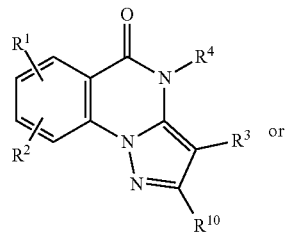

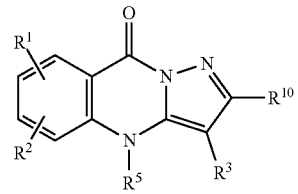

wherein
$R^1$ and $R^2$ are independently chosen from hydrogen, halogen, $(C_1-C_{10})$hydrocarbon, $-O-(C_1-C_{10})$hydrocarbyl, fluoro$(C_1-C_6)$alkyl, $-O(C_1-C_6)$fluoroalkyl, $-CN$, and nitro;
$R^3$ is chosen from hydrogen, cyano, $(C_1-C_6)$alkoxycarbonyl, aminocarbonyl, carboxy, $(C_1-C_6)$alkylaminocarbonyl, $(C_1-C_6)$dialkylaminocarbonyl, halo, amino$(C_1-C_6)$alkyl, $(C_1-C_6)$alkylamino$(C_1-C_6)$alkyl, $(C_1-C_6)$dialkylamino$(C_1-C_6)$alkyl, and nitro;
$R^4$ and $R^5$ are chosen from hydrogen and methyl;
$R^{10}$ is:
  (a)

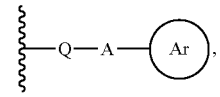

in which
  Ar is chosen from optionally substituted aryl, optionally substituted heteroaryl, said aryl or heteroaryl optionally substituted with one, two or three substituents chosen independently from, halogen, $(C_1-C_{10})$hydrocarbon, $-O-(C_1-C_6)$alkyl, fluoro$(C_1-C_6)$alkyl, $-O-(C_1-C_6)$fluoroalkyl, hydroxy, methylenedioxy, ethylenedioxy, $-CN$, nitro, $-S-(C_1-C_6)$alkyl, $(C_1-C_6)$alkoxycarbonyl, $(C_1-C_6)$acyl, amino, $(C_1-C_6)$alkylamino, di$(C_1-C_6)$alkylamino, $(C_1-C_6)$acylamino, and

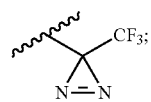

Q is a direct bond or a linker chosen from $-O-$, $-(C_1-C_{10})$hydrocarbyl-, $-(C_1-C_{10})$oxaalkyl, fluoro$(C_1-C_{10})$alkyl, $-O-(C_1-C_6)$fluoroalkyl,

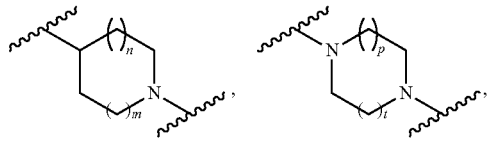

-continued

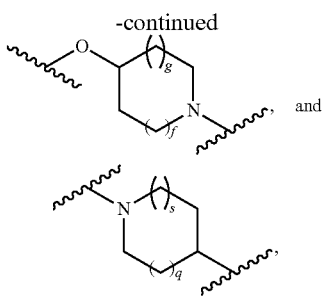
and

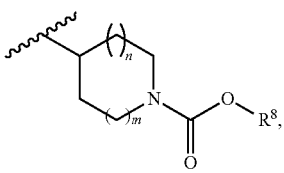

wherein the left wavy line indicates the point of attachment to the pyrazole ring and the right wavy line indicates the point of attachment to A;

A is a direct bond or a linker chosen from: —$CR^6R^7$— and —C(=O)—; and $R^6$ and $R^7$ are independently selected from methyl and hydrogen;

or (b) $R^{10}$ is chosen from ($C_1$-$C_{10}$) hydrocarbyl, ($C_1$-$C_{10}$) halohydrocarbyl, ($C_1$-$C_6$)hydroxyalkl, and

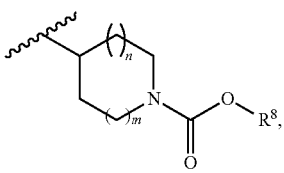

wherein the left wavy line indicates the point of attachment to the pyrazole ring and $R^8$ is ($C_1$-$C_{10}$)hydrocarbyl;

n is 0 or 1;
m is 0, 1, or 2;
p is 0 or 1;
t is 0, 1, or 2;
g is 0 or 1;
f is 0, 1, or 2;
s is 0 or 1; and
q is 0, 1, or 2.

In another aspect, the invention relates to a method of inhibiting the growth of a solid tumor comprising bringing said solid tumor into contact with a compound of formula I or II.

In another aspect, the invention relates to method of inhibiting intraflagellar transport in a cell comprising bringing said cell into contact with a compound of formula I or II.

In another aspect, the invention relates to method of blocking hedgehog signaling in a cell comprising bringing said cell into contact with a compound of formula I or II.

DETAILED DESCRIPTION OF THE INVENTION

Antitumor compounds of the invention fall into two primary subgenera: pyrazolo[5,1-b]quinazolin-9(4H)-ones of formula I and pyrazolo[1,5-a]quinazolin-5(4H)-ones of formula II. Both are inhibitors of hedgehog signaling. The inhibition of hedgehog signaling has been shown to be effective in vivo in treating solid tumors, particularly basal cell carcinoma, glioblastoma and medulloblastoma. For example, Rudin et al. [*N. Engl. J. Med* 361, 1173-1178 (2009)] demonstrated that administration to a human patient of GDC-0449, a small molecule inhibitor of the hedgehog pathway, resulted in regression of medulloblastoma. Similarly, Von Hoff et al. [*N. Engl. J. Med* 361, 1164-1172 (2009)] administered GDC-0449 to 33 human patients with basal cell carcinoma and observed clinically significant response.

In one embodiment, the invention relates to pyrazolo[5,1-b]quinazolin-9(4H)-ones of formula I:

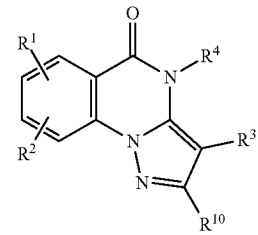

In a second embodiment, the invention relates to pyrazolo[1,5-a]quinazolin-5(4H)-ones of formula II

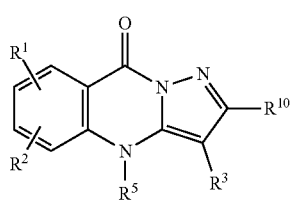

In both genera, $R^1$ and $R^2$ are independently chosen from hydrogen, halogen, ($C_1$-$C_{10}$)hydrocarbon, —O—($C_1$-$C_{10}$)hydrocarbyl, fluoro($C_1$-$C_6$)alkyl, —O($C_1$-$C_6$)fluoroalkyl, —CN, and nitro. In some embodiments, $R^2$ is H or halogen and $R^1$ is chosen from H, halogen, trifluoromethyl, —CN, ($C_1$-$C_{10}$)carboxy, ethynyl, trifluoromethoxy and ($C_1$-$C_3$)alkyl. In some embodiments, $R^2$ is H and $R^1$ is H, halogen, methoxy or trifluoromethyl.

In both genera, $R^3$ is chosen from hydrogen, cyano, ($C_1$-$C_6$)alkoxycarbonyl, aminocarbonyl, carboxy, ($C_1$-$C_6$)alkylaminocarbonyl, ($C_1$-$C_6$)dialkylaminocarbonyl, halo, amino($C_1$-$C_6$)alkyl, ($C_1$-$C_6$)alkylamino($C_1$-$C_6$)alkyl, ($C_1$-$C_6$)dialkylamino($C_1$-$C_6$)alkyl, and nitro; preferably, $R^3$ is H, aminocarbonyl, or CN.

In both genera, $R^4$ and $R^5$ are chosen from hydrogen and methyl, preferably hydrogen.

With respect to compounds in which $R^{10}$ is

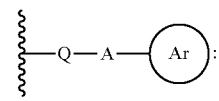

In one set of embodiments:

Ar is chosen from optionally substituted aryl, optionally substituted heteroaryl, said aryl or heteroaryl optionally substituted with one, two or three substituents chosen independently from: halogen, ($C_1$-$C_{10}$)hydrocarbon, —O—($C_1$-$C_6$)alkyl, fluoro($C_1$-$C_6$)alkyl, —O—($C_1$-$C_6$)fluoroalkyl, hydroxy, methylenedioxy, ethylenedioxy, —CN, nitro, —S—($C_1$-$C_6$)alkyl, ($C_1$-$C_6$)alkoxycarbonyl, $(C_1-C_6)$acyl, amino, $(C_1-C_6)$alkylamino, di$(C_1-C_6)$alkylamino, $(C_1-C_6)$acylamino, and

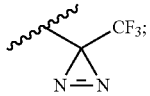

In some embodiments, Ar is chosen from phenyl, thiophenyl, pyrimidine, pyrrolyl, and pyridinyl, any of which may be optionally substituted with from one to three substituents independently chosen from halogen, $(C_1-C_6)$hydrocarbon, fluoro$(C_1-C_6)$alkyl, —O—$(C_1-C_6)$fluoroalkyl, $(C_1-C_6)$ alkoxycarbonyl and $(C_1-C_6)$acyl. In some embodiments, Ar is phenyl substituted with from one to three substituents chosen from halogen and fluoro$(C_1-C_3)$alkyl.

Q is a direct bond or a linker chosen from —O—, —$(C_1-C_{10})$hydrocarbyl-, —$(C_1-C_{10})$oxaalkyl, fluoro $(C_1-C_{10})$alkyl, —O—$(C_1-C_6)$fluoroalkyl,

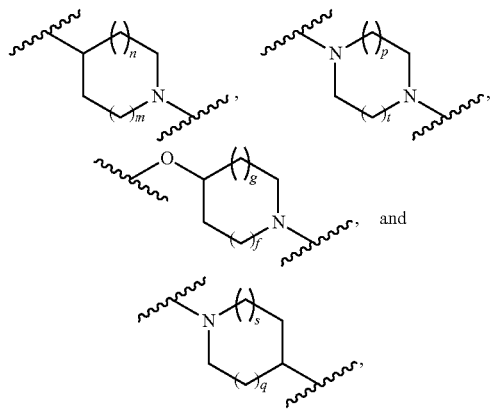

and wherein the left wavy line indicates the point of attachment to the pyrazole ring and the right wavy line indicates the point of attachment to A. In some embodiments when A is a direct bond, Q is a direct bond or $(C_3-C_6)$cycloalkyl, preferably cyclopropyl, cyclobutyl, cyclopentyl or cyclohexyl. For example, Q may be:

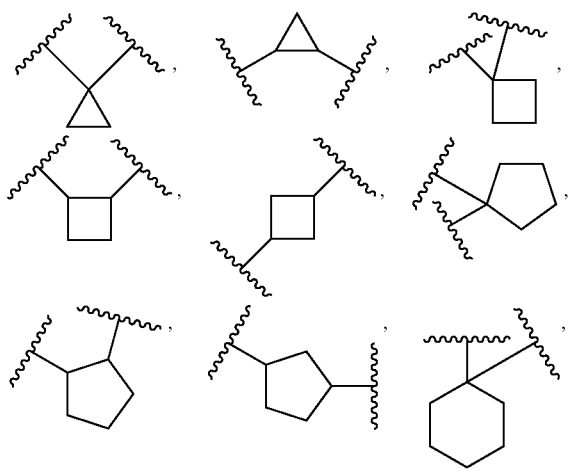

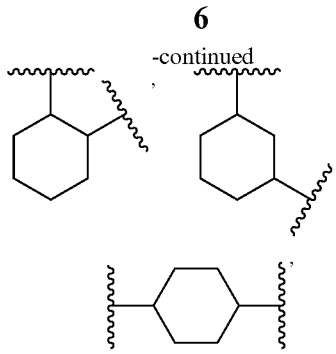

wherein the wavy lines indicate the points of attachment of the carbocyle with the pyrazoloquinazolinone and with Ar. In some embodiments, Q is cyclopropyl, cyclobutyl, cyclopentyl, 4-piperidinyl or cyclohexyl.

A is a direct bond or a linker chosen from: —$CR^6R^7$— and —C(=O)—, preferably a direct bond. When A is —$CR^6R^7$—, $R^6$ and $R^7$ are independently selected from methyl and hydrogen.

In a second set of embodiments $R^{10}$ is chosen from $(C_1-C_{10})$ hydrocarbyl, $(C_1-C_{10})$halohydrocarbyl, $(C_1-C_6)$hydroxyalkyl, and

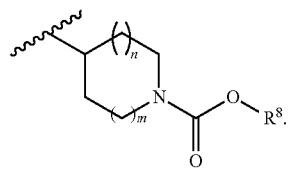

In some embodiments, n is zero. In other embodiments, n is one.

In some embodiments, m is zero. In other embodiments, m is one. In yet other embodiments, m is two.

In some embodiments, p is zero. In other embodiments, p is one.

In some embodiments, t is zero. In other embodiments, t is one. In yet other embodiments, t is two.

In some embodiments, g is zero. In other embodiments, g is one.

In some embodiments, f is zero. In other embodiments, f is one. In yet other embodiments, f is two.

In some embodiments, s is zero. In other embodiments, s is one.

In some embodiments, q is zero. In other embodiments, q is one. In yet other embodiments, q is two or II.

In summary, the invention relates to:

[1] A compound of formula I or II.

[2] A compound according to [1] above wherein $R^1$ is chosen from H, halogen, trifluoromethyl, —CN, $(C_1-C_{10})$ carboxy, ethynyl, trifluoromethoxy and $(C_1-C_3)$alkyl, and $R^2$ is H or halogen.

[3] A compound according to [1] above wherein $R^2$ is H and $R^1$ is H, halogen, methoxy or trifluoromethyl.

[4] A compound according to any of [1] through [3] wherein $R^3$ is H, aminocarbonyl, or CN.

[5] A compound according to any of [1] through [3] wherein $R^3$ is CN.

[6] A compound according to any of [1] through [5] wherein $R^4$ and $R^5$ are H.

[7] A compound according to any of [1] through [6] wherein Ar is chosen from phenyl, thiophenyl, pyrimidine, pyrrolyl, and pyridinyl, any of which may be optionally substituted with from one to three substituents independently chosen from halogen, $(C_1-C_6)$hydrocarbon, fluoro $(C_1-C_6)$alkyl, —O—$(C_1-C_6)$fluoroalkyl, $(C_1-C_6)$alkoxycarbonyl and $(C_1-C_6)$acyl.

[8] A compound according to any of [1] through [6] wherein Ar is phenyl substituted with from one to three substituents chosen from halogen and fluoro($C_1-C_3$)alkyl.

[9] A compound according to any of [1] through [8] wherein Q is a direct bond or $(C_3-C_6)$cycloalkyl

[10] A compound according to any of [1] through [8] wherein Q is cyclopropyl, cyclobutyl, cyclopentyl, 4-piperidinyl or cyclohexyl.

Throughout this specification the terms and substituents retain their definitions.

Alkyl is intended to include linear and branched hydrocarbon structures. Examples of alkyl groups include methyl, ethyl, propyl, isopropyl, cyclopropyl, butyl, s- and t-butyl, n-pentyl, and the like. Preferred alkyl groups are those of $C_{20}$ or below. Cycloalkyl includes cyclic hydrocarbon groups of from 3 to 8 carbon atoms. Examples of cycloalkyl groups include cyclopropyl, cyclobutyl, cyclopentyl, cyclohexyl, norbornyl, adamantyl and the like.

Alkoxy or alkoxyl refers to alkyl groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an aryl ring attached to an alkyl residue in which the point of attachment to the parent structure is through the alkyl. Examples are benzyl, phenethyl and the like. Heteroarylalkyl means an a heteroaryl ring attached through an alkyl residue to the parent structure. Examples include, e.g., pyridinylmethyl, pyrimidinylethyl and the like.

$C_1$ to $C_{10}$ hydrocarbon or hydrocarbyl (when a substituent) means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, cyclopropylmethyl, cyclobutylmethyl, allyl and camphoryl.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, cyclobutane, cyclopentane, cyclohexane, benzene, cyclohexene and cyclohexadiene; $(C_8-C_{12})$ carbopolycycle refers to such systems as norbornane, decalin, indane, adamantane and naphthalene. Carbocycle, if not otherwise limited, refers to monocycles, bicycles and polycycles.

Heterocycle means a cycloalkyl or aryl residue in which one to three of the carbons is replaced by a heteroatom such as oxygen, nitrogen or sulfur. Heteroaryls form a subset of heterocycles. Examples of heterocycles include pyrrolidine, pyrazole, pyrrole, imidazole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, pyrazine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). Although in most cases of "optionally substituted" residues, 1, 2 or 3 hydrogen atoms are replaced with a specified radical, in the case of fluoroalkyl residues, more than three hydrogen atoms can be replaced by fluorine; indeed, all available hydrogen atoms could be replaced by fluorine, e.g. perfluoropropyl.

As used herein, and as would be understood by the person of skill in the art, the recitation of "a compound"—unless expressly further limited—is intended to include salts of that compound. In a particular embodiment, the term "compound of formula I (or II)" refers to the compound or a pharmaceutically acceptable salt thereof.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include, for example, $^{2}H$, $^{3}H$, $^{11}C$, $^{13}C$, $^{14}C$, $^{15}N$, $^{35}S$, $^{18}F$, $^{36}C$, $^{123}I$, $^{125}I$, $^{131}I$ and $^{133}I$. Compounds that contain those radioisotopes and/or other radioisotopes of other atoms are within the scope of this invention. Compounds containing $^{3}H$, $^{14}C$ and iodine radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formulae I and II of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

When the compounds of formula I or II are to be employed as antitumor agents in vivo, they may be administered as the raw chemical, but it is preferable to present them as a pharmaceutical composition. According to a further aspect, the present invention provides a pharmaceutical composition comprising a compound of formula I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

As used herein, the terms "treatment" or "treating," or "palliating" or "ameliorating" refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder.

Abbreviations

The following abbreviations and terms have the indicated meanings throughout:

Ac=acetyl
Boc=t-butyloxy carbonyl
BOP=benzotriazol-1-yloxy-tris(dimethylamino)phosphonium hexafluorophosphate
Bu=butyl
BSA=bovine serum albumin
c-=cyclo DCM=dichloromethane=methylene chloride=$CH_2Cl_2$
DIEA=diisopropylethylamine
DMEM=Dulbecco's modified Eagle medium
DMF=N,N-dimethylformamide
DMSO=dimethyl sulfoxide
DTT=dithiothreitol EtOAc=ethyl acetate
EtOH=ethanol
GC=gas chromatography
HOAc=acetic acid
Me=methyl
MTBE=methyl t-butyl ether
PBS=phosphate buffered saline
PEG=polyethylene glycol
PMSF=phenylmethanesulfonyl fluoride
Ph=phenyl
PhOH=phenol
PVDF=polyvinylidene fluoride
rt=room temperature
sat'd=saturated
s-=secondary
SDS=sodium dodecylsulfate
T3P=2,4,6-Tripropyl-1,3,5,2,4,6-trioxatriphosphorinane-2,4,6-trioxide
t- or tert-=tertiary
TBDMS=t-butyldimethylsilyl
TFA=trifluoroacetic acid
THF=tetrahydrofuran
TMS=trimethylsilyl
tosyl=p-toluenesulfonyl

SYNTHETIC METHODS

1. Formation of General Formula I Tricycle—Method A

Some compounds of the general formula I were obtained by the reaction of 2-hydrazinobenzoic acids with 3-phenyl-3-oxo-propanenitriles, e.g.,

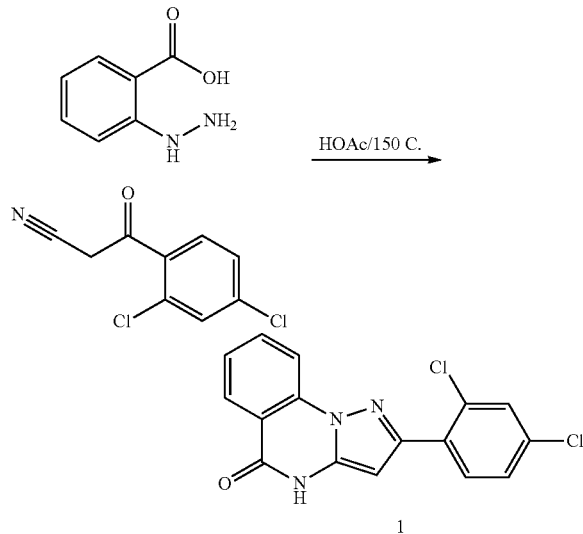

Example 1. 2-(2,4-dichlorophenyl)-4H-pyrazolo[1,5-a]quinazolin-5-one

A mixture of 2-hydrazinobenzoic acid (43.3 mg, 285 μmol), 3-(2,4-dichlorophenyl)-3-oxo-propanenitrile (41.2 mg, 192 μmol) and acetic acid (2.0 mL) was stirred at 150° C. under microwave irradiation for 30 min. The mixture was diluted with water and ethyl acetate, the insoluble material was collected by filtration to give the desired compound as a colorless solid (7.5 mg). The filtrate was extracted with ethyl acetate. The combined organic layer was washed with water and brine, dried over $MgSO_4$, filtered and concentrated in vacuo. The solid was washed with ethyl acetate to give the desired compound (9.4 mg). The combined solid was washed with hexane to give 2-(2,4-dichlorophenyl)-4H-pyrazolo[1,5-a]quinazolin-5-one (16.4 mg, 49.7 μmol, 26% yield) as a colorless solid. $^1$H NMR (500 MHz, DMSO-d6) δ 12.34 (s, 1H), 8.19 (dd, J=11.4, 8.2 Hz, 2H), 7.99 (d, J=8.4 Hz, 1H), 7.94 (t, =7.7 Hz, 1H), 7.80 (s, 1H), 7.61-7.53 (m, 2H), 6.42 (s, 1H). LCMS m/z: 329.9 [M+H]$^+$.

2. Formation of General Formula I Tricycle—Method B

Alternatively, some compounds of the general formula I were obtained by the reaction of 5-amino-1H-pyrazoles with 2-fluorobenzoic acid esters, e.g., Example 2. 2-(2,4-dichlorophenyl)-5-oxo-4H-pyrazolo[1,5-a]quinazoline-3-carbonitrile

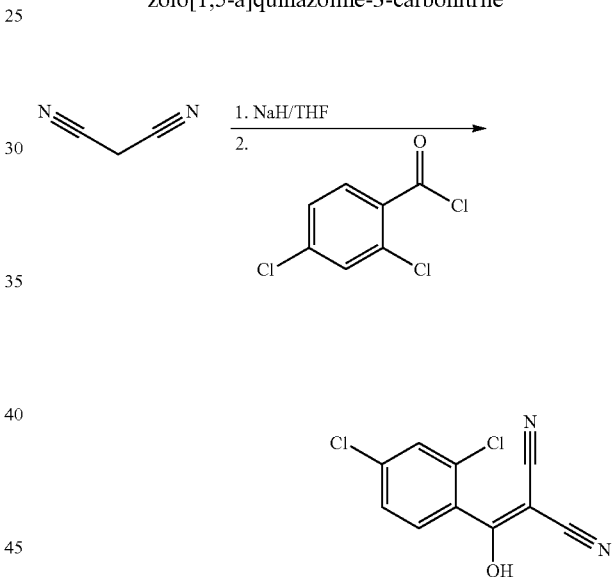

To a stirred solution of propanedinitrile (4.71 g, 71.3 mmol) in THF (150 mL) were added sodium hydride (5.71 g, 143 mmol, 60% purity) at 0° C. The mixture was stirred at room temperature for 1 h. The solution of 2,4-dichlorobenzoyl chloride (14.6 g, 69.8 mmol, 10 mL) in THF (50 mL) was added to the mixture at 0° C. The mixture was stirred at room temperature for 4 h. The mixture was diluted with 1N HCl (aq.) and extracted with ethyl acetate. The combined organic layer was washed with water and brine, dried over $MgSO_4$, filtered and concentrated in vacuo. The residue was purified by column chromatography (ethyl acetate/hexanes) to give 2-[(2,4-dichlorophenyl)-hydroxymethylene]propanedinitrile (17.38 g, 72.70 mmol, 104% yield) as light yellow amorphous powder. This product was subjected directly to the next reaction. $^1$H NMR (500 MHz, Chloroform-d) δ7.55 (s, 1H), 7.46-7.38 (m, 2H). LCMS m/z: 236.992 [M−H]$^−$.

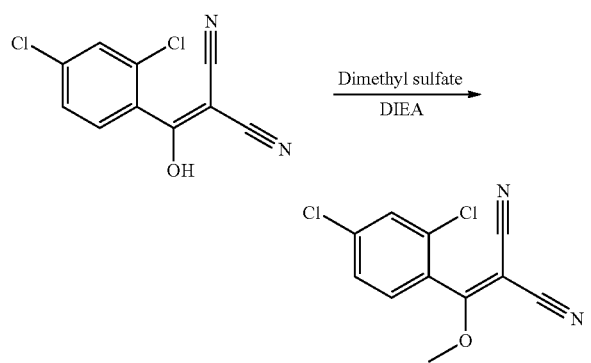

A mixture of 2-[(2,4-dichlorophenyl)-hydroxymethylene]propanedinitrile (17.4 g, 72.7 mmol), dimethyl sulfate (18.3 g, 145 mmol, 13.8 mL) and N-ethyl-N-isopropyl-propan-2-amine (28.2 g, 218 mmol, 38.1 mL) in dioxane (200 mL) was stirred at 60° C. for 23 h. The reaction was cooled to room temperature and concentrated in vacuo. The residue was dissolved with ethyl acetate and quenched with water. The organic layer was separated, washed with brine, dried over MgSO₄, filtered and concentrated in vacuo. The residue was purified by column chromatography (hexane/ethyl acetate) to give 2-[(2,4-dichlorophenyl)-methoxymethylene]propanedinitrile (3.19 g, 12.60 mmol, 17% yield) as a brown solid. (Known compound, CAS: 1188083-55-7). $^1$H NMR (500 MHz, Chloroform-d) δ 7.62 (d, J=1.9 Hz, 1H) 7.49 (dd, J=83, 1.9 Hz, 1H), 734 (d, J=83 Hz. 1H), 3.85 (s 3H).

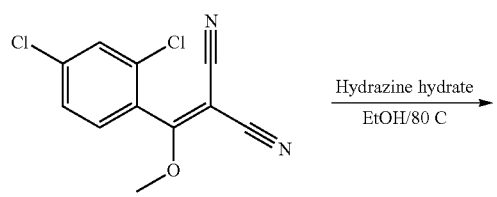

A mixture of 2-[(2,4-dichlorophenyl)methoxymethylene]propanedinitrile (3.19 g, 12.6 mmol) and hydrazine hydrate (694 mg, 13.4 mmol, 672 μL) in ethanol (50 mL) was stirred at 80° C. for 4.5 h. Additional hydrazine hydrate (252 mg, 5.04 mmol, 244 μL) was added to the mixture and it was stirred at 80° C. for 1.5 h. The reaction was concentrated in vacuo. The residue was washed with ethanol to give 5-amino-3-(2,4-dichlorophenyl)-1H-pyrazole-4-carbonitrile (1.73 g, 6.84 mmol, 54% yield) as an off-white solid. $^1$H NMR: (500 MHz, DMSO-d6) δ 12.31 (s, 1H), 7.76 (s, 1H), 7.58-7.41 (m, 2H), 6.49 (s, 2H). LCMS m/z: 253.184 [M+H]⁺.

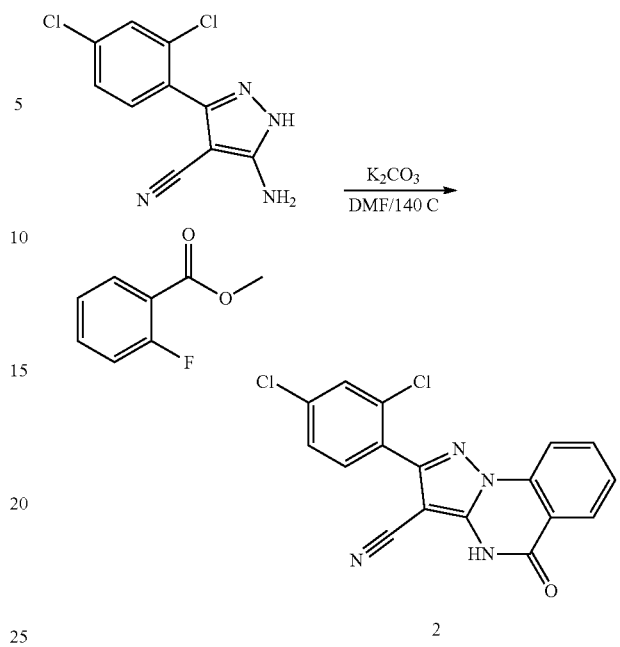

A mixture of 5-amino-3-(2,4-dichlorophenyl)-1H-pyrazole-4-carbonitrile (100 mg, 395 mol), dipotassium carbonate (81.9 mg, 593 μmol) and methyl 2-fluorobenzoate (73.1 mg, 474 μmol, 60.4 μL) in dimethylformamide (1.0 mL) was stirred at 140° C. for 30 min. The mixture was poured into water, and extracted with ethyl acetate. The organic layer was washed with water and brine respectively, dried over MgSO₄ and concentrated in vacuo. The residue was purified by silica-gel column chromatography (hexane/ethyl acetate) to give 2-(2,4-dichlorophenyl)-5-oxo-4H-pyrazolo[1,5-a]quinazoline-3-carbonitrile (2) (14.2 mg, 40.0 μmol, 10% yield) as a white solid. $^1$H NMR: (500 MHz, DMSO-d6) δ 8.09 (d, J=7.8 Hz, 1H), 7.94 (d, J=8.2 Hz 1H), 7.83 (d, J=2.0 Hz 1H), 7.73-7.56 (m, 3H), 7.40 (t, J=7.5 Hz, 1H). LCMS m/z: 353.136 [M−H]⁻.

Example 3. 2[1-(4-chlorophenyl)cyclopropyl]-5-oxo-4H-pyrazolo[1,5-a]quinazoline-3-carbonitrile

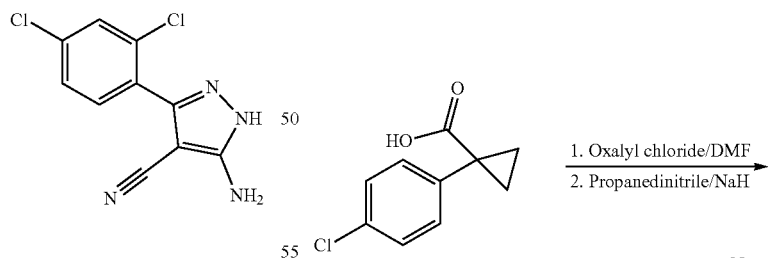

To a solution of 1-(4-chlorophenyl)cyclopropanecarboxylic acid (10.0 g, 50.9 mmol) in THF (100 mL) were added oxalyl chloride (7.75 g, 61 mmol, 5.33 mL) and dimethylformamide (37.2 mg, 509 μmol, 39.5 μL). The mixture was stirred at room temperature for 0.5 h. The mixture was concentrated in vacuo. The mixture was added to a solution of propanedinitrile (3.36 g, 50.9 mmol) and sodium hydride (4.07 g, 102 mmol, 60% purity) in THF (100 mL) at 0° C. The mixture was stirred at room temperature for 1 h. The mixture was diluted with 1N HCl and extracted with ethyl acetate. The combined organic layer was washed with water and brine, dried over Na$_2$SO$_4$, filtered and concentrated under reduced pressure. The residue was purified by column chromatography (hexane/ethyl acetate) to give 2((1-(4-chlorophenyl)cyclopropyl)(hydroxy)-methylene)malononitrile (12.0 g, 49 mmol, 96% yield) as a light yellow oil. $^1$H NMR (500 MHz, DMSO-d6) δ 7.36-7.30 (m, 2H), 7.22 (dd, J=7.8, 2.0 Hz, 2H), 1.22-1.16 (m, 2H), 0.97 (d, J=3.6 Hz, 2H).

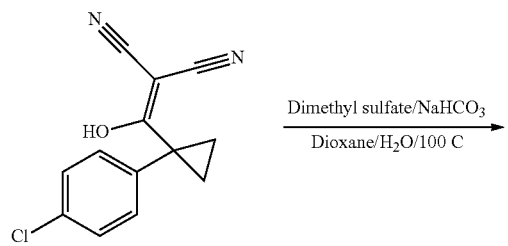

To a solution of 2((1-(4-chlorophenyl)cyclopropanecarbonyl]propanedinitrile (12.0 g, 49.0 mmol) in dioxane (200 mL) and H$_2$O (20 mL) were added dimethyl sulfate (18.6 g, 147 mmol, 13.9 mL) and NaHCO$_3$ (20.6 g, 245 mmol). The mixture was stirred at 100° C. for 5 hours. The mixture was poured into water, and extracted with ethyl acetate. The organic layer was washed with brine, dried over Na$_2$SO$_4$ and concentrated in vacuo. The residue was purified by column chromatography (hexane/ethyl acetate) to give 2((1-(4-chlorophenyl)cyclopropyl)(methoxy)methylene)malononitrile (3.38 g, 13.1 mmol, 27% yield) as a yellow oil. $^1$H NMR (500 MHz, DMSO-d6) δ 7.55-7.45 (m, 2H), 7.33-7.22 (m, 2H), 4.04 (s, 3H), 1.80-1.71 (m, 2H), 1.68-1.61 (m, 2H).

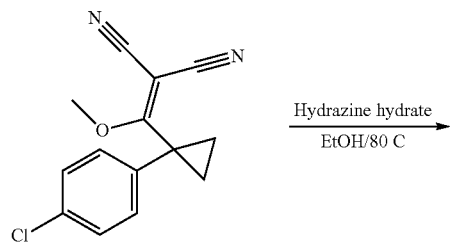

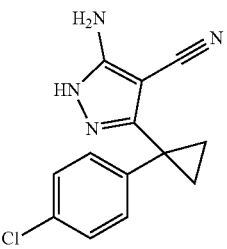

To a solution of 2-[[1-(4-chlorophenyl)cyclopropyl]methoxymethylene]propanedinitrile (3.38 g, 13.1 mmol) in ethanol (100 mL) was added hydrazine hydrate (981 mg, 19.6 mmol). The mixture was stirred at 80° C. for 2 h. The mixture was concentrated in vacuo. The residue was purified by column chromatography (hexane/ethyl acetate) to give 5-amino-3[1-(4-chlorophenyl)cyclopropyl]-1H-pyrazole-4-carbonitrile (2.77 g, 10.7 mmol, 82% yield) as a white powder. $^1$H NMR (500 MHz, DMSO-d6) δ 11.73 (s, 1H), 7.35 (d, J=8.0 Hz, 2H), 7.27-7.16 (m, 2H), 6.28 (s, 2H), 1.43-1.13 (m, 4H). LCMS m/z: 259 [M+H]$^+$.

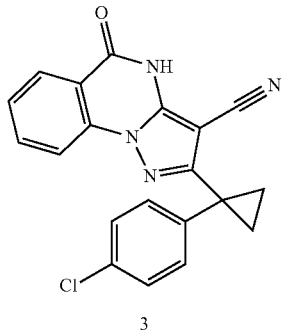

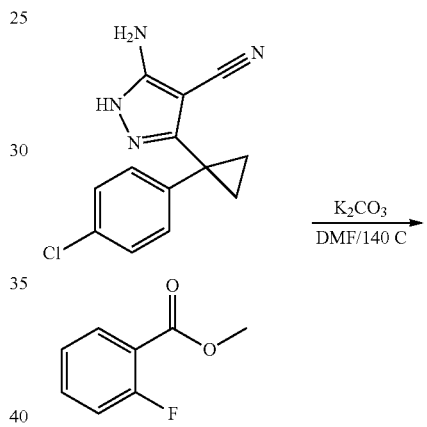

A mixture of 5-amino-3 [1-(4-chlorophenyl)cyclopropyl]-1H-pyrazole-4-carbonitrile (100 mg, 387 μmol), dipotassium carbonate (80.1 mg, 580 μmol) and methyl 2-fluorobenzoate (71.5 mg, 464 μmol, 59.1 μL) in dimethylformamide (1.0 mL) was stirred at 140° C. for 30 min. The mixture was poured into water, and extracted with ethyl acetate. The organic layer was washed with water and brine respectively, dried over MgSO$_4$ and concentrated in vacuo. The residue was purified by flash chromatography (ethyl acetate/hexane) to give 2-[1-(4-chlorophenyl)cyclopropyl]-5-oxo-4H-pyrazolo[1,5-a]quinazoline-3-carbonitrile (3) (16.0 mg, 44.0 μmol, 11% yield) as a white solid. $^1$H NMR (500 MHz, DMSO-d6) δ 13.23 (s, 1H), 8.17 (d, J=7.9

Hz, 1H), 8.10 (d, J=8.2 Hz, 1H), 7.95 (t, 1=7.8 Hz, 1H), 7.59 (t, J=7.6 Hz, 1H), 7.38 (d, J=8.2 Hz, 2H), 7.32 (d, J=8.3 Hz, 2H), 1.55 (q, J=4.6 Hz, 2H), 1.42 (q, J=4.6 Hz, 2H). LCMS m/z: 361.233 [M+H]+.

In a like manner, compounds 4 and 5 in Table 1 were synthesized.

Example 4. 2-(1-(4-chlorophenyl)cyclopropyl)-5-oxo-7-(trifluoromethyl)-4,5-dihydropyrazolo[1,5-a]quinazoline-3-carbonitrile

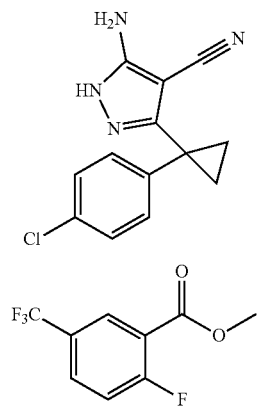

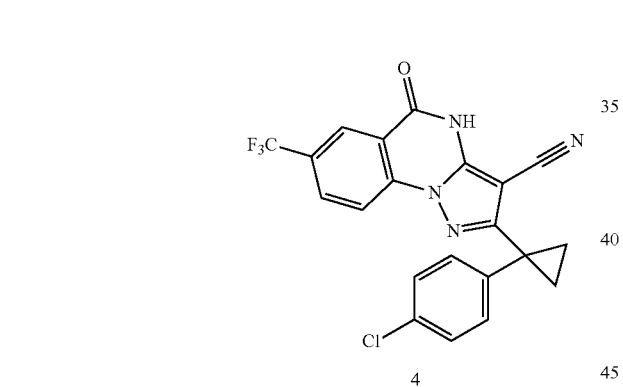

4

A mixture of 5-amino-3-[1-(4-chlorophenyl)cyclopropyl]-1H-pyrazole-4-carbonitrile (80.0 mg, 309 µmol), methyl 2-fluoro-5-(trifluoromethyl)benzoate (75.6 mg, 340 µmol) and dipotassium carbonate (64.1 mg, 464 µmol) in dimethylformamide (1.0 mL) was stirred at 140° C. for 30 min under microwave irradiation. The mixture was poured into water, and extracted with ethyl acetate. The organic layer was washed successively with water and brine, dried over MgSO4 and concentrated in vacuo. The residue was purified by column chromatography (ethyl acetate/hexane) to give a mixture. The amorphous material was triturated with acetonitrile and the white precipitate was collected to give 2-[1-(4-chlorophenyl)cyclopropyl]-5-oxo-7-(trifluoromethyl)-4H-pyrazolo[1,5-a]quinazoline-3-carbonitrile (4) (26.2 mg, 61.1 µmol, 20% yield) as a white solid. 1H NMR (500 MHz, DMSO-d6) δ 13.49 (s, 1H), 8.36 (s, 1H), 8.25 (d, J=–1.3 Hz, 2H), 7.42-7.35 (m, 2H), 7.35-7.27 (m, 2H), 1.63-1.52 (m, 2H), 1.48-138 (m, 2H). LCMS m/z: 429.2 [M+H]+.

Example 5. 2-[1-(4-chlorophenyl)cyclopropyl]-7-iodo-5-oxo-411-pyrazolo[1,5-a]quinazoline-3-carbonitrile

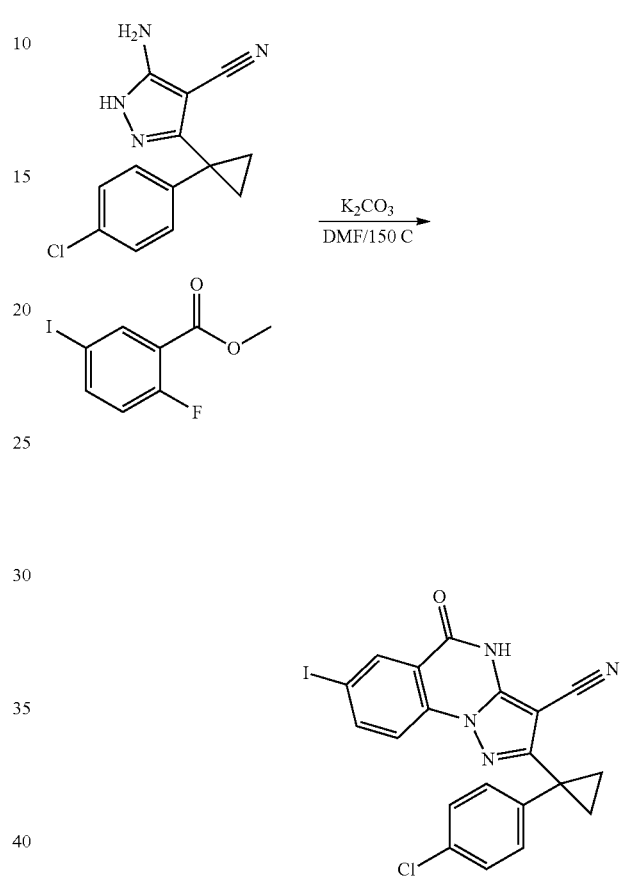

5

A mixture of 5-amino-3-[1-(4-chlorophenyl)cyclopropyl]-1H-pyrazole-4-carbonitrile (499 mg, 1.93 mmol), methyl 2-fluoro-5-iodo-benzoate (600 mg, 2.14 mmol) and dipotassium carbonate (414 mg, 3.21 mmol) in dimethylformamide (10 mL) was stirred at 150° C. for 1 h under microwave irradiation. The reaction was cooled to room temperature and poured into water. The white precipitate was collected and washed with ethyl acetate to give 2-[1-(4-chlorophenyl)cyclopropyl]-7-iodo-5-oxo-4H-pyrazolo[1,5-a]quinazoline-3-carbonitrile (5) (400 mg, 822 µmol, 38% yield) as a white solid. 1H NMR (500 MHz, Chloroform-d) δ 9.78 (s, 1H), 8.65 (d, J 2.0 Hz, 1H), 8.15 (dd, J=8.7, 2.0 Hz, 1H), 7.91 (d, J=8.6 Hz, 1H), 7.43-7.32 (m, 4H), 1.64 (d, J 2.4 Hz, 2H, overlaps with a peak for residual water), 1.41 (q, J=4.6 Hz, 2H). LCMS m/z: 487.0 [M+H]+.

3. Formation of General Formula II Tricycle—Method C

Some compounds of the general formula II are synthesized in a manner analogous to the process above except substituting propylphosphonic anhydride (T3P) in place of potassium carbonate at elevated temperature for the condensation step:

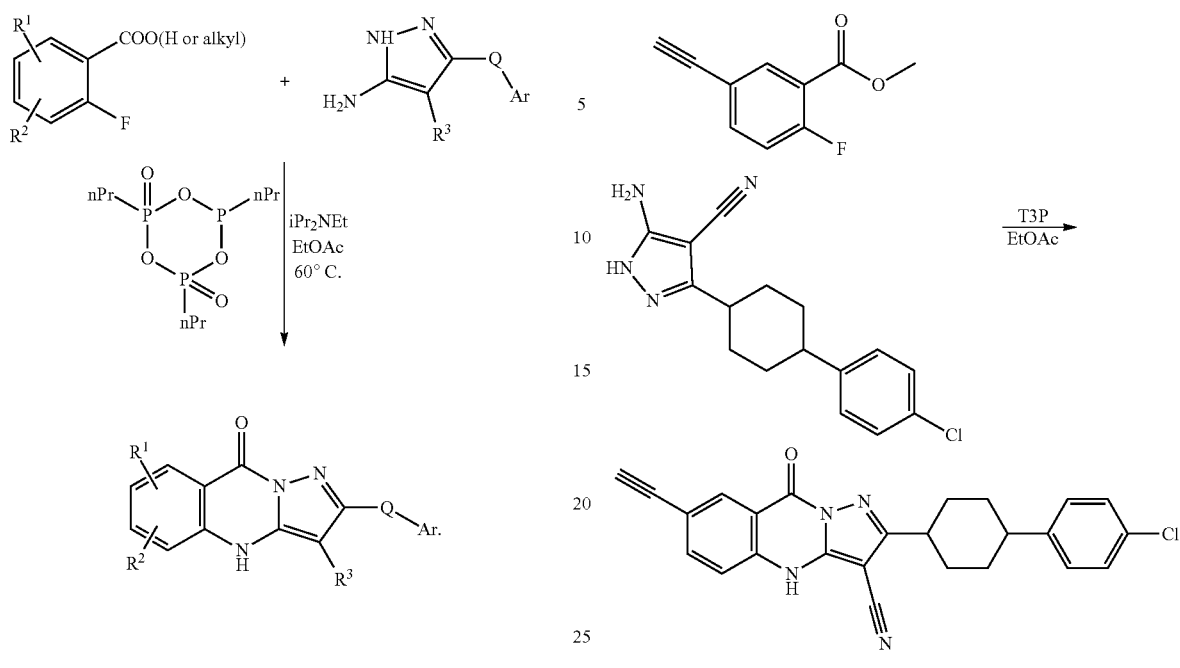

Example 6. 2-[4-(4-chlorophenyl)cyclohexyl]-7-ethynyl-9-oxo-4H-pyrazolo[5,1-b]quinazoline-3-carbonitrile

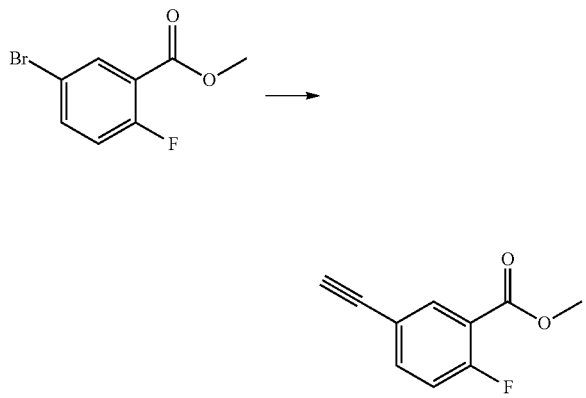

To a mixture of methyl 5-bromo-2-fluoro-benzoate (1.51 g, 6.48 mmol), palladium; triphenylphosphane (374.4 mg, 324 μmol), copper iodide (1.23 g, 6.48 mmol), and DIEA (1.26 g, 9.72 mmol) in toluene (15.0 mL) was added ethynyl(trimethyl)silane (954.7 mg, 9.72 mmol) at room temperature, and the mixture was stirred at 80° C. for 2 h. The reaction mixture was filtered, and the filtrate was concentrated in vacuo. The residue was purified by column chromatography (Silica gel, 5-15%, AcOEt in Hexane) to give crude product. The crude product and potassium carbonate (1.59 g, 11.5 mmol) was stirred in MeOH (10.0 mL) at room temperature for 1 h. The reaction was quenched with water and extracted with AcOEt. The organic layer was washed with water, and brine, dried over MgSO₄ and concentrated in vacuo. The residue was purified by column chromatography (Silica gel, 0-10%, AcOEt in Hexane) to give methyl 5-ethynyl-2-fluoro-benzoate (432.0 mg, 2.42 mmol, 37% yield) as white solid.

A mixture of methyl 5-ethynyl-2-fluoro-benzoate (40.1 mg, 225 μmol), 5-amino-3-[4-(4-chlorophenyl)cyclohexyl]-1H-pyrazole-4-carbonitrile (63.3 mg, 210 μmol), Hunig's base (272 mg, 2.10 mmol) and T3P (801.8 mg, 1.26 mmol, 50% purity) in AcOEt (2.00 mL) was stirred at 80° C. for 16 h. The reaction mixture was concentrated in vacuo. The residue was purified by column chromatography (silica-gel, 25-55% AcOEt in Hexane) and washed with MeOH to give 2-[4-(4-chlorophenyl)cyclohexyl]-7-ethynyl-9-oxo-4H-pyrazolo[5,1-b]quinazoline-3-carbonitrile (2.0 mg, 4.7 μmol, 2% yield) as pale yellow solid.

¹H NMR (500 MHz, DMSO-d₆) δ 13.43 (s, 1H), 8.21 (d, J=1.8 Hz, 1H), 7.88 (dd, J=8.6, 2.0 Hz, 1H), 7.55 (d, J=8.6 Hz, 1H), 7.41-7.29 (m, 4H), 4.31 (s, 1H), 2.94 (tt, J=12.1, 3.5 Hz, 1H), 2.64 (tt, J=11.9, 3.5 Hz, 1H), 2.12 (dd, J=13.6, 3.6 Hz, 2H), 1.98-1.89 (m, 2H), 1.79 (qd, J=12.8, 3.3 Hz, 2H), 1.65 (qd, J=12.8, 3.3 Hz, 2H).

Example 7. tert-Butyl 4-(3-cyano-7-ethynyl-9-oxo-4H-pyrazolo[5,1-b]quinazolin-2-yl)piperidine-1-carboxylate

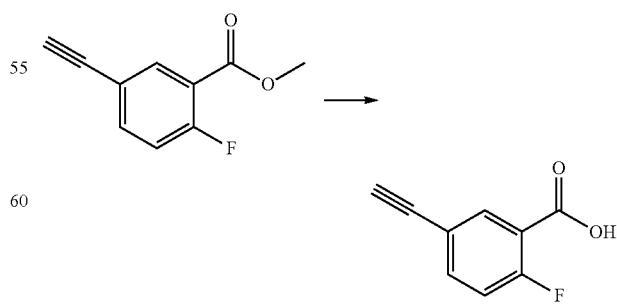

To a THF (3.0 mL) and MeOH (3.0 mL) solution of methyl 5-ethynyl-2-fluoro-benzoate (432.0 mg, 2.42 mmol)

was added 1.0 N NaOH aq. (2.42 mL, 2.42 mmol) at room temperature, and the mixture was stirred for 2 h. The reaction was quenched with 1N HCl and extracted with AcOEt. The organic layer was washed with water and brine, dried over MgSO$_4$, and concentrated in vacuo. The residue was washed with hexane to give 5-ethynyl-2-fluoro-benzoic acid (358.2 mg, 2.18 mmol, 90% yield) as white solid. $^1$H NMR (500 MHz, DMSO-d$_6$) δ 7.93 (dd, J=6.9, 2.3 Hz, 1H), 7.78 (ddd, J=8.5, 4.6, 2.3 Hz, 1H), 7.41 (dd, J=10.8, 8.6 Hz, 1H), 4.32 (s, 1H), 3.86 (s, 3H). MS m/z: 179 [M–H]$^+$.

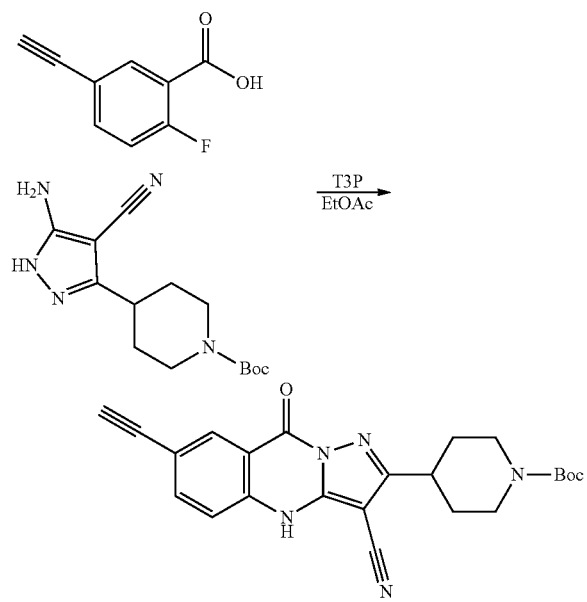

A mixture of 5-ethynyl-2-fluoro-benzoic acid (50.1 mg, 281 µmol), tert-butyl 4-(5-amino-4-cyano-1H-pyrazol-3-yl)piperidine-1-carboxylate (75.1 mg, 258 µmol), Hunig's base (333.1 mg, 2.58 mmol) and T3P (982.6 mg, 1.54 mmol, 50% purity) in AcOEt (2.0 mL) was stirred at 80° C. for 3 h. The reaction mixture was concentrated in vacuo. The residue was washed with MeOH to give tert-butyl 4-(3-cyano-7-ethynyl-9-oxo-4H-pyrazolo[5,1-b]quinazolin-2-yl)piperidine-1-carboxylate (53.4 mg, 128 µmol, 50% yield) as white solid. $^1$H NMR (500 MHz, DMSO-d$_6$) δ 13.44 (s, 1H), 8.20 (d, J=1.8 Hz, 1H), 7.86 (d, J=8.5 Hz, 1H), 7.54 (d, J=8.6 Hz, 1H), 4.30 (s, 1H), 4.04 (d, J=13.0 Hz, 2H), 3.07 (tt, J=11.8, 3.7 Hz, 1H), 2.92 (s, 2H), 1.93 (dd, J=13.3, 3.6 Hz, 2H), 1.76-1.59 (m, 2H), 1.42 (s, 9H). MS m/z: 362 [M+H-t-Bu]$^+$.

Example 8. 7-Ethynyl-9-oxo-2-[1-[[4-[3-(trifluoromethyl)diazirin-3-yl]phenyl]methyl]-4-piperidyl]-4H-pyrazolo[5,1-b]quinazoline-3-carbonitrile

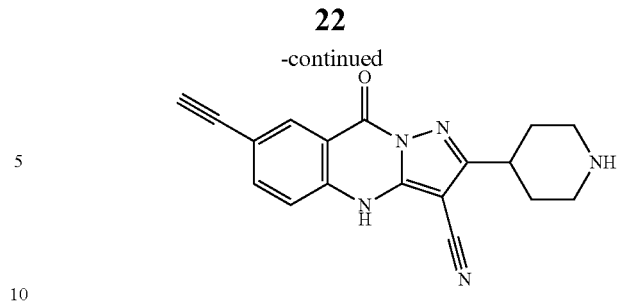

To a suspension of tert-butyl 4-(3-cyano-7-ethynyl-9-oxo-4H-pyrazolo[5,1-b]quinazolin-2-yl)piperidine-1-carboxylate (107.4 mg, 257 µmol) in MeOH (2.0 mL) was added 4 M HCl in dioxane (5.0 ml, 20 mmol) at room temperature, and the mixture was stirred for 1 h. The resulting solid was collected, washed with AcOEt go give 7-ethynyl-9-oxo-2-(4-piperidyl)-4H-pyrazolo[5,1-b]quinazoline-3-carbonitrile hydrochloride (49.8 mg, 141 µmol, 55% yield, HCl salt) as white solid. The filtrate was concentrated in vacuo and washed with AcOEt to give 7-ethynyl-9-oxo-2-(4-piperidyl)-4H-pyrazolo[5,1-b]quinazoline-3-carbonitrile hydrochloride (6.9 mg, 76.0 µmol, 30% yield, HCl salt) as white solid. $^1$H NMR (500 MHz, DMSO-d$_6$) δ 13.52 (s, 1H), 8.87-8.66 (m, 1H), 8.59-8.34 (m, 1H), 8.22 (d, J=1.9 Hz, 1H), 7.89 (dd, J=8.5, 1.9 Hz, 1H), 7.57 (d, J=8.7 Hz, 1H), 4.33 (s, 1H), 3.44-3.35 (m, 2H), 3.29-3.19 (m, 1H), 3.15-3.03 (m, 2H), 2.20-2.09 (m, 2H), 2.05-1.90 (m, 2H). MS m/z: 318 [M+H]$^+$.

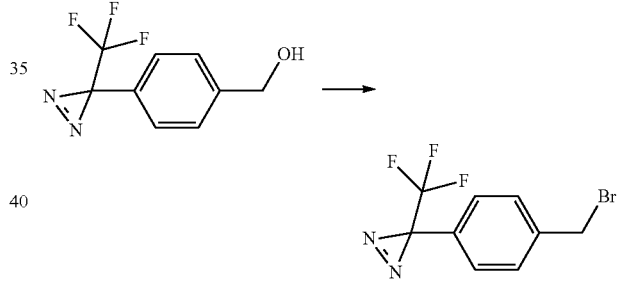

To a DCM (3.0 mL) solution of [4-[3-(trifluoromethyl)diazirin-3-yl]phenyl]methanol (147.3 mg, 681 µmol) and carbon tetrabromide (278.0 mg, 838 µmol) was added triphenylphosphine (234.1 mg, 893 µmol) at room temperature, and the mixture was stirred for 15 min. The reaction mixture was diluted with hexane, and the solid was filtered. The filtrate was concentrated in vacuo (this procedure was repeated twice) to give 3-[4-(bromomethyl)phenyl]-3-(trifluoromethyl)diazirine (205.8 mg, 681 µmol, 100% yield, 92.3% purity) as colorless oil. This product was used to next step without further purification.

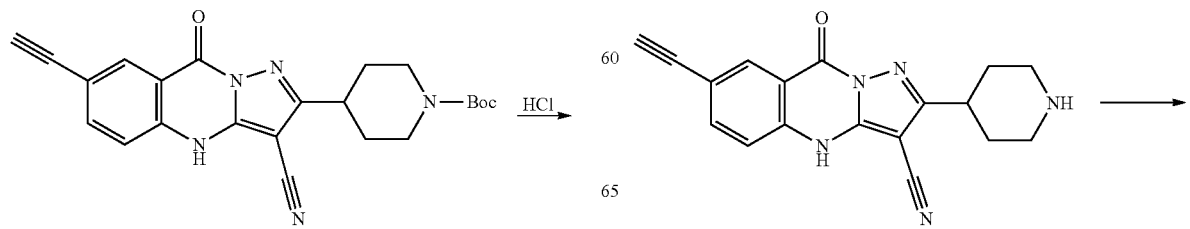

-continued

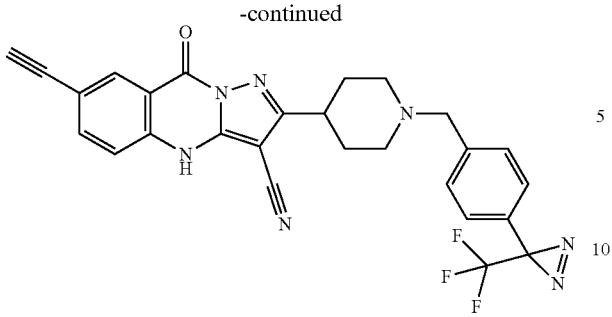

To a mixture of 7-ethynyl-9-oxo-2-(4-piperidyl)-4H-pyrazolo[5,1-b]quinazoline-3-carbonitrile hydrochloride (22.9 mg, 64.7 µmol, HCl salt) and DIEA (56.51 µL, 324 µmol) was added crude 3-[4-(bromomethyl)phenyl]-3-(trifluoromethyl)diazirine (35.0 mg, 116 µmol) at room temperature, and the mixture was stirred for 16 h. The reaction mixture was concentrated in vacuo. The reaction was quenched with water and extracted with AcOEt. The organic layer was washed with water and brine, dried over MgSO$_4$, and concentrated in vacuo. The residue was purified by column chromatography (Silica gel, 20-80%, AcOEt in Hexane). The residue was suspended in 1N HCl in AcOEt, and the mixture was concentrated in vacuo. The residue was washed with MeOH to give 7-ethynyl-9-oxo-2-[1-[[4-[3-(trifluoromethyl)diazirin-3-yl]phenyl]methyl]-4-piperidyl]-4H-pyrazolo[5,1-b]quinazoline-3-carbonitrile hydrochloride (2.5 mg, 4.5 µmol, 7% yield, HCl salt) as white solid. $^1$H NMR (500 MHz, DMSO-d$_6$) δ 13.52 (s, 1H), 10.13 (s, 1H), 8.21 (s, 1H), 7.88 (d, J=8.7 Hz, 1H), 7.73 (d, J=7.9 Hz, 2H), 7.56 (d, J=8.8 Hz, 1H), 7.43 (d, J=8.0 Hz, 2H), 4.47-4.36 (m, 2H), 4.32 (s, 1H), 3.58-3.43 (m, 2H), 3.26-3.06 (m, 3H), 2.38-1.89 (m, 4H). MS m/z: 516 [M+H]$^+$.

Other examples shown below were synthesized using method C:

Example 9. 7-Ethynyl-9-oxo-2-[1-[4-[3-(trifluoromethyl)diazirin-3-yl]benzoyl]-4-piperidyl]-4H-pyrazolo[5,1-b]quinazoline-3-carbonitrile

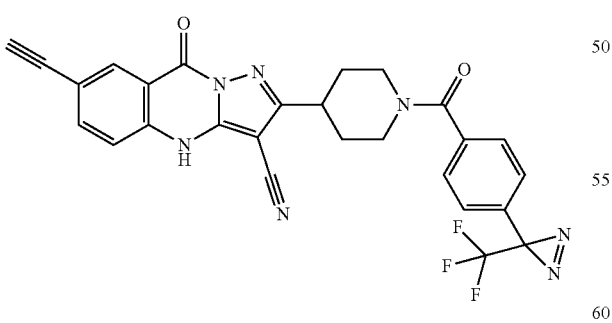

$^1$H NMR (500 MHz, DMSO-d$_6$) δ 13.46 (s, 1H), 8.21 (d, J=1.9 Hz, 1H), 7.87 (d, J=8.6 Hz, 1H), 7.56 (t, J=8.6 Hz, 3H), 7.38 (d, J=8.0 Hz, 2H), 4.63-4.47 (m, 1H), 4.31 (s, 1H), 3.32-3.11 (m, 3H), 3.12-2.95 (m, 1H), 2.18-1.85 (m, 2H), 1.84-1.64 (m, 2H). $^{19}$F NMR (471 MHz, DMSO-d$_6$) δ −66.80.

Example 10. 2-[1-(4-Chlorophenyl)cyclopropyl]-9-oxo-4H-pyrazolo[5,1-b]quinazoline-3,7-dicarbonitrile

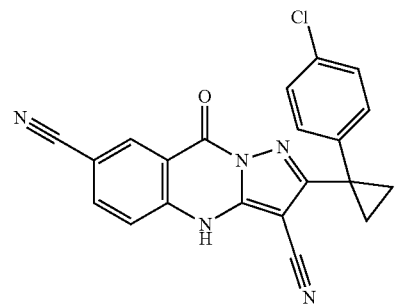 [SMILES: N#Cc1ccc2[nH]c3c(C#N)c(C4(c5ccc(Cl)cc5)CC4)nn3c(=O)c2c1]

$^1$H NMR (500 MHz, DMSO-d$_6$) δ 13.62 (s, 1H), 8.62 (d, J=1.9 Hz, 1H), 8.15 (dd, J=8.7, 2.0 Hz, 1H), 7.64 (d, J=8.6 Hz, 1H), 7.42-7.36 (m, 2H), 7.36-7.29 (m, 2H), 1.59-1.52 (m, 2H), 1.47-1.38 (m, 2H). MS m/z: 386 [M+H]$^+$.

Example 11. 2-[1-(4-Chlorophenyl)cyclopropyl]-9-oxo-7-(trifluoromethyl)-4H-pyrazolo[5,1-b]quinazoline-3-carbonitrile

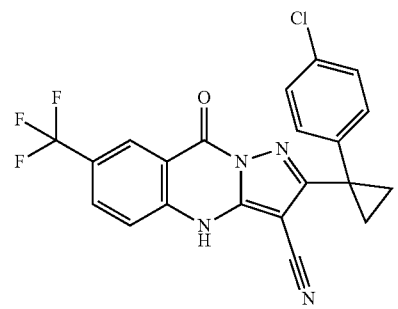 [SMILES: N#Cc1c(C2(c3ccc(Cl)cc3)CC2)nn2c(=O)c3cc(C(F)(F)F)ccc3[nH]c12]

$^1$H NMR (500 MHz, DMSO-d$_6$) δ 13.60 (s, 1H), 8.45 (d, J=2.1 Hz, 1H), 8.15 (dd, J=8.8, 2.2 Hz, 1H), 7.74 (d, J=8.7 Hz, 1H), 7.41 (d, J=8.6 Hz, 2H), 7.36 (d, J=8.6 Hz, 2H), 1.58 (q, J=4.5 Hz, 2H), 1.45 (q, J=4.6 Hz, 2H). MS m/z: 429 [M+H]$^+$.

Example 12. 7-Bromo-2-[1-(4-chlorophenyl)cyclopropyl]-9-oxo-4H-pyrazolo[5,1-b]quinazoline-3-carbonitrile

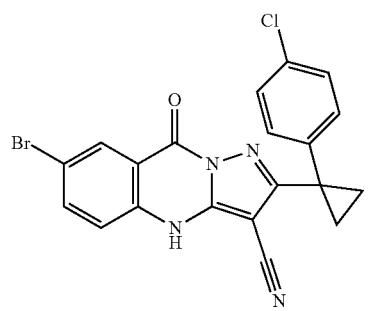

¹H NMR (500 MHz, DMSO-d₆) δ 13.37 (s, 1H), 8.28 (d, J=2.4 Hz, 1H), 7.99 (dd, J=8.9, 2.4 Hz, 1H), 7.53 (d, J=8.9 Hz, 1H), 7.40 (d, J=8.2 Hz, 2H), 7.35 (d, J=8.2 Hz, 2H), 1.57 (q, J=4.5 Hz, 2H), 1.43 (q, J=4.5 Hz, 2H). MS m/z: 439 [M+H]+.

Example 13. 2-[4-(4-Chlorophenyl)cyclohexyl]-7-cyclopropyl-9-oxo-4H-pyrazolo[5,1-b]quinazoline-3-carbonitrile

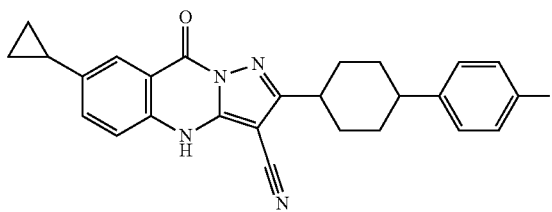

¹H NMR (500 MHz, DMSO-d₆) δ 13.17 (s, 1H), 7.91 (d, J=2.1 Hz, 1H), 7.55 (dd, J=8.8, 2.1 Hz, 1H), 7.47 (d, J=8.7 Hz, 1H), 7.35 (d, J=2.7 Hz, 4H), 2.93 (tt, J=12.0, 3.7 Hz, 1H), 2.64 (ddt, J=12.0, 8.7, 3.3 Hz, 1H), 2.11 (tt, J=8.1, 4.4 Hz, 2H), 1.97-1.88 (m, 3H), 1.79 (qd, J=12.8, 3.2 Hz, 2H), 1.65 (qd, J=12.9, 3.2 Hz, 2H), 1.02 (tt, J=6.5, 3.4 Hz, 2H), 0.79-0.68 (m, 2H). MS m/z: 443 [M+H]⁺.

Example 14. 2-[1-(4-Chlorophenyl)cyclopropyl]-7-cyclopropyl-9-oxo-4H-pyrazolo[5,1-b]quinazoline-3-carbonitrile

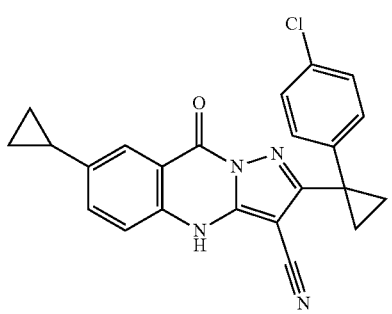 [SMILES: N#Cc1c(C2(c3ccc(Cl)cc3)CC2)nn2c(=O)c3cc(C4CC4)ccc3[nH]c12]

¹H NMR (500 MHz, DMSO-d₆) δ 13.14 (s, 1H), 7.91 (d, J=2.1 Hz, 1H), 7.58-7.50 (m, 1H), 7.46 (d, J=8.6 Hz, 1H), 7.41-7.29 (m, 4H), 2.11 (tt, J=8.8, 5.1 Hz, 1H), 1.54 (h, J=4.4, 4.0 Hz, 2H), 1.40 (q, J=5.3, 4.8 Hz, 2H), 1.07-0.96 (m, 2H), 0.73 (dt, J=6.6, 3.2 Hz, 2H). MS m/z: 401 [M+H]⁺.

Example 15. 2-[4-(4-Chlorophenyl)cyclohexyl]-9-oxo-7-(trifluoromethyl)-4H-pyrazolo[5,1-b]quinazoline-3-carbonitrile

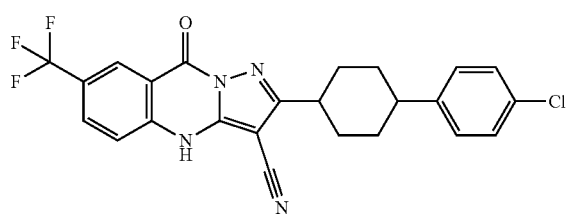 [SMILES: N#Cc1c(C2CCC(c3ccc(Cl)cc3)CC2)nn2c(=O)c3cc(C(F)(F)F)ccc3[nH]c12]

¹H NMR (500 MHz, DMSO-d₆) δ 13.63 (s, 1H), 8.44 (d, J=2.1 Hz, 1H), 8.14 (dd, J=8.7, 2.2 Hz, 1H), 7.73 (d, J=8.8 Hz, 1H), 7.42-7.31 (m, 4H), 2.96 (tt, J=12.1, 3.5 Hz, 1H), 2.65 (ddt, J=12.2, 8.6, 3.8 Hz, 1H), 2.19-2.10 (m, 2H), 1.94 (dd, J=13.3, 3.5 Hz, 2H), 1.80 (qd, J=12.9, 3.2 Hz, 2H), 1.66 (qd, J=12.8, 3.3 Hz, 2H).

Example 16. 2-[1-(4-Chlorophenyl)-4-piperidyl]-9-oxo-7-(trifluoromethyl)-4H-pyrazolo[5,1-b]quinazoline-3-carbonitrile

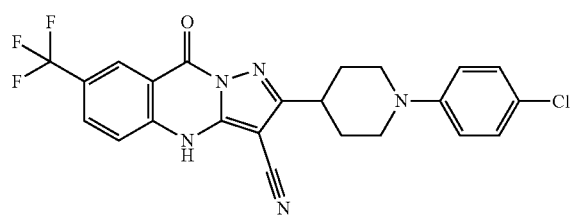 [SMILES: N#Cc1c(C2CCN(c3ccc(Cl)cc3)CC2)nn2c(=O)c3cc(C(F)(F)F)ccc3[nH]c12]

MS m/z: 472 [M+H]⁺.

Example 17. 7-Chloro-2-[4-(4-chlorophenyl)cyclohexyl]-9-oxo-4H-pyrazolo[5,1-b]quinazoline-3-carbonitrile

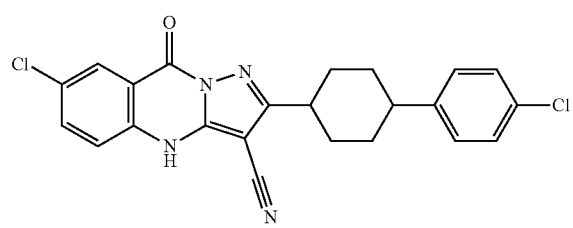 [SMILES: N#Cc1c(C2CCC(c3ccc(Cl)cc3)CC2)nn2c(=O)c3cc(Cl)ccc3[nH]c12]

¹H NMR (500 MHz, DMSO-d₆) δ 13.40 (s, 1H), 8.14 (d, J=2.5 Hz, 1H), 7.87 (dd, J=8.9, 2.5 Hz, 1H), 7.58 (d, J=8.9 Hz, 1H), 7.39-7.31 (m, 4H), 2.94 (tt, J=12.1, 3.5 Hz, 1H), 2.64 (tt, J=12.0, 3.4 Hz, 1H), 2.18-2.08 (m, 2H), 1.98-1.89 (m, 2H), 1.79 (qd, J=12.8, 3.2 Hz, 2H), 1.65 (qd, J=12.8, 3.2 Hz, 2H). MS m/z: 439 [M+H]⁺.

Example 18. 7-Chloro-2-[1-(4-chlorophenyl)cyclopropyl]-9-oxo-4H-pyrazolo[5,1-b]quinazoline-3-carbonitrile

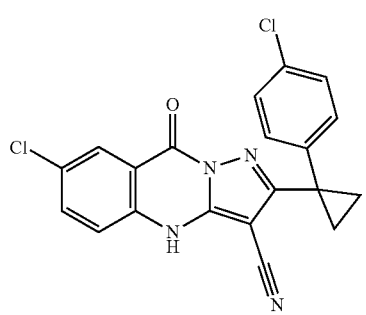 [SMILES: N#Cc1c(C2(c3ccc(Cl)cc3)CC2)nn2c(=O)c3cc(Cl)ccc3[nH]c12]

¹H NMR (500 MHz, DMSO-d₆) δ 13.36 (s, 1H), 8.14 (d, J=2.5 Hz, 1H), 7.87 (dd, J=8.9, 2.5 Hz, 1H), 7.57 (d, J=8.9

Hz, 1H), 7.41-7.36 (m, 2H), 7.33 (d, J=8.6 Hz, 2H), 1.55 (q, J=4.5 Hz, 2H), 1.42 (q, J=4.6 Hz, 2H). MS m/z: 395 [M+H]⁺.

Example 19. 2-[1-(4-Chlorophenyl)cyclopropyl]-7-fluoro-9-oxo-4H-pyrazolo[5,1-b]quinazoline-3-carbonitrile

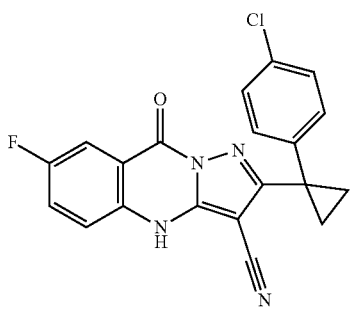 [SMILES: N#Cc1c(C2(c3ccc(Cl)cc3)CC2)nn2c(=O)c3cc(F)ccc3[nH]c12]

¹H NMR (500 MHz, DMSO-d₆) δ 13.31 (s, 1H), 7.91 (dd, J=8.7, 3.0 Hz, 1H), 7.76 (td, J=8.7, 3.0 Hz, 1H), 7.61 (dd, J=9.2, 4.4 Hz, 1H), 7.38 (d, J=8.2 Hz, 2H), 7.33 (d, J=8.3 Hz, 2H), 1.55 (q, J=4.5 Hz, 2H), 1.41 (q, J=4.9, 4.5 Hz, 2H). MS m/z: 379 [M+H]⁺.

Example 20. 7-Chloro-2-[4-(4-chlorophenyl)-1-piperidyl]-9-oxo-4H-pyrazolo[5,1-b]quinazoline-3-carbonitrile

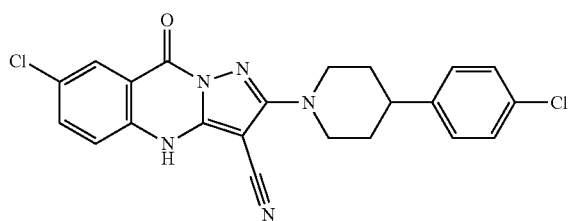

¹H NMR (500 MHz, DMSO-d₆) δ 13.22 (s, 1H), 8.08 (d, J=2.5 Hz, 1H), 7.82 (dd, J=8.9, 2.5 Hz, 1H), 7.58 (d, J=8.9 Hz, 1H), 7.39-7.34 (m, 2H), 7.33-7.28 (m, 2H), 4.23 (ddd, J=13.1, 4.3, 2.2 Hz, 2H), 3.08 (td, J=12.8, 2.5 Hz, 2H), 2.82 (tt, J=12.1, 3.5 Hz, 1H), 1.93-1.82 (m, 2H), 1.73 (qd, J=12.6, 4.0 Hz, 2H). MS m/z: 439 [M+H]⁺.

Example 21. 7-Chloro-2-[1-(4-chlorophenyl)-4-piperidyl]-9-oxo-4H-pyrazolo[5,1-b]quinazoline-3-carbonitrile

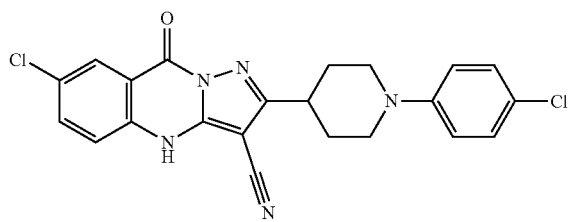 [SMILES: N#Cc1c(C2CCN(c3ccc(Cl)cc3)CC2)nn2c(=O)c3cc(Cl)ccc3[nH]c12]

¹H NMR (500 MHz, DMSO-d₆) δ 13.42 (s, 1H), 8.14 (d, J=2.4 Hz, 1H), 7.87 (dd, J=8.9, 2.5 Hz, 1H), 7.59 (d, J=8.9 Hz, 1H), 7.26-7.19 (m, 2H), 7.05-6.93 (m, 2H), 3.83 (dt, J=12.9, 3.5 Hz, 2H), 3.07 (tt, J=11.6, 3.8 Hz, 1H), 2.89 (td, J=12.4, 2.6 Hz, 2H), 2.08-2.01 (m, 2H), 1.91 (qd, J=12.3, 3.9 Hz, 2H). MS m/z: 438 [M+H]⁺.

Example 22. 7-Bromo-2-[4-(4-chlorophenyl)cyclohexyl]-9-oxo-4H-pyrazolo[5,1-b]quinazoline-3-carbonitrile

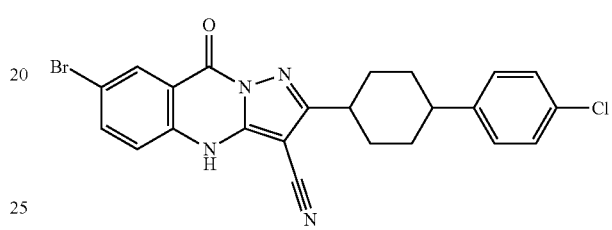

¹H NMR (500 MHz, DMSO-d₆) δ 13.41 (s, 1H), 8.28 (d, J=2.2 Hz, 1H), 7.99 (dd, J=8.9, 2.3 Hz, 1H), 7.53 (d, J=8.8 Hz, 1H), 7.44-7.23 (m, 4H), 2.95 (tt, J=12.0, 3.6 Hz, 1H), 2.66 (tt, J=12.0, 3.5 Hz, 1H), 2.19-2.09 (m, 2H), 1.99-1.91 (m, 2H), 1.81 (qd, J=12.8, 3.2 Hz, 2H), 1.66 (qd, J=12.8, 3.2 Hz, 2H). MS m/z: 481 [M+H]⁺.

Example 23. 7-Chloro-2-[[1-(5-chloropyrimidin-2-yl)-4-piperidyl]oxy]-9-oxo-4H-pyrazolo[5,1-b]quinazoline-3-carbonitrile

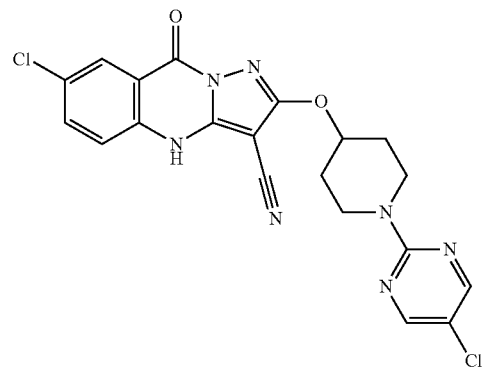 [SMILES: N#Cc1c(OC2CCN(c3ncc(Cl)cn3)CC2)nn2c(=O)c3cc(Cl)ccc3[nH]c12]

¹H NMR (500 MHz, DMSO-d₆) δ 13.46 (s, 1H), 8.44 (s, 2H), 8.11 (d, J=2.5 Hz, 1H), 7.86 (dd, J=8.9, 2.5 Hz, 1H), 7.55 (d, J=8.8 Hz, 1H), 5.20 (tt, J=8.1, 3.8 Hz, 1H), 4.19 (dt, J=13.7, 4.8 Hz, 2H), 3.60 (ddd, J=13.1, 9.1, 3.4 Hz, 2H), 2.15 (dq, J=12.8, 4.7, 4.2 Hz, 2H), 1.76 (dtd, J=12.9, 8.8, 3.9 Hz, 2H). MS m/z: 456 [M+H]⁺.

Example 24. 7-Chloro-2-[[1-(4-chlorobenzoyl)-4-piperidyl]oxy]-9-oxo-4H-pyrazolo[5,1-b]quinazoline-3-carbonitrile

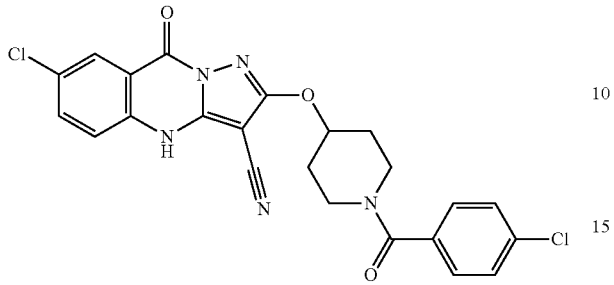

$^1$H NMR (500 MHz, DMSO-$d_6$) δ 13.46 (s, 1H), 8.11 (d, J=2.4 Hz, 1H), 7.86 (dd, J=8.8, 2.6 Hz, 1H), 7.60-7.43 (m, 5H), 5.19 (tt, J=8.3, 3.9 Hz, 1H), 4.03 (s, 1H), 3.63-3.46 (m, 3H), 2.27-2.03 (m, 2H), 1.80 (s, 2H). MS m/z: 482 [M+H]$^+$.

Example 25. 7-Chloro-2-[[1-(5-chloro-2-pyridyl)-4-piperidyl]oxy]-9-oxo-4H-pyrazolo[5,1-b]quinazoline-3-carbonitrile

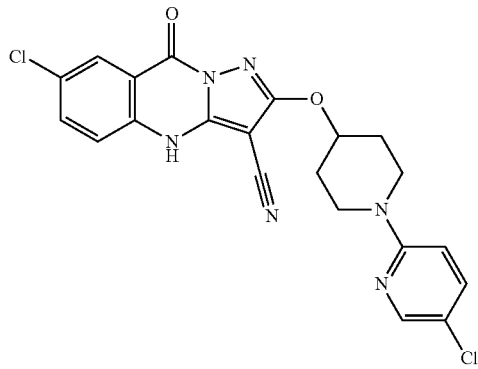 [SMILES: N#Cc1c(OC2CCN(c3ccc(Cl)cn3)CC2)nn2c(=O)c3cc(Cl)ccc3[nH]c12]

$^1$H NMR (500 MHz, DMSO-$d_6$) δ 8.05 (d, J=73.0 Hz, 2H), 7.81-7.28 (m, 3H), 6.95 (d, J=9.2 Hz, 1H), 5.15 (s, 1H), 4.29-3.72 (m, 2H), 3.33 (s, 2H), 2.13 (s, 2H), 1.88-1.54 (m, 2H). MS m/z: 455 [M+H]$^+$.

4. Formation of General Formula II Tricycle—Method D

Some compounds of the general formula II are synthesized by employing the reaction between 3-amino-2-thioxo-2,3-dihydroquinazolin-4(1H)-ones and various α-bromo, β-keto amides:

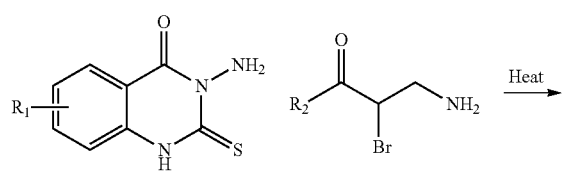

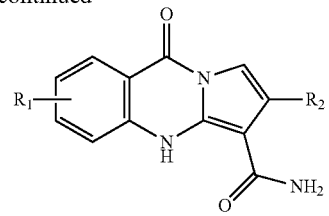

Example 26. 2-[4-(4-Chlorophenyl)cyclohexyl]-9-oxo-4H-pyrazolo[5,1-b]quinazoline-3-carboxamide

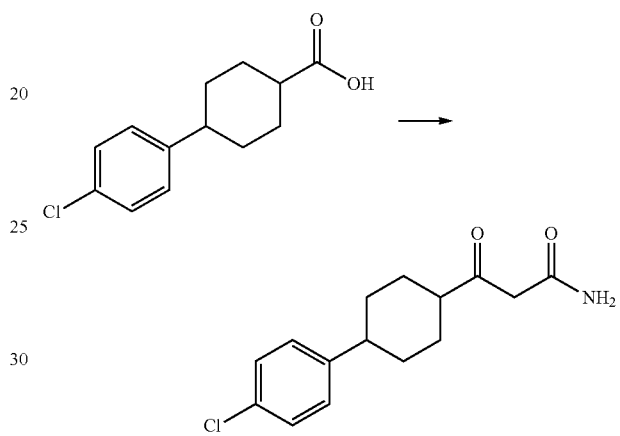

To a solution of 4-(4-chlorophenyl)cyclohexanecarboxylic acid (2.50 g, 10.5 mmol) in CH$_2$Cl$_2$ (30.0 mL) were added DMF (23.0 mg, 314.2 μmol) and oxalyl dichloride (2.79 g, 22.0 mmol) at room temperature. The mixture was stirred at room temperature for 14.5 h. The reaction mixture was concentrated under reduced pressure to give 4-(4-chlorophenyl)cyclohexanecarbonyl chloride (2.69 g). A solution of crude acid chloride (2.69 g) in CH$_2$Cl$_2$ (10 mL) was added to a solution of 2,2-dimethyl-1,3-dioxane-4,6-dione (1.66 g, 11.6 mmol) and pyridine (1.66 g, 21.0 mmol) in CH$_2$Cl$_2$ (20 mL) at 0° C. The mixture was stirred at 0° C. for 10 min and at room temperature for 1.5 h. The reaction mixture was partitioned between CH$_2$Cl$_2$ and 1N HCl aqueous solution. The organic layer was washed with brine, dried over Na$_2$SO$_4$, filtered and concentrated under reduced pressure. The residue was purified by column chromatography (silica gel, hexane/EtOAc) to give a mixture contained 5-[4-(4-chlorophenyl)cyclohexanecarbonyl]-2,2-dimethyl-1,3-dioxane-4,6-dione (2.71 g). The mixture of 5-[4-(4-chlorophenyl)cyclohexanecarbonyl]-2,2-dimethyl-1,3-dioxane-4,6-dione (2.70 g) and tert-butyl carbamate (1.04 g, 8.88 mmol) in acetonitrile (50.0 mL) was stirred at 90° C. for 35 min. The reaction mixture was concentrated under reduced pressure. The residue was purified by column chromatography (silica gel, hexane/EtOAc) to give a mixture contained tert-butyl N-[3-[4-(4-chlorophenyl)cyclohexyl]-3-oxo-propanoyl]carbamate (1.82 g) as a white solid. This product was used next step without further purification. TFA (5.0 mL) was added to a solution of tert-butyl N-[3-[4-(4-chlorophenyl)cyclohexyl]-3-oxo-propanoyl]carbamate (1.81 g) in CH$_2$Cl$_2$ (30.0 mL) at room temperature. The reaction mixture was stirred at room temperature for 14.5 h. The reaction mixture was concentrated under reduced pressure. The residue was purified by column chromatography (basic silica gel, CH$_2$Cl$_2$/MeOH) and by washed with ethyl acetate and IPE to give 3-[4-(4-chlorophenyl)cyclohexyl]-3-oxo-propanamide (330.0 mg, 1.18 mmol, 25% yield) as white solid. $^1$H NMR (500 MHz, Chloroform-d) δ 7.26 (tt, J=3.0, 1.3 Hz, 2H), 7.14-7.10 (m, 2H), 6.99 (s, 1H), 5.45 (s, 1H), 3.50 (s, 2H), 2.50 (dtd, J=14.9, 11.2, 3.4 Hz, 2H), 2.09-1.97 (m, 4H), 1.53-1.44 (m, 4H), CO$_2$H was not detected. MS m/z: 280 [M+H]$^+$.

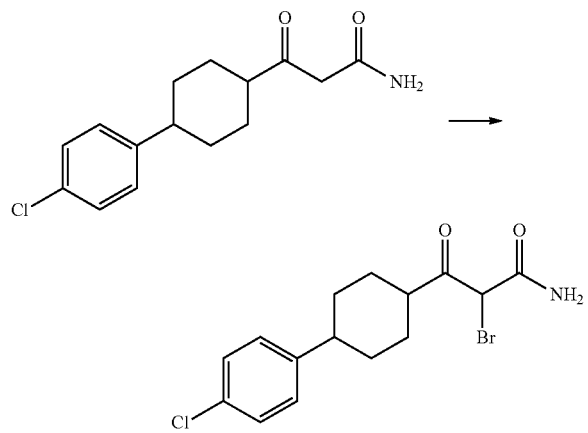

The mixture of 3-[4-(4-chlorophenyl)cyclohexyl]-3-oxo-propanamide (327.0 mg, 1.17 mmol), NBS (208.2 mg, 1.17 mmol), and sulfooxysodium (35.1 mg, 293 µmol) in THF (20.0 mL) was stirred at room temperature for 2 h. The reaction mixture was partitioned between ethyl acetate and sodium hydrogen carbonate aqueous solution. The organic layer was washed with brine, dried over Na$_2$SO$_4$, filtered and concentrated under reduced pressure to give 2-bromo-3-[4-(4-chlorophenyl)cyclohexyl]-3-oxo-propanamide (500.0 mg, 1.16 mmol, 99% yield) as white solids. $^1$H NMR (500 MHz, Chloroform-d) δ 7.29-7.24 (m, 2H), 7.14-7.10 (m, 2H), 6.61 (s, 1H), 5.64 (s, 1H), 4.89 (d, J=1.3 Hz, 1H), 2.89-2.81 (m, 1H), 2.54-2.46 (m, 1H), 2.11 (t, J=12.0 Hz, 2H), 2.02-1.97 (m, 2H), 1.65-1.44 (m, 4H). MS m/z: 358 [M+H]$^+$.

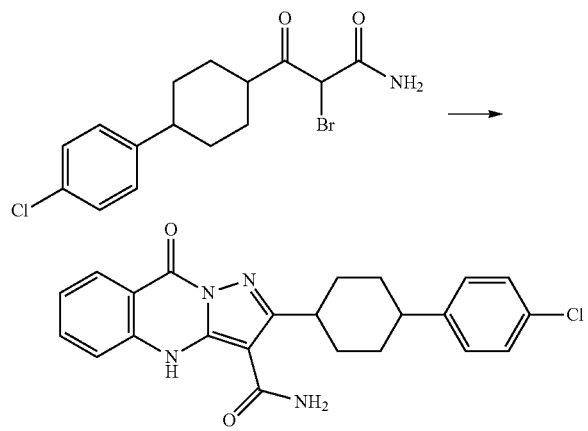

The mixture of 3-amino-2-thioxo-1H-quinazolin-4-one (100.0 mg, 518 µmol) and 2-bromo-3-[4-(4-chlorophenyl)cyclohexyl]-3-oxo-propanamide (259.9 mg, 724 µmol) in IPA (12.0 mL) was stirred at 100° C. for 7 days. The reaction mixture was cooled to room temperature. The reaction mixture was concentrated under reduced pressure. The residue was washed with IPA and dried over to give 2-[4-(4-chlorophenyl)cyclohexyl]-9-oxo-4H-pyrazolo[5,1-b]quinazoline-3-carboxamide (102.0 mg, 242 µmol, 47% yield) as light yellow amorphous solid. $^1$H NMR (500 MHz, DMSO-d$_6$) δ 11.66 (s, 1H), 8.20 (d, J=8.0 Hz, 1H), 7.92 (d, J=8.4 Hz, 1H), 7.78 (t, J=7.9 Hz, 1H), 7.40-7.21 (m, 7H), 2.63 (d, J=11.6 Hz, 1H), 2.13 (d, J=12.3 Hz, 2H), 1.90 (d, J=12.2 Hz, 2H), 1.79-1.64 (m, 4H), 1H was buried with DMSO. MS m/z: 421 [M+H]$^+$.

Example 27. 2-[4-(4-Chlorophenyl)cyclohexyl]-9-oxo-4H-pyrazolo[5,1-b]quinazoline-3-carbonitrile

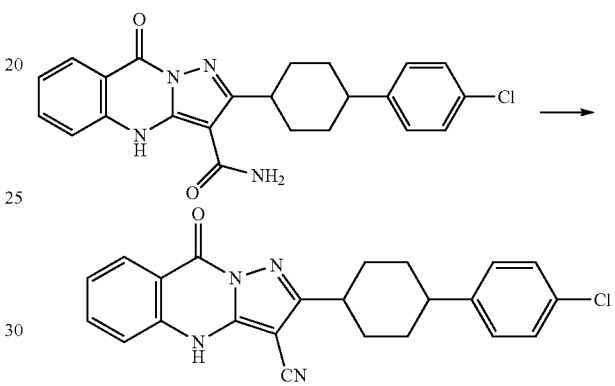

Thionyl chloride (77.7 mg, 653 µmol) was added to a suspension of 2-[4-(4-chlorophenyl)cyclohexyl]-9-oxo-4H-pyrazolo[5,1-b]quinazoline-3-carboxamide (55.0 mg, 131 µmol) in DMF (3.0 mL) at 0° C. The mixture was stirred at 0° C. for 5 h. As the reaction was not completed, thionyl chloride (155 mg, 1.31 mmol) was added at 0° C. The mixture was stirred at room temperature for 23 h. The reaction mixture was quenched with saturated sodium hydrogen carbonate aqueous solution at 0° C. The reaction mixture was partitioned between ethyl acetate and water. The organic layer was washed with brine, dried over Na$_2$SO$_4$, filtered and concentrated under reduced pressure. The residue was washed with ethyl acetate to give 2-[4-(4-chlorophenyl)cyclohexyl]-9-oxo-4H-pyrazolo[5,1-b]quinazoline-3-carbonitrile (36.2 mg, 89.9 µmol, 69% yield) as light yellow amorphous solid. $^1$H NMR (500 MHz, DMSO-d$_6$) δ 13.27 (s, 1H), 8.24 (d, J=8.0 Hz, 1H), 7.86 (t, J=7.8 Hz, 1H), 7.60 (d, J=8.4 Hz, 1H), 7.44-7.35 (m, 5H), 2.96 (s, 1H), 2.67 (d, J=3.7 Hz, 1H), 2.17-2.11 (m, 2H), 2.00-1.94 (m, 2H), 1.87-1.78 (m, 2H), 1.73-1.63 (m, 2H). MS m/z: 403 [M+H]$^+$.

Example 28. 2-[3-(4-Chlorophenoxy)propyl]-9-oxo-4H-pyrazolo[5,1-b]quinazoline-3-carboxamide

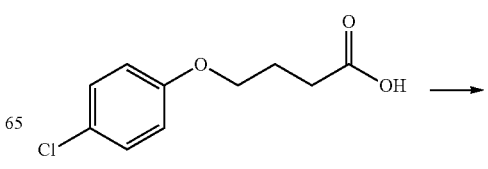

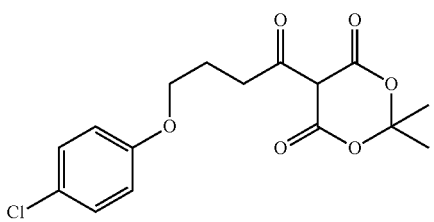

To a solution of 4-(4-chlorophenoxy)butanoic acid (2.00 g, 9.32 mmol) in CH$_2$Cl$_2$ (30.0 mL) were added DMF (20.4 mg, 280 µmol) and oxalyl dichloride (2.48 g, 19.6 mmol) at room temperature. The mixture was stirred at room temperature for 1 h. The reaction mixture was concentrated under reduced pressure to give crude 4-(4-chlorophenoxy)butanoyl chloride (2.17 g) as oil. A solution of crude acid chloride (2.17 g) in CH$_2$Cl$_2$ (10 mL) was added to a solution of 2,2-dimethyl-1,3-dioxane-4,6-dione (1.48 g, 10.3 mmol) and pyridine (1.47 g, 18.6 mmol) in CH$_2$Cl$_2$ (25 mL) at 0° C. The mixture was stirred at 0° C. for 5 min and at room temperature for 2.5 h. The reaction mixture was partitioned between CH$_2$Cl$_2$ and 0.5 N HCl aqueous solution. The organic layer was washed with brine, dried over Na$_2$SO$_4$, filtered and concentrated under reduced pressure. The residue was purified by column chromatography (silica gel, hexane/EtOAc) to give 5-[4-(4-chlorophenoxy)butanoyl]-2,2-dimethyl-1,3-dioxane-4,6-dione (2.15 g, 6.31 mmol, 68% yield) as light yellow solids. $^1$H NMR (500 MHz, Chloroform-d) δ 7.25-7.19 (m, 2H), 6.83-6.77 (m, 2H), 4.04 (t, J=6.0 Hz, 2H), 3.29 (t, J=7.4 Hz, 2H), 2.26-2.16 (m, 2H), 1.72 (d, J=1.2 Hz, 6H), 1H was not detected.

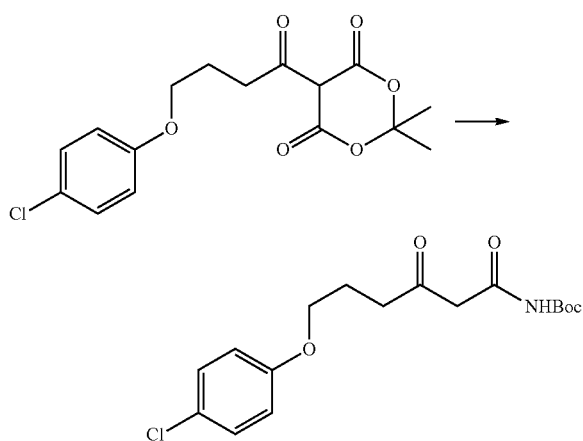 [SMILES: CC1(C)OC(=O)C(C(=O)CCCOc2ccc(Cl)cc2)C(=O)O1 ; CC(C)(C)OC(=O)NC(=O)CC(=O)CCCOc1ccc(Cl)cc1]

The mixture of 5-[4-(4-chlorophenoxy)butanoyl]-2,2-dimethyl-1,3-dioxane-4,6-dione (2.14 g, 6.28 mmol) and tert-butyl carbamate (882.8 mg, 7.54 mmol) in acetonitrile (30.0 mL) was stirred at 95° C. for 1 h. The reaction mixture was concentrated under reduced pressure. The residue was purified by column chromatography (silica gel, hexane/EtOAc) to give tert-butyl N-[6-(4-chlorophenoxy)-3-oxo-hexanoyl]carbamate (2.06 g, 5.79 mmol, 92% yield) as light yellow solid. $^1$H NMR (500 MHz, Chloroform-d) δ 7.55 (s, 1H), 7.24-7.16 (m, 2H), 6.84-6.79 (m, 2H), 4.44 (s, 1H), 3.96 (t, J=6.4 Hz, 2H), 3.89 (s, 1H), 2.76 (dd, J=7.8, 6.3 Hz, 2H), 2.10 (h, J=7.2 Hz, 2H), 1.44 (s, 9H).

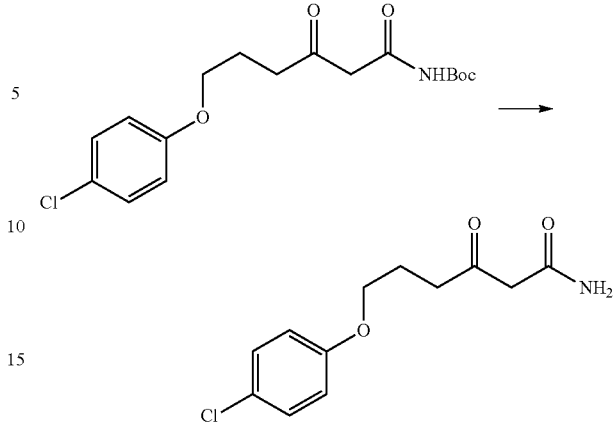

TFA (5.0 mL) was added to a solution of tert-butyl N-[6-(4-chlorophenoxy)-3-oxo-hexanoyl]carbamate (2.05 g, 5.76 mmol) in CH$_2$Cl$_2$ (30.0 mL) at room temperature. The mixture was stirred at room temperature for 45 min. The reaction mixture was concentrated under reduced pressure. The residue was purified column chromatography (silica gel, hexane/EtOAc) and by recrystallization from ethyl acetate and IPE to give 6-(4-chlorophenoxy)-3-oxo-hexanamide (953.0 mg, 3.73 mmol, 65% yield) as white solids. $^1$H NMR (500 MHz, Chloroform-d) δ 7.24-7.18 (m, 2H), 6.86 (d, J=40.1 Hz, 1H), 6.81-6.75 (m, 2H), 5.45 (s, 1H), 3.95 (td, J=6.0, 1.8 Hz, 2H), 3.47 (d, J=1.8 Hz, 2H), 2.77 (td, J=7.1, 1.7 Hz, 2H), 2.09 (qd, J=6.9, 3.4 Hz, 2H). MS m/z: 256 [M+H]$^+$.

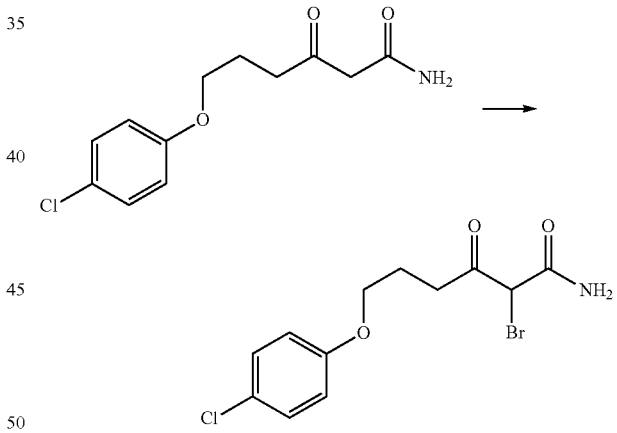

The mixture of 6-(4-chlorophenoxy)-3-oxo-hexanamide (950.0 mg, 3.72 mmol), NBS (793.5 mg, 4.46 mmol) and sodium sulfite (111.5 mg, 928 µmol) in THF (15.0 mL) was stirred at room temperature for 25 min. The reaction mixture was partitioned between ethyl acetate and sodium hydrogen carbonate aqueous solution. The organic layer was washed with sodium hydrogen carbonate aqueous solution and brine, dried over Na$_2$SO$_4$, filtered and concentrated under reduced pressure. The solid residue was recrystallization from ethyl acetate and IPE to give 2-bromo-6-(4-chlorophenoxy)-3-oxo-hexanamide (909 mg, 2.72 mmol, 73% yield) as white solid. $^1$H NMR (500 MHz, Chloroform-d) δ 7.23-7.19 (m, 2H), 6.83-6.79 (m, 2H), 6.64-6.43 (m, 1H), 5.64 (s, 1H), 4.79 (d, J=1.5 Hz, 1H), 3.96 (t, J=6.1 Hz, 2H), 3.01-2.96 (m, 2H), 2.13 (p, J=6.5 Hz, 2H). MS m/z: 334 [M+H]$^+$.

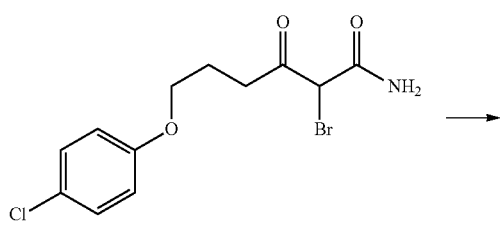

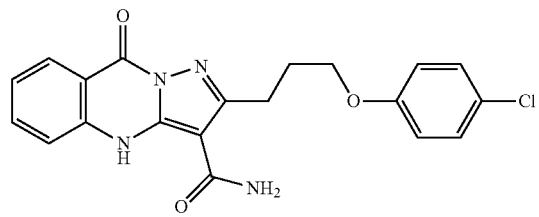

The mixture of 3-amino-2-thioxo-1H-quinazolin-4-one (100.0 mg, 517.5 μmol) and 2-bromo-6-(4-chlorophenoxy)-3-oxo-hexanamide (207.8 mg, 621 μmol) in IPA (10.0 mL) was stirred at 95° C. for 17 h. The reaction mixture was cooled to room temperature. The solid residue was filtered, washed with IPA and dried over to give 2-[3-(4-chlorophenoxy)propyl]-9-oxo-4H-pyrazolo[5,1-b]quinazoline-3-carboxamide (155.0 mg, 391 μmol, 75% yield) as white solids. $^1$H NMR (500 MHz, DMSO-d$_6$) δ 11.68 (s, 1H), 8.20 (d, J=8.1 Hz, 1H), 7.95 (d, J=8.4 Hz, 1H), 7.78 (t, J=7.8 Hz, 1H), 7.54-7.07 (m, 3H+br, 2H), 7.02-6.98 (m, 2H), 4.09 (t, J=6.4 Hz, 2H), 3.11 (t, J=7.5 Hz, 2H), 2.19 (t, J=7.1 Hz, 2H). MS m/z: 397 [M+H]$^+$.

Example 29. 2-[3-(4-Chlorophenoxy)propyl]-9-oxo-4H-pyrazolo[5,1-b]quinazoline-3-carbonitrile

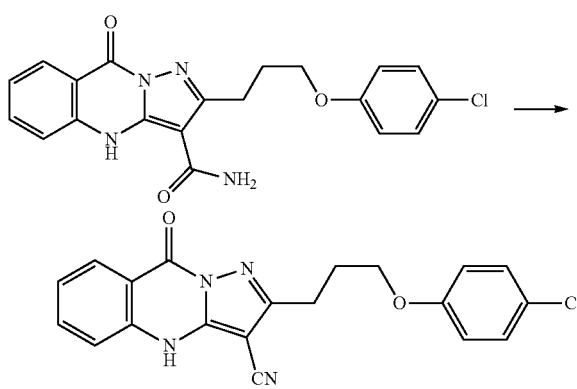

Thionyl chloride (76.2 mg, 640 μmol) was added to a suspension of 2-[3-(4-chlorophenoxy)propyl]-9-oxo-4H-pyrazolo[5,1-b]quinazoline-3-carboxamide (50.8 mg, 128 mol) in DMF (3.0 mL) at 0° C. The mixture was stirred at room temperature for 5 h. The reaction mixture was quenched with saturated sodium hydrogen carbonate aqueous solution at 0° C. The reaction mixture was partitioned between ethyl acetate and water. The organic layer was washed with brine, dried over Na$_2$SO$_4$, filtered and concentrated under reduced pressure. The residue was purified by recrystallization from ethyl acetate to give 2-[3-(4-chlorophenoxy)propyl]-9-oxo-4H-pyrazolo[5,1-b]quinazoline-3-carbonitrile (22.4 mg, 59.1 mol, 46% yield) as white solids. $^1$H NMR (500 MHz, DMSO-d$_6$) δ 13.26 (s, 1H), 8.22 (d, J=8.0 Hz, 1H), 7.84 (t, J=7.8 Hz, 1H), 7.56 (d, J=8.3 Hz, 1H), 7.39 (t, J=7.7 Hz, 1H), 7.31 (d, J=8.3 Hz, 2H), 6.98 (d, J=8.3 Hz, 2H), 4.08 (t, J=6.3 Hz, 2H), 2.94 (t, J=7.5 Hz, 2H), 2.19 (t, J=7.0 Hz, 2H). MS m/z: 379 [M+H]$^+$. Mp. 263-265° C.

Example 30. 2-[1-(4-Chlorophenyl)cyclopropyl]-9-oxo-4H-pyrazolo[5,1-b]quinazoline-3-carboxamide

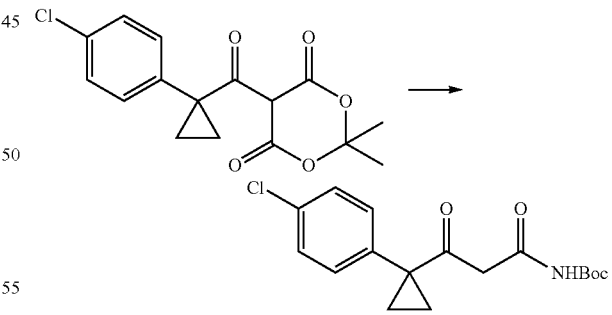

To a solution of 1-(4-chlorophenyl)cyclopropanecarboxylic acid (2.00 g, 10.2 mmol) in DMA (20.0 mL) were added 2,2-dimethyl-1,3-dioxane-4,6-dione (1.76 g, 12.2 mmol), 1-(3-dimethylaminopropyl)-3-ethylcarbodiimide hydrochloride (2.92 g, 15.3 mmol) and DMAP (1.86 g, 15.3 mmol) at room temperature. The mixture was stirred at room temperature for 19 h. The mixture was diluted with 1N HCl and extracted with EtOAc. The combined organic layer was washed with brine, dried over MgSO$_4$, filtered and concentrated in vacuo. The residue was purified by column chromatography (silica gel, hexane/EtOAc) to give 5-[1-(4-chlorophenyl)cyclopropanecarbonyl]-2,2-dimethyl-1,3-dioxane-4,6-dione (1.84 g, 5.70 mmol, 56% yield) as colorless solid. $^1$H NMR (500 MHz, Chloroform-d) δ 15.53 (s, 1H), 7.38 (d, J=8.0 Hz, 2H), 7.28 (d, J=7.7 Hz, 2H), 1.65 (d, J=1.5 Hz, 6H), 1.58 (s, 2H), 1.47 (d, J=5.7 Hz, 2H). MS m/z: 321 [M−H]$^−$.

The mixture of 5-[1-(4-chlorophenyl)cyclopropanecarbonyl]-2,2-dimethyl-1,3-dioxane-4,6-dione (2.70 g, 8.37 mmol), tert-butyl carbamate (1.18 g, 10.0 mmol), and acetonitrile (50.0 mL) was stirred at 90° C. for 1 h. The reaction mixture was concentrated under reduced pressure. The residue was purified by column chromatography (silica gel, hexane/EtOAc) to give tert-butyl N-[3-[1-(4-chlorophenyl)cyclopropyl]-3-oxo-propanoyl]carbamate (1.95 g, 5.77 mmol, 69% yield) as pale yellow oil. $^1$H NMR (500 MHz, Chloroform-d) δ 7.52 (s, 1H), 7.42 (d, J=7.9 Hz, 2H), 7.37

(d, J=7.8 Hz, 2H), 3.73 (s, 2H), 1.74-1.70 (m, 2H), 1.50 (s, 9H), 1.27-1.23 (m, 2H). MS m/z: 336 [M−H]

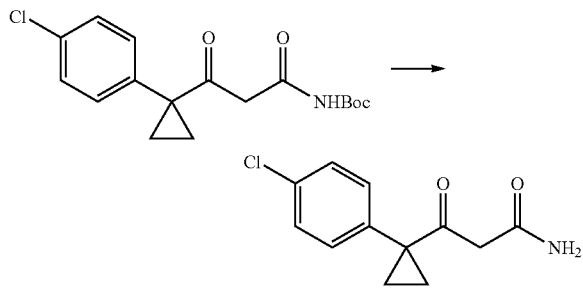 [SMILES: CC(C)(C)OC(=O)NC(=O)CC(=O)C1(c2ccc(Cl)cc2)CC1 ; NC(=O)CC(=O)C1(c2ccc(Cl)cc2)CC1]

TFA (6.17 g, 54.1 mmol) was added to a solution of tert-butyl N-[3-[1-(4-chlorophenyl)cyclopropyl]-3-oxo-propanoyl]carbamate (1.95 g, 5.77 mmol) in CH$_2$Cl$_2$ (30.0 mL) at room temperature. The mixture was stirred at room temperature for 2 h. The reaction mixture was concentrated under reduced pressure. The residue was purified by column chromatography (silica gel, hexane/EtOAc) to give 3-[1-(4-chlorophenyl)cyclopropyl]-3-oxo-propanamide (1.07 g, 4.50 mmol, 78% yield) as pink solid. $^1$H NMR (500 MHz, Chloroform-d) δ 7.38 (d, J=8.0 Hz, 2H), 7.31 (d, J=8.0 Hz, 2H), 7.11 (s, 1H), 5.46 (s, 1H), 3.32 (s, 2H), 1.74 (s, 2H), 1.31 (s, 2H). MS m/z: 238 [M+H]$^+$.

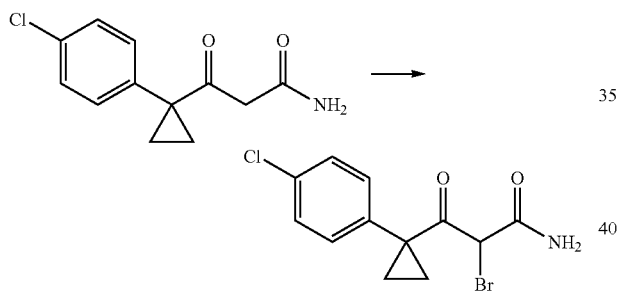

NBS (801 mg, 4.50 mmol) was added to a solution of 3-[1-(4-chlorophenyl)cyclopropyl]-3-oxo-propanamide (1.07 g, 4.50 mmol) and sodium bisulfate (135 mg, 1.13 mmol) in THF (20.0 mL) at 0° C. The mixture was stirred at 0° C. for 1 h. The mixture was quenched with sat. NaHCO$_3$aq. and extracted with EtOAc. The organic layer was washed with brine, dried over MgSO$_4$, filtered and concentrated under reduced pressure to give 2-bromo-3-[1-(4-chlorophenyl)cyclopropyl]-3-oxo-propanamide (1.46 g, 4.50 mmol, 100% yield) as light orange solid. $^1$H NMR (500 MHz, Chloroform-d) δ 7.44 (d, J=7.4 Hz, 2H), 7.38 (d, J=7.2 Hz, 2H), 6.69 (s, 1H), 5.72 (s, 1H), 4.72 (s, 1H), 1.84 (d, J=4.4 Hz, 2H), 1.51-1.43 (m, 1H), 1.38-1.28 (m, 1H). MS m/z: 316 [M+H]$^+$.

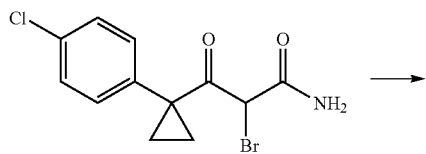

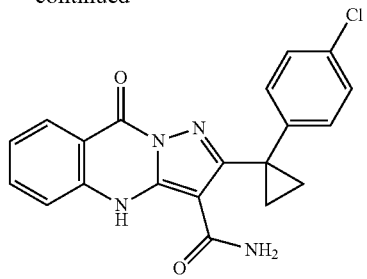

The mixture of 3-amino-2-thioxo-1H-quinazolin-4-one (100.0 mg, 518 μmol) and 2-bromo-3-[1-(4-chlorophenyl)cyclopropyl]-3-oxo-propanamide (163.8 mg, 518 μmol) in IPA (5.0 mL) was stirred at 95° C. for 6 days. The reaction mixture was cooled to room temperature. The precipitate was filtered, washed with IPA and dried over to give 2-[1-(4-chlorophenyl)cyclopropyl]-9-oxo-4H-pyrazolo[5,1-b]quinazoline-3-carboxamide (57.6 mg, 152 μmol, 29% yield) as pale yellow solid. $^1$H NMR (500 MHz, DMSO-d$_6$) δ 11.76 (s, 1H), 8.25 (d, J=8.0 Hz, 1H), 8.07 (d, J=8.4 Hz, 1H), 7.82 (t, J=7.6 Hz, 1H), 7.49 (s, 1H), 7.41-7.33 (m, 3H), 7.19-7.11 (m, 2H), 5.98 (s, 1H), 1.68-1.63 (m, 2H), 1.62-1.57 (m, 2H). MS m/z: 379 [M+H]$^+$.

Example 31. 2-[1-(4-Chlorophenyl)cyclopropyl]-9-oxo-4H-pyrazolo[5,1-b]quinazoline-3-carbonitrile To a solution of 2-[1-(4-chlorophenyl)cyclopropyl]-9-oxo-4H-pyrazolo[5,1-b]quinazoline-3-carboxamide (40.2 mg, 106 mmol) in DMF (3.0 mL) was added SOCl$_2$ (63.1 mg, 531 mmol) at 0° C. The mixture was stirred at 0° C. for 2 h. The mixture was quenched with sat NaHCO$_3$aq. The mixture was diluted with water and extracted with EtOAc. The combined organic layer was washed with brine, dried over MgSO$_4$, filtered and concentrated in vacuo. The residue was purified by column chromatography (silica gel, hexane/EtOAc). The solid was washed with EtOAc-hexane to give 2-[1-(4-chlorophenyl)cyclopropyl]-9-oxo-4H-pyrazolo[5,1-b]quinazoline-3-carbonitrile (29.6 mg, 82.0 mmol, 77% yield) as colorless solid. $^1$H NMR (500 MHz, DMSO-d$_6$) δ 13.22 (s, 1H), 8.24 (d, J=8.1 Hz, 1H), 7.86 (t, J=7.5 Hz, 1H), 7.58 (d, J=8.3 Hz, 1H), 7.41 (d, J=7.6 Hz, 3H), 7.35 (d, J=7.4 Hz, 2H), 1.58 (s, 2H), 1.43 (s, 2H). MS m/z: 361 [M+H]⁺.

Other examples shown below were synthesized using method D:

Example 32. 2-(2,4-Dichlorophenyl)-9-oxo-4H-pyrazolo[5,1-b]quinazoline-3-carboxamide

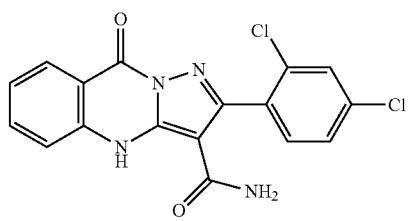 [SMILES: NC(=O)c1c(-c2ccc(Cl)cc2Cl)nn2c(=O)c3ccccc3[nH]c12]

¹H NMR (500 MHz, DMSO-d₆) δ 11.93 (s, 1H), 8.27 (d, J=8.2 Hz, 1H), 8.05 (d, J=8.4 Hz, 1H), 7.90-7.79 (m, 2H), 7.64 (s, 2H), 7.40 (t, J=7.5 Hz, 1H). MS m/z: 373 [M+H]⁺.

Example 33. 2-(2,4-Dichlorophenyl)-9-oxo-4H-pyrazolo[5,1-b]quinazoline-3-carbonitrile

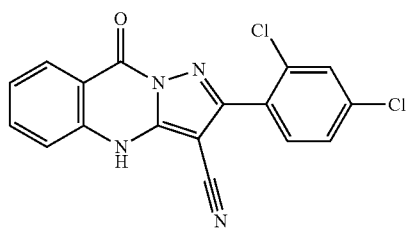 [SMILES: N#Cc1c(-c2ccc(Cl)cc2Cl)nn2c(=O)c3ccccc3[nH]c12]

¹H NMR (500 MHz, DMSO-d₆) δ 13.51 (s, 1H), 8.29 (dd, J=8.1, 1.4 Hz, 1H), 7.94 (d, J=1.7 Hz, 1H), 7.93-7.89 (m, 1H), 7.71-7.67 (m, 2H), 7.65 (d, J=8.3 Hz, 1H), 7.47 (t, J=7.6 Hz, 1H). MS m/z: 353 [M+H]⁺.

Example 34. 6-Chloro-2-(2,4-dichlorophenyl)-9-oxo-4H-pyrazolo[5,1-b]quinazoline-3-carboxamide

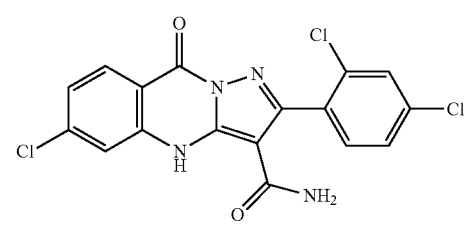 [SMILES: NC(=O)c1c(-c2ccc(Cl)cc2Cl)nn2c(=O)c3ccc(Cl)cc3[nH]c12]

¹H NMR (500 MHz, DMSO-d6) δ 12.02 (s, 1H), 8.25 (d, J=8.6 Hz, 1H), 8.17 (s, 1H), 7.85 (s, 1H), 7.63 (s, 2H), 7.42 (d, J=8.4 Hz, 2H), 6.04 (s, 1H). MS m/z: 407 [M+H]⁺.

Example 35. 6-Chloro-2-(2,4-dichlorophenyl)-9-oxo-4H-pyrazolo[5,1-b]quinazoline-3-carbonitrile

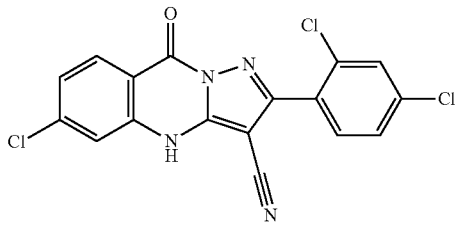 [SMILES: N#Cc1c(-c2ccc(Cl)cc2Cl)nn2c(=O)c3ccc(Cl)cc3[nH]c12]

¹H NMR (500 MHz, DMSO-d6) δ 13.57 (s, 1H), 8.27 (d, J=8.7 Hz, 1H), 7.94 (s, 1H), 7.68 (s, 2H), 7.62 (d, J=1.8 Hz, 1H), 7.46 (d, J=8.3 Hz, 1H). MS m/z: 389 [M+H]⁺.

Example 36. 2-(2,4-Dichlorophenyl)-5-methoxy-9-oxo-4H-pyrazolo[5,1-b]quinazoline-3-carbonitrile

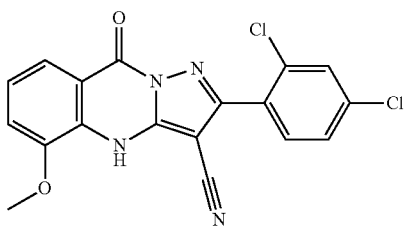 [SMILES: COc1cccc2c(=O)n3nc(-c4ccc(Cl)cc4Cl)c(C#N)c3[nH]c12]

¹H NMR (500 MHz, DMSO-d6) δ 13.15 (s, 1H), 7.93 (s, 1H), 7.84 (d, J=8.0 Hz, 1H), 7.67 (s, 2H), 7.53 (s, 1H), 7.41 (s, 1H), 4.06 (s, 3H). MS m/z: 385 [M+H]⁺.

Example 37. 2-(2,4-Dichlorophenyl)-8-methoxy-9-oxo-4H-pyrazolo[5,1-b]quinazoline-3-carbonitrile

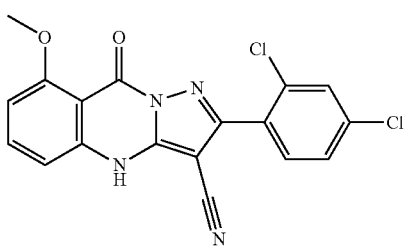 [SMILES: COc1cccc2[nH]c3c(C#N)c(-c4ccc(Cl)cc4Cl)nn3c(=O)c12]

¹H NMR (500 MHz, DMSO-d6) δ 13.24 (s, 1H), 7.92 (s, 1H), 7.76 (t, J=8.1 Hz, 1H), 7.67 (s, 2H), 7.14 (d, J=8.3 Hz, 1H), 6.95 (d, J=7.7 Hz, 1H), 3.95 (s, 3H). MS m/z: 385 [M+H]⁺.

Example 38. 6-Chloro-2-(2,4-dichlorophenyl)-5-methoxy-9-oxo-4H-pyrazolo[5,1-b]quinazoline-3-carbonitrile

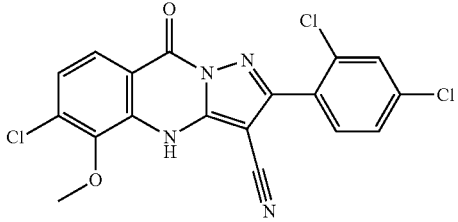 [SMILES: COc1c(Cl)ccc2c(=O)n3nc(-c4ccc(Cl)cc4Cl)c(C#N)c3[nH]c12]

¹H NMR (500 MHz, Chloroform-d) δ 9.35 (s, 1H), 8.19 (d, J=8.8 Hz, 1H), 7.65-7.59 (m, 2H), 7.46-7.40 (m, 2H), 4.19 (s, 3H). MS m/z: 419 [M+H]⁺.

Example 39. 2-(2,4-Dichlorophenyl)-7-methoxy-9-oxo-4H-pyrazolo[5,1-b]quinazoline-3-carboxamide

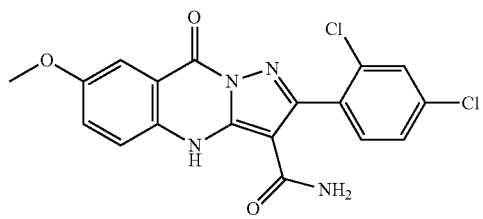 [SMILES: COc1ccc2[nH]c3c(C(N)=O)c(-c4ccc(Cl)cc4Cl)nn3c(=O)c2c1]

¹H NMR (500 MHz, DMSO-d6) δ 11.91 (s, 1H), 8.03 (d, J=9.2 Hz, 1H), 7.85 (s, 1H), 7.64 (s, 3H), 7.52 (dd, J=9.0, 2.5 Hz, 1H), 7.19 (s, 1H), 5.91 (s, 1H), 3.90 (s, 3H). MS m/z: 403 [M+H]⁺.

Example 40. 2-(2,4-Dichlorophenyl)-7-methoxy-9-oxo-4H-pyrazolo[5,1-b]quinazoline-3-carbonitrile

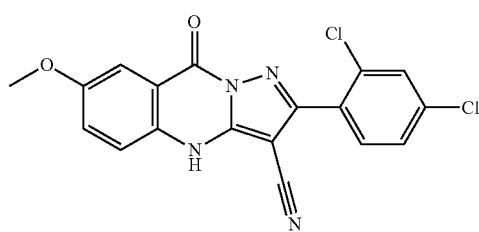 [SMILES: COc1ccc2[nH]c3c(C#N)c(-c4ccc(Cl)cc4Cl)nn3c(=O)c2c1]

¹H NMR (500 MHz, DMSO-d6) δ 13.46 (s, 1H), 7.93 (s, 1H), 7.71-7.63 (m, 3H), 7.61 (d, J=9.0 Hz, 1H), 7.58-7.53 (m, 1H), 3.91 (s, 3H). MS m/z: 385 [M+H]⁺.

Example 41. 2-[(4-Chlorophenoxy)methyl]-9-oxo-4H-pyrazolo[5,1-b]quinazoline-3-carboxamide

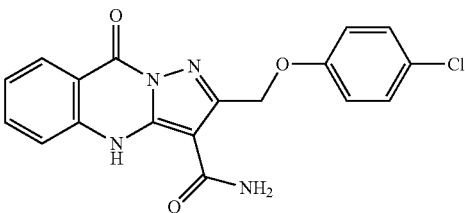 [SMILES: NC(=O)c1c(COc2ccc(Cl)cc2)nn2c(=O)c3ccccc3[nH]c12]

¹H NMR (500 MHz, DMSO-d₆) δ 11.82 (s, 1H), 8.22 (d, J=8.0 Hz, 1H), 8.00 (d, J=8.5 Hz, 1H), 7.81 (t, J=7.8 Hz, 1H), 7.37 (dd, J=7.9, 5.3 Hz, 3H), 7.14 (d, J=8.6 Hz, 2H), 5.45 (s, 2H), 2H were detected as broad peaks. MS m/z: 369 [M+H]⁺.

Example 42. 2-[(4-Chlorophenoxy)methyl]-9-oxo-4H-pyrazolo[5,1-b]quinazoline-3-carbonitrile

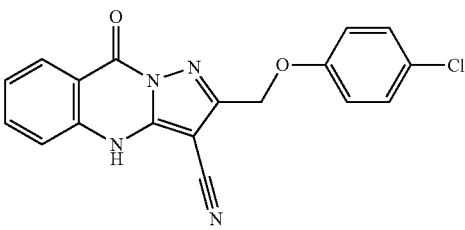 [SMILES: N#Cc1c(COc2ccc(Cl)cc2)nn2c(=O)c3ccccc3[nH]c12]

¹H NMR (500 MHz, DMSO-d₆) δ 13.37 (s, 1H), 8.19 (d, J=8.1 Hz, 1H), 7.75 (t, J=7.7 Hz, 1H), 7.53 (d, J=8.4 Hz, 1H), 7.37 (d, J=8.5 Hz, 2H), 7.29 (d, J=7.9 Hz, 1H), 7.11 (d, J=8.6 Hz, 2H), 5.28 (s, 2H). MS m/z: 351 [M+H]⁺.

Example 43. 9-Oxo-2-(3,3,3-trichloropropyl)-4,9-dihydropyrazolo[5,1-b]quinazoline-3-carboxamide

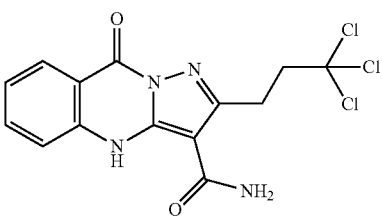 [SMILES: NC(=O)c1c(CCC(Cl)(Cl)Cl)nn2c(=O)c3ccccc3[nH]c12]

¹H NMR (500 MHz, DMSO-d₆) δ 11.78 (s, 1H), 8.21 (d, J=8.0 Hz, 1H), 7.91 (d, J=8.4 Hz, 1H), 7.81 (d, J=7.7 Hz, 1H), 7.44-7.24 (m, 3H), 3.45-3.38 (m, 2H), 3.31-3.26 (m, 2H). MS m/z: 373 [M+H]⁺.

Example 44. 9-Oxo-2-(3,3,3-trichloropropyl)-4H-pyrazolo[5,1-b]quinazoline-3-carbonitrile

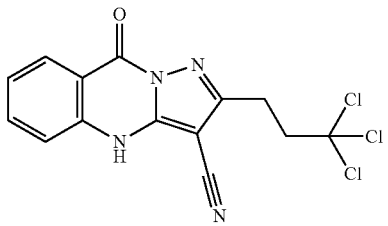 [SMILES: N#Cc1c(CCC(Cl)(Cl)Cl)nn2c(=O)c3ccccc3[nH]c12]

¹H NMR (500 MHz, DMSO-d₆) δ 13.36 (s, 1H), 8.23 (d, J=8.1 Hz, 1H), 7.86 (t, J=7.7 Hz, 1H), 7.57 (d, J=8.4 Hz, 1H), 7.41 (t, J=7.6 Hz, 1H), 3.30-3.16 (m, 4H). MS m/z: 355 [M+H]⁺.

Example 45. 2-(Cyclohexylmethyl)-9-oxo-4H-pyrazolo[5,1-b]quinazoline-3-carboxamide

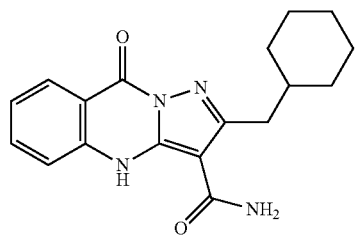 [SMILES: NC(=O)c1c(CC2CCCCC2)nn2c(=O)c3ccccc3[nH]c12]

¹H NMR (500 MHz, DMSO-d₆) δ 11.65 (s, 1H), 8.19 (d, J=8.1 Hz, 1H), 7.94 (d, J=8.4 Hz, 1H), 7.77 (t, J=7.8 Hz, 1H), 7.32 (t, J=7.6 Hz, 1H), 7.21 (s, 2H), 2.83 (d, J=7.0 Hz, 2H), 1.77 (tt, J=7.6, 3.7 Hz, 1H), 1.66 (q, J=18.2, 15.8 Hz, 5H), 1.17 (t, J=11.2 Hz, 3H), 1.00 (d, J=11.5 Hz, 2H). MS m/z: 325 [M+H]⁺.

Example 46. 2-(Cyclohexylmethyl)-9-oxo-4H-pyrazolo[5,1-b]quinazoline-3-carbonitrile

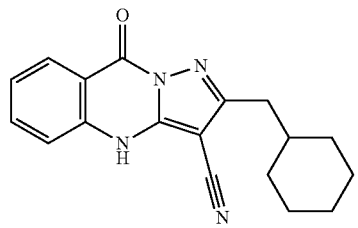 [SMILES: N#Cc1c(CC2CCCCC2)nn2c(=O)c3ccccc3[nH]c12]

¹H NMR (500 MHz, DMSO-d₆) δ 13.23 (s, 1H), 8.21 (d, J=8.1 Hz, 1H), 7.84 (t, J=7.7 Hz, 1H), 7.56 (d, J=8.4 Hz, 1H), 7.39 (t, J=7.6 Hz, 1H), 2.64 (d, J=6.9 Hz, 2H), 1.80-1.59 (m, 6H), 1.20 (h, J=11.4 Hz, 3H), 1.03 (q, J=11.3, 10.8 Hz, 2H). MS m/z: 307 [M+H]⁺.

Example 47. 2-[2-(4-Chlorophenoxy)ethyl]-9-oxo-4H-pyrazolo[5,1-b]quinazoline-3-carboxamide

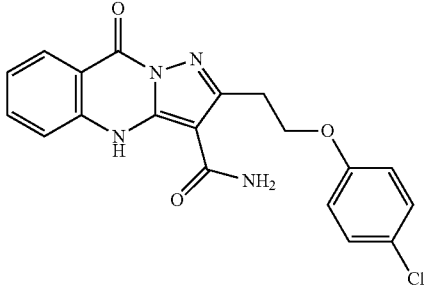 [SMILES: NC(=O)c1c(CCOc2ccc(Cl)cc2)nn2c(=O)c3ccccc3[nH]c12]

¹H NMR (500 MHz, DMSO-d₆) δ 11.73 (s, 1H), 8.20 (d, J=8.0 Hz, 1H), 7.94 (d, J=8.4 Hz, 1H), 7.79 (t, J=7.7 Hz, 1H), 7.50-7.28 (m, 5H), 6.99 (d, J=8.7 Hz, 2H), 4.39 (t, J=6.7 Hz, 2H), 3.43 (t, J=6.7 Hz, 2H). MS m/z: 383 [M+H]⁺.

Example 48. 2-[2-(4-Chlorophenoxy)ethyl]-9-oxo-4H-pyrazolo[5,1-b]quinazoline-3-carbonitrile

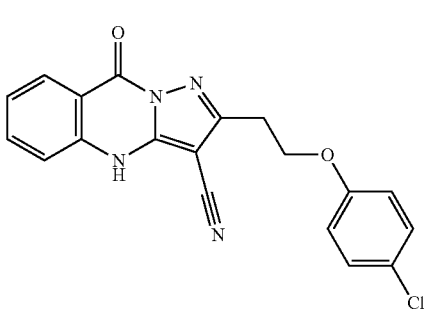 [SMILES: N#Cc1c(CCOc2ccc(Cl)cc2)nn2c(=O)c3ccccc3[nH]c12]

¹H NMR (500 MHz, DMSO-d₆) δ 13.29 (s, 1H), 8.22 (d, J=8.0 Hz, 1H), 7.85 (t, J=7.8 Hz, 1H), 7.57 (d, J=8.3 Hz, 1H), 7.40 (t, J=7.6 Hz, 1H), 7.33 (d, J=8.4 Hz, 2H), 7.00 (d, J=8.3 Hz, 2H), 4.37 (t, J=6.3 Hz, 2H), 3.24 (t, J=6.3 Hz, 2H). MS m/z: 365 [M+H]⁺.

Example 49. 8-Benzyloxy-2-(2,4-dichlorophenyl)-9-oxo-4H-pyrazolo[5,1-b]quinazoline-3-carboxamide

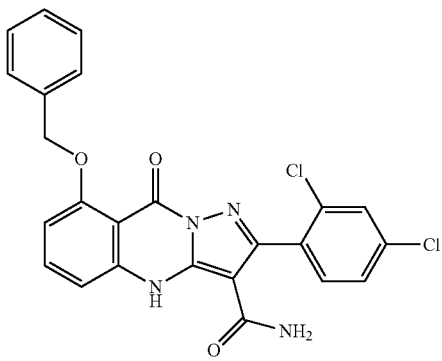 [SMILES: NC(=O)c1c(-c2ccc(Cl)cc2Cl)nn2c(=O)c3c(OCc4ccccc4)cccc3[nH]c12]

¹H NMR (500 MHz, DMSO-d6) δ 11.67 (s, 1H), 7.84 (s, 1H), 7.70 (dd, J=19.2, 7.9 Hz, 4H), 7.63 (s, 2H), 7.57 (d,

J=8.4 Hz, 1H), 7.44 (t, J=7.4 Hz, 3H), 7.35 (t, J=7.1 Hz, 1H), 6.99 (d, J=8.3 Hz, 1H), 5.35 (s, 2H). MS m/z: 479 [M+H]⁺.

Example 50. 8-Benzyloxy-2-(2,4-dichlorophenyl)-9-oxo-4H-pyrazolo[5,1-b]quinazoline-3-carbonitrile

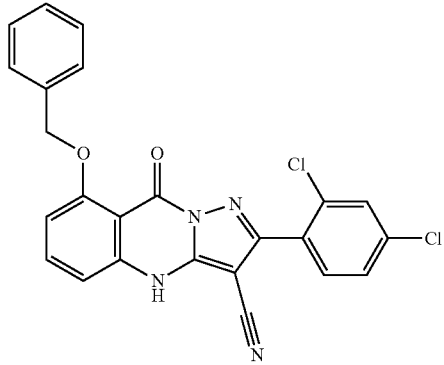 [SMILES: N#Cc1c(-c2ccc(Cl)cc2Cl)nn2c(=O)c3c(OCc4ccccc4)cccc3[nH]c12]

¹H NMR (500 MHz, DMSO-d6) δ 13.28 (s, 1H), 7.98 (s, 1H), 7.77 (t, J=8.1 Hz, 1H), 7.68 (d, J=7.3 Hz, 4H), 7.45 (t, J=7.5 Hz, 2H), 7.36 (t, J=7.3 Hz, 1H), 7.17 (d, J=8.3 Hz, 1H), 7.05 (d, J=7.9 Hz, 1H), 5.37 (s, 2H). MS m/z: 461 [M+H]⁺.

Example 51. 2-(4,4-Difluorocyclohexyl)-9-oxo-4H-pyrazolo[5,1-b]quinazoline-3-carboxamide

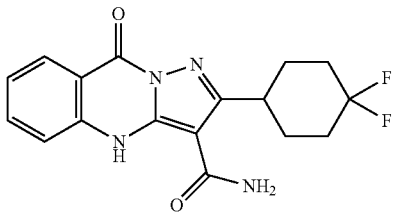 [SMILES: NC(=O)c1c(C2CCC(F)(F)CC2)nn2c(=O)c3ccccc3[nH]c12]

¹H NMR (500 MHz, DMSO-d6) δ 11.71 (s, 1H), 8.22 (d, J=8.2 Hz, 1H), 7.95 (d, J=8.5 Hz, 1H), 7.80 (t, J=7.8 Hz, 1H), 7.58-7.16 (m, 2H), 4.36 (d, J=3.8 Hz, 1H), 3.54-3.40 (m, 1H), 2.29-1.77 (m, 8H). MS m/z: 347 [M+H]⁺.

Example 52. 2-(4,4-Difluorocyclohexyl)-9-oxo-4H-pyrazolo[5,1-b]quinazoline-3-carbonitrile

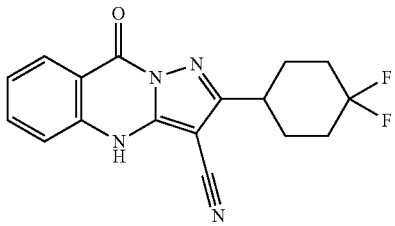 [SMILES: N#Cc1c(C2CCC(F)(F)CC2)nn2c(=O)c3ccccc3[nH]c12]

¹H NMR (500 MHz, DMSO-d6) δ 13.29 (s, 1H), 8.24 (d, J=8.1 Hz, 1H), 7.87 (t, J=7.7 Hz, 1H), 7.59 (d, J=8.3 Hz, 1H), 7.42 (t, J=7.6 Hz, 1H), 3.11 (t, J=11.6 Hz, 1H), 2.26-1.84 (m, 8H). MS m/z: 329 [M+H]⁺.

Example 53. 2-(Cyclopropylmethyl)-9-oxo-4H-pyrazolo[5,1-b]quinazoline-3-carboxamide

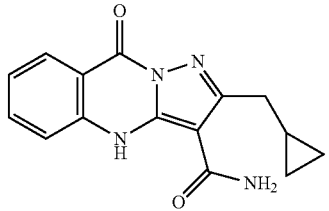 [SMILES: NC(=O)c1c(CC2CC2)nn2c(=O)c3ccccc3[nH]c12]

¹H NMR (500 MHz, DMSO-d6) δ 11.69 (s, 1H), 8.22 (d, J=8.0 Hz, 1H), 7.96 (d, J=8.4 Hz, 1H), 7.80 (t, J=7.8 Hz, 1H), 7.51-6.91 (m, 3H), 2.91 (d, J=6.8 Hz, 2H), 1.27-1.14 (m, 1H), 0.50 (d, J=7.7 Hz, 2H), 0.24 (t, J=5.0 Hz, 2H). MS m/z: 283 [M+H]⁺.

Example 54. 2-(Cyclopropylmethyl)-9-oxo-4H-pyrazolo[5,1-b]quinazoline-3-carbonitrile

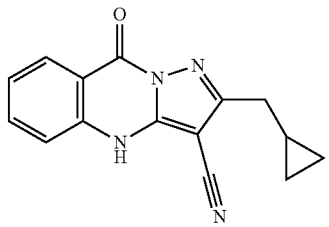 [SMILES: N#Cc1c(CC2CC2)nn2c(=O)c3ccccc3[nH]c12]

¹H NMR (500 MHz, DMSO-d6) δ 13.27 (s, 1H), 8.24 (d, J=8.0 Hz, 1H), 7.87 (t, J=7.8 Hz, 1H), 7.59 (t, J=8.3 Hz, 1H), 7.42 (t, J=7.6 Hz, 1H), 2.71 (d, J=7.0 Hz, 2H), 1.23-1.09 (m, 1H), 0.63-0.51 (m, 2H), 0.32 (t, J=5.1 Hz, 2H). MS m/z: 265 [M+H]⁺.

Example 55. 7-Benzyloxy-2-(2,4-dichlorophenyl)-9-oxo-4H-pyrazolo[5,1-b]quinazoline-3-carboxamide

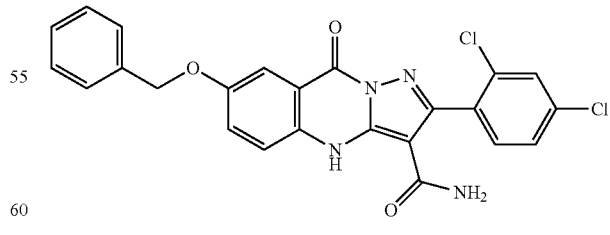

¹H NMR (500 MHz, DMSO-d6) δ 11.93 (s, 1H), 8.05 (d, J=9.1 Hz, 1H), 7.86 (s, 1H), 7.76-7.72 (m, 1H), 7.64 (s, 2H), 7.62-7.57 (m, 1H), 7.54 (d, J=7.5 Hz, 2H), 7.44 (t, J=7.4 Hz, 2H), 7.38 (t, J=7.2 Hz, 1H), 7.20 (s, 1H), 5.91 (s, 1H), 5.26 (s, 2H). MS m/z: 479 [M+H]⁺.

Example 56. 7-Benzyloxy-2-(2,4-dichlorophenyl)-9-oxo-4H-pyrazolo[5,1-b]quinazoline-3-carbonitrile

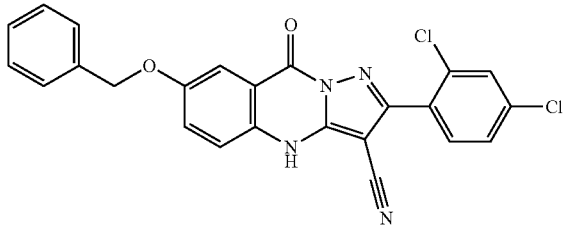 [SMILES: N#Cc1c(-c2ccc(Cl)cc2Cl)nn2c(=O)c3cc(OCc4ccccc4)ccc3[nH]c12]

$^1$H NMR (500 MHz, DMSO-d6) δ 13.47 (s, 1H), 7.94 (s, 1H), 7.76 (s, 1H), 7.69 (s, 2H), 7.62 (d, J=9.2 Hz, 2H), 7.53 (d, J=7.6 Hz, 2H), 7.45 (t, J=7.4 Hz, 2H), 7.38 (t, J=7.3 Hz, 1H), 5.28 (s, 2H). MS m/z: 461 [M+H]$^+$.

Example 57. 9-Oxo-2-(3,3,3-trifluoropropyl)-4H-pyrazolo[5,1-b]quinazoline-3-carboxamide

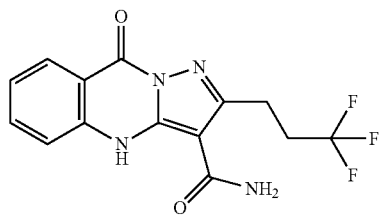 [SMILES: NC(=O)c1c(CCC(F)(F)F)nn2c(=O)c3ccccc3[nH]c12]

$^1$H NMR (500 MHz, DMSO-d6) δ 11.77 (s, 1H), 8.23 (d, J=8.0 Hz, 1H), 7.95 (d, J=8.4 Hz, 1H), 7.82 (t, J=7.7 Hz, 1H), 7.42-7.29 (m, 3H), 3.29-3.19 (m, 2H), 2.88-2.72 (m, 2H). MS m/z: 325 [M+H]$^+$.

Example 58. 9-Oxo-2-(3,3,3-trifluoropropyl)-4H-pyrazolo[5,1-b]quinazoline-3-carbonitrile

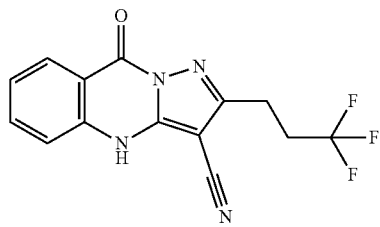 [SMILES: N#Cc1c(CCC(F)(F)F)nn2c(=O)c3ccccc3[nH]c12]

$^1$H NMR (500 MHz, DMSO-d6) δ 13.37 (s, 1H), 8.25 (d, J=8.1 Hz, 1H), 7.88 (t, J=7.7 Hz, 1H), 7.59 (d, J=8.4 Hz, 1H), 7.43 (t, J=7.6 Hz, 1H), 3.11-3.03 (m, 2H), 2.87-2.76 (m, 2H). MS m/z: 307 [M+H]$^+$.

Example 59. 9-Oxo-2-[1-(trifluoromethyl)cyclopropyl]-4H-pyrazolo[5,1-b]quinazoline-3-carbonitrile

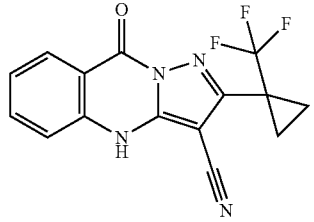 [SMILES: N#Cc1c(C2(C(F)(F)F)CC2)nn2c(=O)c3ccccc3[nH]c12]

$^1$H NMR (500 MHz, DMSO-d6) δ 13.41 (s, 1H), 8.25 (d, J=8.1 Hz, 1H), 7.88 (t, J=7.8 Hz, 1H), 7.61 (d, J=8.4 Hz, 1H), 7.43 (t, J=7.7 Hz, 1H), 1.62-1.50 (m, 2H), 1.48-1.35 (m, 2H). MS m/z: 319 [M+H]$^+$.

Example 60. 2-(3-Hydroxypropyl)-9-oxo-4H-pyrazolo[5,1-b]quinazoline-3-carboxamide

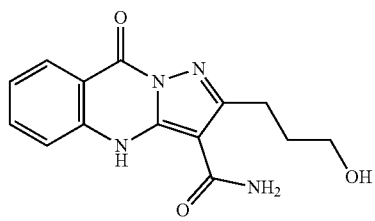 [SMILES: NC(=O)c1c(CCCO)nn2c(=O)c3ccccc3[nH]c12]

$^1$H NMR (500 MHz, DMSO-d$_6$) δ 11.67 (s, 1H), 8.20 (d, J=8.0 Hz, 1H), 7.96 (d, J=8.5 Hz, 1H), 7.78 (t, J=7.9 Hz, 1H), 7.55-7.11 (m, 3H), 4.69 (d, J=5.3 Hz, 1H), 3.49 (q, J=6.1 Hz, 2H), 2.97 (t, J=7.7 Hz, 2H), 1.87 (q, J=7.2 Hz, 2H). MS m/z: 287 [M+H]$^+$.

5. Formation of 3-Position Substituent on General Formula II Tricycle that was Formed by Method D Example 61. 2-(2,4-Dichlorophenyl)-5-oxo-4H-pyrazolo[1,5-a]quinazoline-3-carboxylic acid

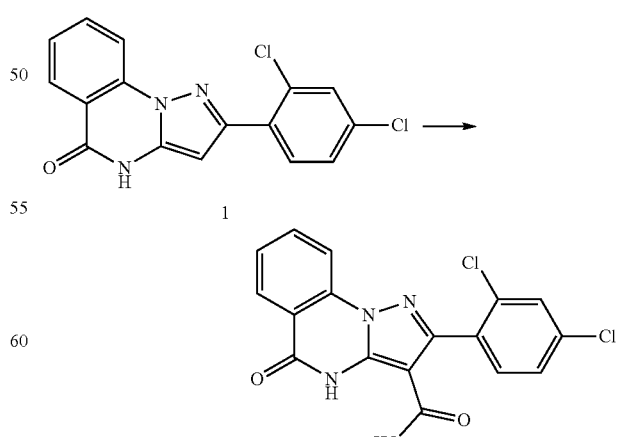

To DMF (32.8 mg, 448 mmol) was added POCl$_3$ (103.1 mg, 672 mmol) at 0° C. dropwise and the mixture was stirred at 0° C. for 15 min. To a suspension of 2-(2,4-dichlorophenyl)-4H-pyrazolo[1,5-a]quinazolin-5-one (37.0 mg, 112 mmol) in DMF (2.0 ml) was added the mixture. The mixture was stirred at 100° C. 15 h. The mixture was neutralized with sat. NaHCO$_3$(aq). and extracted with EtOAc. The combined organic layer was washed with water and brine, dried over MgSO$_4$, filtered and concentrated in vacuo. To a suspension of aldehyde in tert-butanol (2.0 mL)—water (300 uL)—THF (1.0 mL) were added sodium chlorite (20.2 mg, 223 mmol), sodium dihydrogen phosphate (29.5 mg, 246 mmol), and 2-methylbut-2-ene (11.8 mg, 168 mmol) at 0° C. The mixture was stirred at room temperature for 17 h. The mixture was concentrated. The residue was diluted with 1N NaOH aq. and washed with EtOAc. The combined aqueous layer was acidified with 1N HCl and extracted with EtOAc. The combined organic layer was dried over MgSO$_4$, filtered and concentrated in vacuo to give 2-(2,4-dichlorophenyl)-5-oxo-4H-pyrazolo[1,5-a]quinazoline-3-carboxylic acid (26.3 mg, 63% (in 2 steps)). 1H NMR (500 MHz, DMSO-d$_6$) δ 11.99 (s, 1H), 11.06 (s, 1H), 8.25 (d, J=9.2 Hz, 1H), 8.14 (d, J=8.2 Hz, 1H), 7.97 (t, J=8.4 Hz, 1H), 7.79 (s, 1H), 7.63 (t, J=7.6 Hz, 1H), 7.56 (d, J=1.7 Hz, 2H). MS m/z: 372 [M+H]$^+$.

Example 62. 2-(2,4-Dichlorophenyl)-5-oxo-4H-pyrazolo[1,5-a]quinazoline-3-carboxamide

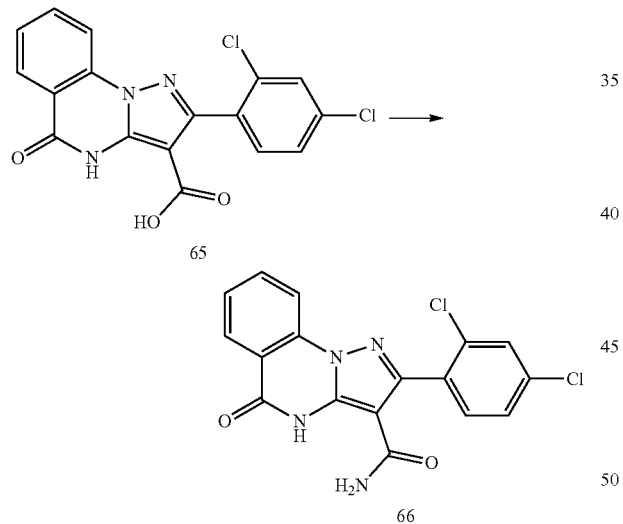

To a solution of 2-(2,4-dichlorophenyl)-5-oxo-4H-pyrazolo[1,5-a]quinazoline-3-carboxylic acid (25.0 mg, 66.8 mmol) in DMA (2.0 mL) were added ammonium chloride (33.0 mg, 668 mmol) and HATU (38.1 mg, 100 mmol), DIPEA (36.8 mg, 285 mmol) at room temperature. The mixture was stirred at room temperature over the weekend. The mixture was diluted with sat. NaHCO$_3$ (aq). The mixture was extracted with CH$_2$Cl$_2$. The combined organic layer was washed with water and brine, dried over MgSO$_4$, filtered and concentrated in vacuo. The residue was washed with hexane to give 2-(2,4-dichlorophenyl)-5-oxo-4H-pyrazolo[1,5-a]quinazoline-3-carboxamide (10.0 mg, 26.8 mmol, 40% yield) as colorless amorphous solid. 1H NMR (500 MHz, DMSO-d$_6$) δ 8.22 (d, J=7.5 Hz, 2H), 8.12 (d, J=8.2 Hz, 1H), 7.94 (t, J=8.0 Hz, 1H), 7.79 (s, 1H), 7.59 (d, J=8.1 Hz, 3H), 6.98 (d, J=7.2 Hz, 2H). MS m/z: 373 [M+H]$^+$.

Example 63 (alternate synthesis of Example 2). 2-(2,4-Dichlorophenyl)-5-oxo-4H-pyrazolo[1,5-a]quinazoline-3-carbonitrile

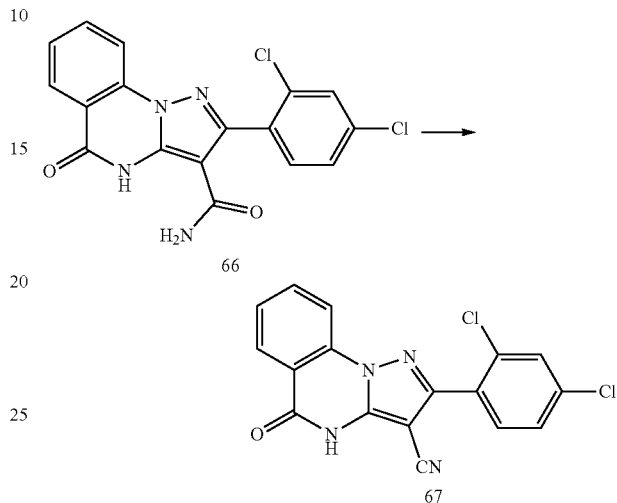

To a solution of 2-(2,4-dichlorophenyl)-5-oxo-4H-pyrazolo[1,5-a]quinazoline-3-carboxamide (7.8 mg, 21 mmol) in DMF (1.0 mL) was added SOCl$_2$ (10.0 mg, 83.6 mmol) at 0° C. The mixture was stirred at 0° C. for 30 min. The mixture was diluted with sat. NaHCO$_3$(aq). and water. The precipitate was collected by filtration and washed with hexane to give 2-(2,4-dichlorophenyl)-5-oxo-4H-pyrazolo[1,5-a]quinazoline-3-carbonitrile (3.2 mg, 9.0 mmol, 43% yield) as colorless amorphous solid. 1H NMR (500 MHz, DMSO-d$_6$) δ 13.48 (s, 1H), 8.20 (d, J=7.8 Hz, 1H), 8.10 (d, J=8.0 Hz, 1H), 7.90 (d, J=2.0 Hz, 2H), 7.73-7.63 (m, 2H), 7.58 (t, J=7.1 Hz, 1H). MS m/z: 353 [M+H]$^+$.

The following are more examples synthesized via method B.

Example 64. 2-[1-(4-Chlorophenyl)cyclopropyl]-7-methoxy-5-oxo-4H-pyrazolo[1,5-a]quinazoline-3-carbonitrile

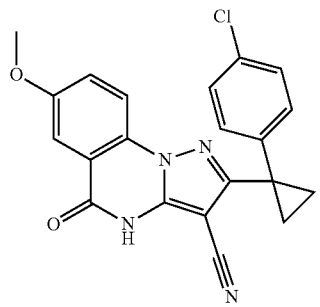 [SMILES: COc1ccc2c(c1)c(=O)[nH]c1c(C#N)c(C3(c4ccc(Cl)cc4)CC3)nn12]

$^1$H NMR (500 MHz, DMSO-d$_6$) δ 13.24 (s, 1H), 8.03 (d, J=9.0 Hz, 1H), 7.61-7.48 (m, 2H), 7.39-7.23 (m, 4H), 3.89 (s, 3H), 1.52 (q, J=4.5 Hz, 2H), 1.39 (q, J=4.5 Hz, 2H). MS m/z: 391 [M+H]$^+$.

Example 65. 2-(2,4-Dichlorophenyl)-7-methoxy-5-oxo-4H-pyrazolo[1,5-a]quinazoline-3-carbonitrile

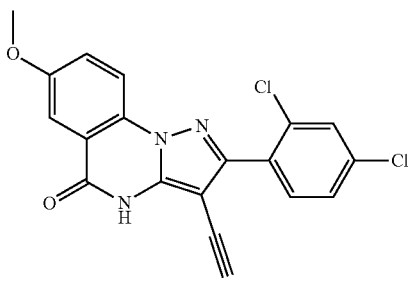 [SMILES: C#Cc1c(-c2ccc(Cl)cc2Cl)nn2c1[nH]c(=O)c1cc(OC)ccc12]

$^1$H NMR (500 MHz, DMSO-d$_6$) δ 13.48 (s, 1H), 8.08 (d, J=9.0 Hz, 1H), 7.90 (d, J=1.9 Hz, 1H), 7.68-7.60 (m, 3H), 7.56 (dd, J=9.0, 2.9 Hz, 1H), 3.91 (s, 3H). MS m/z: 385 [M+H]$^+$.

Example 66. 2-[1-(4-Chlorophenyl)cyclopropyl]-5-oxo-4H-pyrazolo[1,5-a]quinazoline-3,7-dicarbonitrile

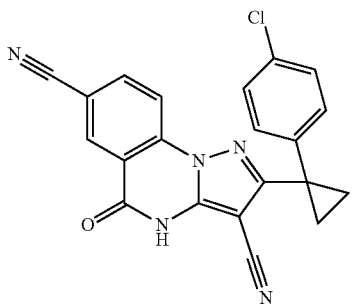 [SMILES: N#Cc1ccc2c(c1)c(=O)[nH]c1c(C#N)c(C3(c4ccc(Cl)cc4)CC3)nn12]

$^1$H NMR (500 MHz, DMSO-d$_6$) δ 8.33 (d, J=1.9 Hz, 1H), 8.05-7.94 (m, 2H), 7.37-7.32 (m, 2H), 7.31-7.26 (m, 2H), 1.55-1.45 (m, 2H), 1.34-1.28 (m, 2H). MS m/z: 384 [M+H]$^+$.

The following examples show the formation of 3-alkoxycarbonyl compounds of the general formula II via method D.

Example 67. Methyl 2-(2,4-dichlorophenyl)-9-oxo-4H-pyrazolo[5,1-b]quinazoline-3-carboxylate

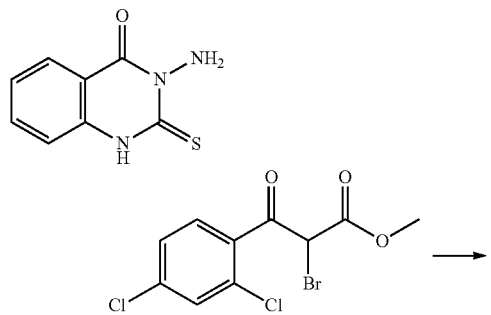

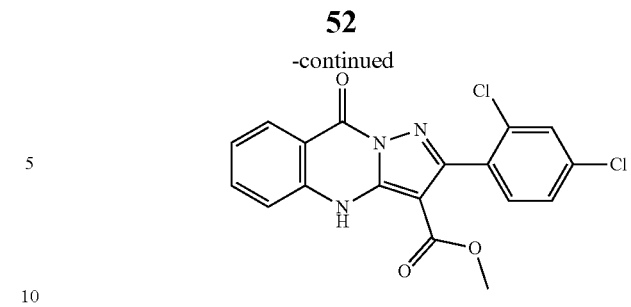

The mixture of 3-amino-2-thioxo-1H-quinazolin-4-one (20.0 mg, 104 μmol) and methyl 2-bromo-3-(2,4-dichlorophenyl)-3-oxo-propanoate (43.5 mg, 134 μmol) in MeOH (4.0 mL) was irradiated by microwave at 120° C. for 2 h. The mixture was concentrated. The insoluble material was removed by filtration and washed with THF. The residue was purified by column chromatography (Silica gel, 0%-30% hexane in EtOAc) and washed with hexane and IPE to give methyl 2-(2,4-dichlorophenyl)-9-oxo-4H-pyrazolo[5,1-b]quinazoline-3-carboxylate (3.2 mg, 8.2 μmol, 8% yield) as colorless solid. $^1$H NMR (500 MHz, DMSO-d6) δ 11.94 (s, 1H), 8.28 (d, J=7.2 Hz, 1H), 8.02 (s, 1H), 7.88 (s, 1H), 7.80 (s, 1H), 7.65-7.51 (m, 2H), 7.43 (s, 1H), 3.72 (s, 3H). MS m/z: 388 [M−H]$^+$.

Example 68. Isopropyl 2-(2,4-dichlorophenyl)-9-oxo-4H-pyrazolo[5,1-b]quinazoline-3-carboxylate

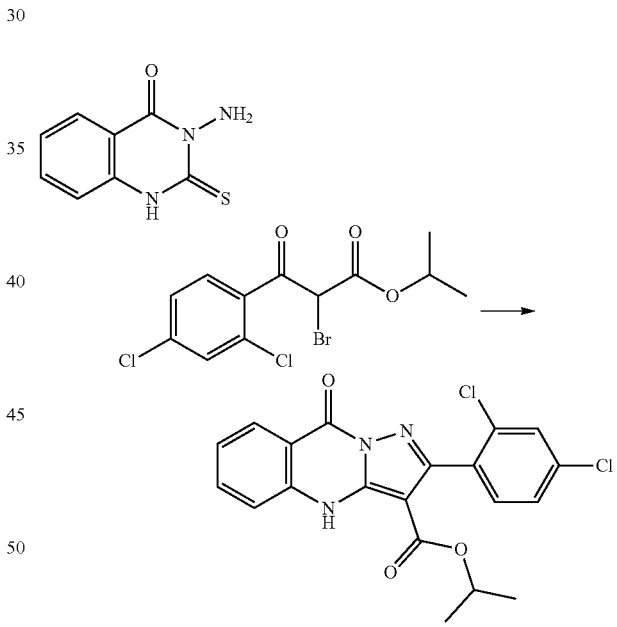

The mixture of 3-amino-2-thioxo-1H-quinazolin-4-one (43.0 mg, 223 μmol) and 2-bromo-3-(2,4-dichlorophenyl)-N,N-dimethyl-3-oxo-propanamide (90.5 mg, 267 μmol) in IPA (5.0 mL) was stirred at 95° C. for 15 h. The reaction mixture was cooled to room temperature. The mixture was concentrated. To the residue was added EtOAc. The solid residue was filtered and washed with IPA. The solid was purified by column chromatography (Silica gel, 0%-30% hexane in EtOAc). The solid was washed with hexane to give isopropyl 2-(2,4-dichlorophenyl)-9-oxo-4H-pyrazolo[5,1-b]quinazoline-3-carboxylate (5.4 mg, 13 μmol, 6% yield) as colorless solid. $^1$H NMR (500 MHz, DMSO-d6) δ 12.15 (s, 1H), 8.28 (dd, J=8.1, 1.3 Hz, 1H), 8.06 (d, J=8.4

Hz, 1H), 7.88 (t, J=7.7 Hz, 1H), 7.82 (d, J=2.0 Hz, 1H), 7.60 (dd, J=8.2, 2.0 Hz, 1H), 7.54 (d, J=8.2 Hz, 1H), 7.44 (t, J=7.5 Hz, 1H), 4.97 (hept, J=6.2 Hz, 1H), 1.04 (d, J=6.2 Hz, 6H). MS m/z: 418 [M+H]⁺.

6. Formation of General Formula II Tricycle—Method E

Some compounds of general formula II are synthesized by employing the reaction between 2-aminobenzohydrazides and β-keto esters:

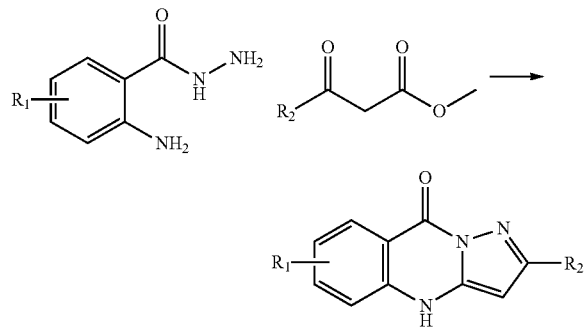

Example 69. 6-Chloro-2-(2,4-dichlorophenyl)-4H-pyrazolo[5,1-b]quinazolin-9-one

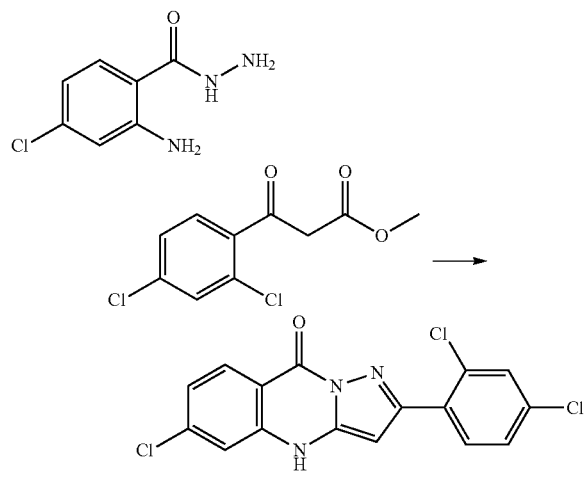

To a solution of 2-amino-4-chloro-benzohydrazide (50.0 mg, 269 μmol) in MeOH (3.0 mL) were added methyl 3-(2,4-dichlorophenyl)-3-oxo-propanoate (66.6 mg, 269 mol) and 4-methylbenzenesulfonic acid hydrate (51.2 mg, 269 μmol) at room temperature. The mixture was stirred at room temperature for 2 h. The mixture was stirred at 70° C. for 2 d. The precipitate was collected by filtration and washed with MeOH to give 6-chloro-2-(2,4-dichlorophenyl)-4H-pyrazolo[5,1-b]quinazolin-9-one (25.0 mg, 68.6 μmol, 25% yield) as colorless solid. ¹H NMR (500 MHz, DMSO-d6) δ 12.54 (s, 1H), 8.24 (d, J=8.6 Hz, 1H), 7.96 (d, J=8.4 Hz, 1H), 7.82 (s, 1H), 7.61 (dd, J=8.4, 1.6 Hz, 1H), 7.47 (s, 1H), 7.33 (d, J=8.6 Hz, 1H), 6.60 (s, 1H). MS m/z: 364 [M−H]⁺.

Other examples shown below were synthesized using method E:

Example 70. 2-(2,4-Dichlorophenyl)-4H-pyrazolo[5,1-b]quinazolin-9-one

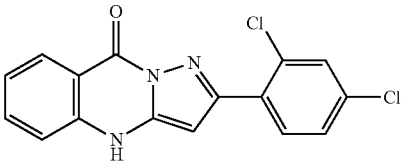 [SMILES: O=c1c2ccccc2[nH]c2cc(-c3ccc(Cl)cc3Cl)nn12]

¹H NMR (500 MHz, DMSO-d6) δ 12.44 (s, 1H), 8.25 (d, J=8.1 Hz, 1H), 7.98 (d, J=8.4 Hz, 1H), 7.86-7.78 (m, 2H), 7.61 (d, J=8.4 Hz, 1H), 7.46 (d, J=8.4 Hz, 1H), 7.32 (t, J=7.6 Hz, 1H), 6.57 (s, 1H). MS m/z: 330 [M−H]⁺.

Example 71. 2-[4-(Trifluoromethyl)phenyl]-4H-pyrazolo[5,1-b]quinazolin-9-one

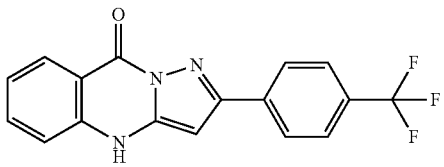 [SMILES: O=c1c2ccccc2[nH]c2cc(-c3ccc(C(F)(F)F)cc3)nn12]

¹H NMR (500 MHz, DMSO-d6) δ 12.48 (s, 1H), 8.30 (d, J=7.9 Hz, 2H), 8.25 (d, J=8.1 Hz, 1H), 7.89 (d, J=7.9 Hz, 2H), 7.81 (t, J=7.7 Hz, 1H), 7.47 (d, J=8.4 Hz, 1H), 7.32 (t, J=7.5 Hz, 1H), 6.73 (s, 1H). MS m/z: 330 [M+H]⁺.

The following examples show derivatization at the 3-position of example 70.

Example 72. 2-(2,4-Dichlorophenyl)-3-[(dimethylamino)methyl]-4H-pyrazolo[5,1-b]quinazolin-9-one

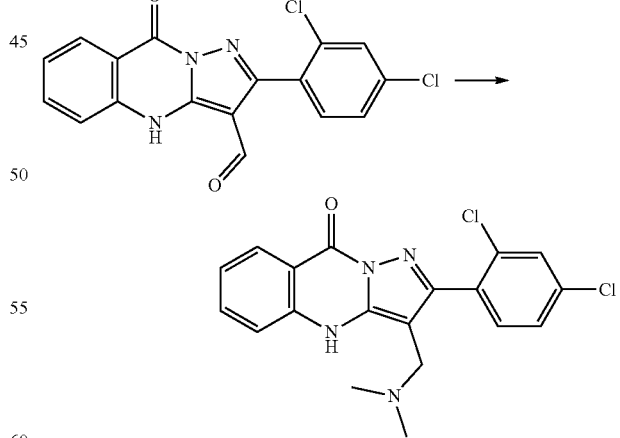

To a suspension of 2-(2,4-dichlorophenyl)-9-oxo-4H-pyrazolo[5,1-b]quinazoline-3-carbaldehyde (35.3 mg, 98.5 μmol, obtained via formulation of example 74) in DMA (2.0 mL) were added dimethylamine in THF (2.0 M, 246 mL) and acetic acid (210 mg, 3.49 mmol) at room temperature. After 30 min, sodium triacetoxyboranuide (41.8 mg, 197 mmol) was added to the mixture at room temperature, and it was stirred at room temperature for 21 h. Dimethylamine in THF (2.0 M, 246 mL), acetic acid (209.80 mg, 3.49 mmol) and sodium triacetoxyboranuide (41.8 mg, 197 mmol) were added to the mixture, and it was stirred at room temperature for 3 d. The reaction mixture was neutralized with sat. NaHCO$_3$aq. and extracted with EtOAc. The organic layer was separated, washed with water and brine, dried over MgSO$_4$, filtered and concentrated in vacuo. The residue was purified by column chromatography (NH-Silica gel, 0%-25% EtOAc in MeOH) and washed with EtOAc/hexane to give 2-(2,4-dichlorophenyl)-3-[(dimethylamino)methyl]-4H-pyrazolo[5,1-b]quinazolin-9-one (23.0 mg, 59.4 μmol, 60% yield) as pale yellow solid. $^1$H NMR (500 MHz, DMSO-d6) δ 8.24 (d, J=8.1 Hz, 1H), 7.85-7.77 (m, 2H), 7.65 (d, J=8.4 Hz, 1H), 7.61 (q, J=8.3 Hz, 2H), 7.31 (t, J=7.5 Hz, 1H), 3.43 (s, 2H), 2.07 (s, 6H), 1H was hidden. MS m/z: 385 [M−H]$^−$.

Example 73. 2-(2,4-Dichlorophenyl)-3-iodo-4H-pyrazolo[5,1-b]quinazolin-9-one

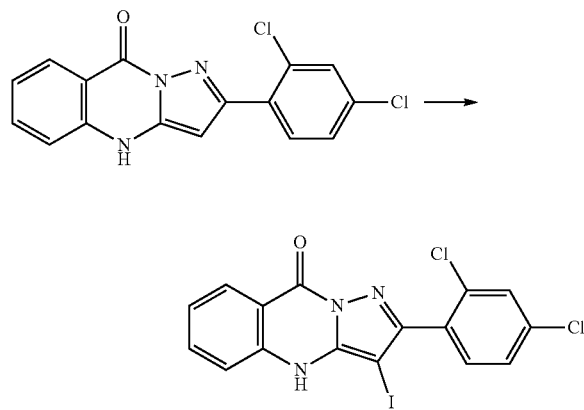

To a suspension of 2-(2,4-dichlorophenyl)-4H-pyrazolo[5,1-b]quinazolin-9-one (52.3 mg, 158 μmol) in DMF (2.0 mL) was added NIS (39.2 mg, 174 μmol) at 0° C. The mixture was stirred at room temperature for 2 h and was quenched with sat. NaHCO$_3$aq. and water. The precipitate was collected by filtration to give 2-(2,4-dichlorophenyl)-3-iodo-4H-pyrazolo[5,1-b]quinazolin-9-one (71.7 mg, 157 μmol, 99% yield) as pale yellow solid. $^1$H NMR (500 MHz, DMSO-d6) δ 12.17 (s, 1H), 8.24 (d, J=8.1 Hz, 1H), 7.87 (s, 1H), 7.83 (t, J=7.3 Hz, 1H), 7.73 (d, J=8.2 Hz, 1H), 7.62 (d, J=8.2 Hz, 1H), 7.54 (d, J=8.2 Hz, 1H), 7.35 (t, J=7.0 Hz, 1H). MS m/z: 456 [M+1]$^+$.

The conversion of chemical potential energy into mechanical force by AAA+ ATPases is integral to a myriad of cellular processes, as discussed above in the Background section. Investigations into the dynamic functions of this protein superfamily would benefit from small-molecule modulators, yet inhibitors of these complex, oligomeric mechanoenzymes have remained elusive. This patent application describes pyrazoloquinazolinones that are selective inhibitors of dyneins 1 and 2. The experiments described herein demonstrate the ability of pyrazoloquinazolinone derivatives to selectively block dynein-dependent microtubule gliding in vitro. In addition to their utility in vivo as anti-tumor agents, the compounds are therefore useful reagents in vitro for studying cellular processes that employ this minus-end-directed microtubule motor.

Assays

Compounds were tested employing a microtubule gliding assay, a standard biochemical assay for motor proteins. The first set of studies focused on human cytoplasmic dynein 2, the isoform involved in ciliary transport and Hedgehog signaling, as its inhibition in this assay has not been previously demonstrated. We purified an N-terminally GFP-tagged motor-domain construct of dynein 2 using an insect cell expression system [Schmidt et al., Nature. 2015; 518 (7539):435-8]. The GFP tag in this construct allowed immobilization on passivated glass coverslips used in microtubule gliding assays. GFP-dynein 2, in the presence of ATP (1 mM), moved microtubules with a velocity of 128±14 nm/s. The mean velocity of dynein 2-driven microtubule gliding in the presence of control solvent (2% DMSO) and test compounds at 20 pM were compared. All motility assays were run at 1 mM MgATP, 0.05 mg/mL casein, and 2% DMSO. Representative examples of compounds of the invention provided the results shown as "Gliding velocity in nm/s" in Table 1. For some compounds, dose-dependent analyses were performed, and the results are shown as "IC$_{50}$ in μM" in Table 1.

TABLE 1

| Example # | Structure | Gliding velocity nm/s | IC$_{50}$ μM |
|---|---|---|---|
| control | solvent | 126 ± 17 | |
| 1 | 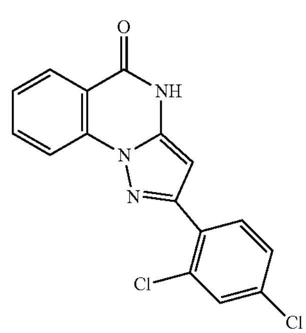 [SMILES: O=c1[nH]c2cc(-c3ccc(Cl)cc3Cl)nn2c2ccccc12] | 83 ± 10 | |

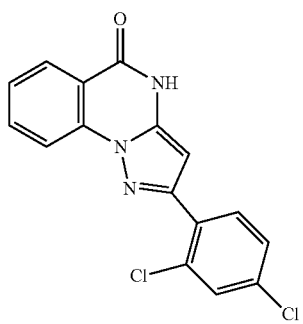

TABLE 1-continued

| Example # | Structure | Gliding velocity nm/s | IC$_{50}$ μM |
|---|---|---|---|
| 2 | 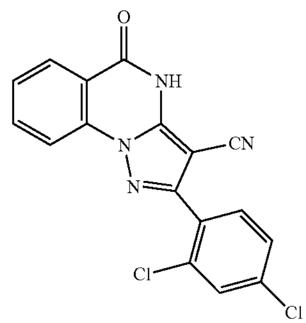 [SMILES: N#Cc1c(-c2ccc(Cl)cc2Cl)nn2c1[nH]c(=O)c1ccccc12] | 83 ± 10 | |
| 3 | 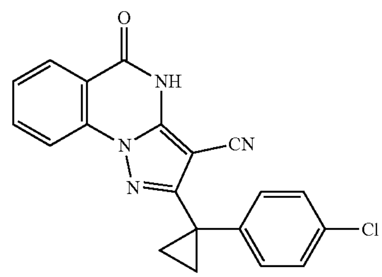 [SMILES: N#Cc1c(C2(c3ccc(Cl)cc3)CC2)nn2c1[nH]c(=O)c1ccccc12] | 58 ± 14 | |
| 4 | 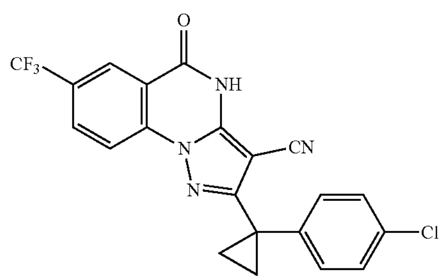 [SMILES: N#Cc1c(C2(c3ccc(Cl)cc3)CC2)nn2c1[nH]c(=O)c1cc(C(F)(F)F)ccc12] | 6 ± 2 | 3.3 ± 0.2 |
| 5 | 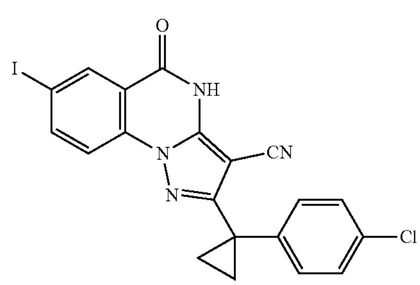 [SMILES: N#Cc1c(C2(c3ccc(Cl)cc3)CC2)nn2c1[nH]c(=O)c1cc(I)ccc12] | 6 ± 2 | 2.6 ± 1.3 |
| 12 | 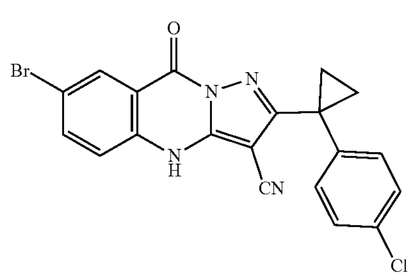 [SMILES: N#Cc1c(C2(c3ccc(Cl)cc3)CC2)nn2c(=O)c3cc(Br)ccc3[nH]c12] | | 0.29 |

TABLE 1-continued

| Example # | Structure | Gliding velocity nm/s | IC$_{50}$ μM |
|---|---|---|---|
| 27 | 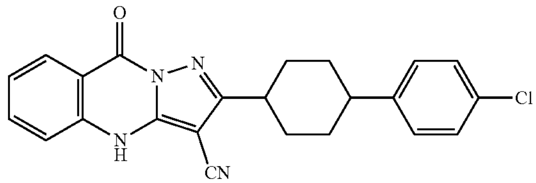 [SMILES: N#Cc1c(C2CCC(c3ccc(Cl)cc3)CC2)nn2c(=O)c3ccccc3[nH]c12] | | 0.62 |
| 31 | 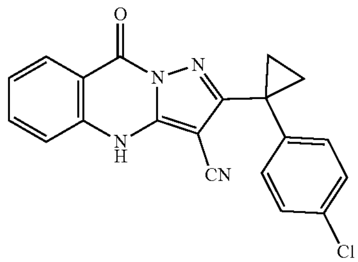 [SMILES: N#Cc1c(C2(c3ccc(Cl)cc3)CC2)nn2c(=O)c3ccccc3[nH]c12] | | 0.71 |
| 29 | 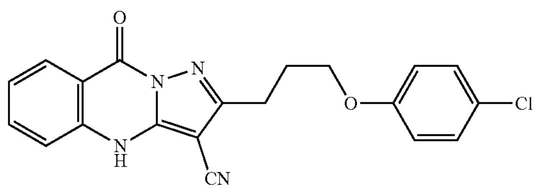 [SMILES: N#Cc1c(CCCOc2ccc(Cl)cc2)nn2c(=O)c3ccccc3[nH]c12] | | 0.73 |

To examine the inhibition of dynein 2 in cell-based assays, an established luciferase reporter-based cellular assay of Hedgehog pathway activity was employed [Taipale et al., *Nature.* 2000; 406(6799): 1005-9]. Signaling in this pathway depends on the function of dynein 2. In this setting, expression of luciferase driven by Hedgehog pathway activity was inhibited by compound 5 with an IC$_{50}$ value of 0.9±0.5 μM. Compound 2, which lacks the cyclopropyl moiety, inhibited Hedgehog pathway activity with IC$_{50}$ of 5.2±5 μM. The potencies of these compounds in this cell-based assay match the rank-order of dynein 2 inhibition in vitro. In these assays, Hedgehog pathway activity was stimulated using the Synthetic Agonist of Smoothened (SAG). This compound competes with many Hedgehog pathway inhibitors for binding to Smoothened, a key node in the signaling pathway. As these compounds inhibit Hedgehog signaling at high SAG concentrations (500 nM), the data suggest that that they act downstream of Smoothened, consistent with inhibition of dynein 2.

Based on the structure-activity data, one might predict that compound 5 could also inhibit cytoplasmic dynein 1. To examine the inhibition of dynein 1 by compound 5 in vitro we generated recombinant human protein. We expressed and purified a GFP-tagged human dynein 1 (AA 1320-'16'16) construct similar to the one we used for GFP dynein 2. This protein migrated with a peak volume of 12.6 mL in size exclusion chromatography and SDS-PAGE analysis showed >90% purity. GFP-dynein 1 moves microtubules at 510±60 nm/s, a velocity expected based on studies of other mammalian dynein 1 homologs (n=7). Time-lapse montages showed that compound 5 slowed dynein-dependent microtubule gliding. Dose-dependent analysis indicated that compound 5 blocked GFP-dynein 1-driven motility with an IC$_{50}$ of 2.3±1.41/M. The potency of compound 5 was sensitive to the protein (e.g. blocking agent, serum) concentration in solution, likely due to the hydrophobicity of these compounds (calculated logarithm of octanol:water partition coefficient [C log P] of compound 5=4.8). Inhibition of dynein 1-dependent microtubule gliding by compound 5 was reversed following washout, as is also the case for dynein 2-dependent motility, suggesting that compounds of the invention can be used as chemical probes to inhibit or activate (via washout) dynein function.

To test whether dynein 1 is inhibited by compound 5 in a cellular context, we monitored the trafficking of lysosomes, a process that depends on cytoplasmic dynein 1. In neurites of CAD cells, a neuron-like catecholaminergic murine cell line, lysosomes move directionally. These dynamics can be observed by imaging live cells treated with an acid-sensitive dye (LysoTracker). Overlays of successive images from a time-lapse series, color-coded for displacement, reveal organelle motion. Lysosomes moved with tracks averaging 32±11 pm in length in control cells. Compound 5 (5 pM) shortened the average track length to 6.7±2.7 pm without particle translocation. A lower dose of compound 5 (3.5 pM) reduced the average track length to 15.7±4.7 pm. These dose-dependent changes in lysosome dynamics are consistent with inhibition of dynein 1 by compound 5 in living cells.

Of the six AAA sites in dynein, only mutations at AAA1 and AAA3 substantially inhibit motility. Given that compounds of the invention inhibit dynein ATPase activity, it is likely that these compounds inhibit at least one of these two sites. ATPase activity at AAA1 is linked to individual steps of the motor, while the AAA3 site plays a regulatory role. Two lines of evidence indicate that compounds of the invention target the AAA1 site specifically. First, compound 5 inhibits the activity of a dynein 1 construct with a mutation in the AAA3 domain (Walker A residue). In this construct, the ATPase activity is expected to be mainly due to the AAA1 site. Second, the potency of inhibition of the AAA3 mutant is similar to that of the microtubule-stimulated ATPase rate. Sequence comparisons indicate that the AAA1 sites in dynein 1 and 2 are highly conserved, while the other AAA sites are less conserved. In fact, the residues within 4 Å of the bound nucleotide in AAA1 are identical between dynein 1 and 2. This sequence similarity and the observation that compound 5 inhibits dynein 1 and 2 with comparable potency are consistent with a model in which this compound selectively inhibits hydrolysis of dynein's AAA1 site.

Microtubule surface gliding assay. Cytoplasmic dynein was purified from bovine brains as described by Bingham et al. [Methods Enzymol. 298, 171 (1998)]. K560, a 560-amino acid N-terminal fragment of human conventional kinesin (kinesin-1) with a C-terminal His-tag, was expressed in bacteria and purifed as described by Woehlke et al., [Cell 90, 207 (1997)]. Motility assays were performed on a Zeiss Axiovert 200M wide-field microscope equipped with a Zeiss 100×/1.45 NA α-Plan-Fluar objective. Data were captured with an EM-CCD camera (iXon DU-897, Andor Technology) with a 0.3-second exposure time and frame rate of 0.5 second$^{-1}$. Microtubule gliding assays were performed as described by Kapoor and Mitchison [Proc. Natl. Acad. Sci. U.S.A 96, 9106 (1999)] with some modifications. An approximately 6-μL flow chamber was filled with motor protein (100 μg/mL dynein or 50 μg/mL K560) in motor dilution buffer (80 mM Pipes, 1 mM EGTA, 2 mM MgCl$_2$, 2 mM DTT, 50 μM ATP, pH 6.8 with KOH). After a 2-minute incubation, excess protein was washed out with 20 μL of PEM80 buffer (80 mM Pipes, 1 mM EGTA, 2 mM MgCl$_2$, pH 6.8 with KOH) and the surface was blocked against non-specific microtubule binding by filling the chamber with blocking protein (0.5 mg/mL α-casein for dynein experiments and 1 mg/mL BSA for K560 experiments) in motor dilution buffer. After 2 minutes the chamber was perfused with 18 μL of reaction mix (PEM80, 40 mM KC 1, blocking protein [1 mg/mL α-casein for dynein experiments; 1 mg/mL BSA for K560 experiments], 2 mM MgATP, 20 μM taxol, 0.1 μM rhodamine-labeled microtubules, oxygen depletion system [4 mM DTT, 2 mM glucose, 40 μg/mL glucose oxidase, 35 μg/mL catalase], 2.5% DMSO, and test compounds as appropriate). The flow chamber was then sealed with valap. After allowing the microtubules to bind to the surface for 5 minutes, the gliding microtubules were visualized by time-lapse fluorescence microscopy. Velocities were measured by kymography using Metamorph software (Molecular Devices), and the velocity for each microtubule was determined from the total distance during the time observed.

For washout experiments, the chamber was left unsealed after the initial reaction mix containing inhibitor was added. Microtubules were allowed to bind to the surface for 5 minutes, and then a time-lapse movie was acquired. The inhibitor was then washed out of the chamber by flowing in 20 μL of fresh reaction mix (PEM80, 40 mM KCl, 1 mg/mL α-casein, 2 mM MgATP, 20 μM taxol, oxygen depletion system, and 2.5% DMSO) without additional microtubules or inhibitor. The chamber was sealed, and additional time-lapse movies were acquired.

SHH-Light Assay (Steinman et al. eLife 2017; 6:e25174.)

NIH-3T3 cells stably expressing a luciferase reporter downstream of a Gli binding site (Shh-Light2 cells, RRID: CVCL_2721) were maintained in DMEM with 10% bovine calf serum (BCS). Cells were seeded at a density of 30,000 cells/well in 96-well tissue culture-treated plates (Corning, cat #353072) in 100 μL in DMEM+10% BCS, and incubated for 48 hr (Taipale et al., 2000). Wells were washed briefly with PBS. Next 100 L of low serum media (DMEM+0.5% BCS) containing smoothened agonist (SAG, 500 nM), and either solvent control (0.2% DMSO) or test compound (serial three-fold dilutions of each inhibitor starting from 20 μM) were added to the wells. After 28-32 hr of inhibitor treatment, cells were washed with 50 μL PBS and lysed for >30 min in 30 μL Passive Lysis Buffer (Promega Dual Luciferase kit, cat E1910). 5 uL of each lysate was transferred to white, solid-bottom 96-well plates (Greiner, cat #655075), followed by rapid addition (within 30 s) of 30 μL of Luciferase Assay Reagent using a multichannel pipette. Luminescence for each condition was read using a Synergy Neo plate reader (5 s integration time per well). Cell line identity was confirmed by measurement of the degree of response to Hedgehog pathway stimulation by the synthetic agonist SAG and using previously published values from our groups and others as references (Firestone et al., 2012; Hyman et al., 2009). See Table 2 for activities.

TABLE 2

| Structure | Example # | Shh-light IC50, μM | SHH-light % residual @ 2 μM | SHH-light % residual @ 20 μM |
|---|---|---|---|---|
| 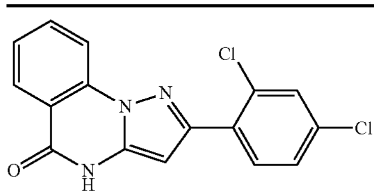 | 1 |  |  |  |
| 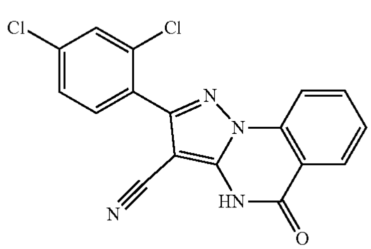 [SMILES: N#Cc1c(-c2ccc(Cl)cc2Cl)nn2c1[nH]c(=O)c1ccccc12] | 2 |  |  | 19.1 |

TABLE 2-continued

| Structure | Example # | Shh-light IC50, μM | SHH-light % residual @ 2 μM | SHH-light % residual @ 20 μM |
|---|---|---|---|---|
| 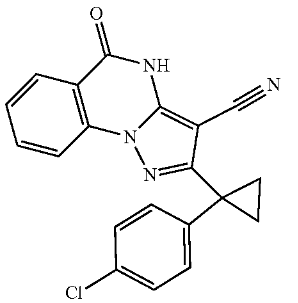 [SMILES: N#Cc1c(C2(c3ccc(Cl)cc3)CC2)nn2c1[nH]c(=O)c1ccccc12] | 3 | | | |
| 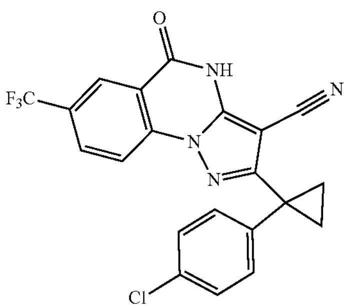 [SMILES: N#Cc1c(C2(c3ccc(Cl)cc3)CC2)nn2c1[nH]c(=O)c1cc(C(F)(F)F)ccc12] | 4 | 41.8 | −4.4 | |
| 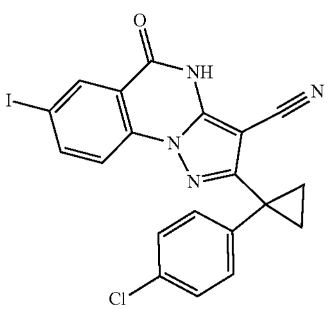 [SMILES: N#Cc1c(C2(c3ccc(Cl)cc3)CC2)nn2c1[nH]c(=O)c1cc(I)ccc12] | 5 | 1.45 | 24.8 | −5.2 |
| 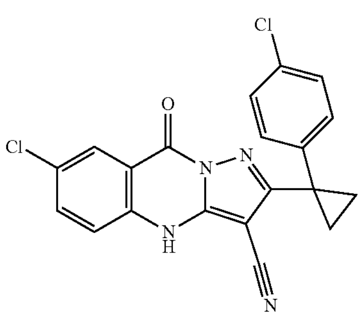 [SMILES: N#Cc1c(C2(c3ccc(Cl)cc3)CC2)nn2c(=O)c3cc(Cl)ccc3[nH]c12] | 18 | 0.76 | −0.5 | 2.8 |
| 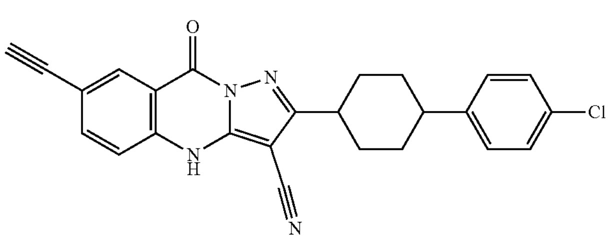 [SMILES: C#Cc1ccc2[nH]c3c(C#N)c(C4CCC(c5ccc(Cl)cc5)CC4)nn3c(=O)c2c1] | 6 | | | |

TABLE 2-continued

| Structure | Example # | Shh-light IC50, μM | SHH-light % residual @ 2 μM | SHH-light % residual @ 20 μM |
|---|---|---|---|---|
| 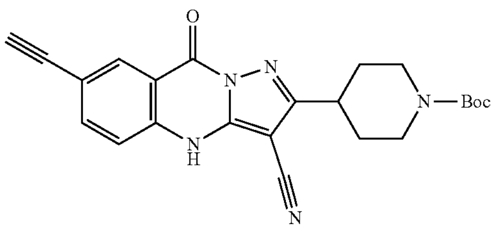 [SMILES: C#Cc1ccc2[nH]c3c(C#N)c(C4CCN(C(=O)OC(C)(C)C)CC4)nn3c(=O)c2c1] | 7 | | | |
| 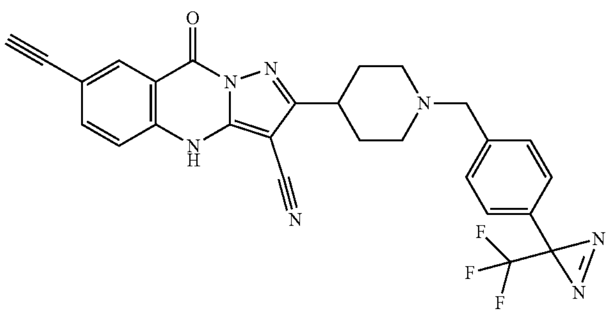 [SMILES: C#Cc1ccc2[nH]c3c(C#N)c(C4CCN(Cc5ccc(C6(C(F)(F)F)N=N6)cc5)CC4)nn3c(=O)c2c1] | 8 | | | |
| 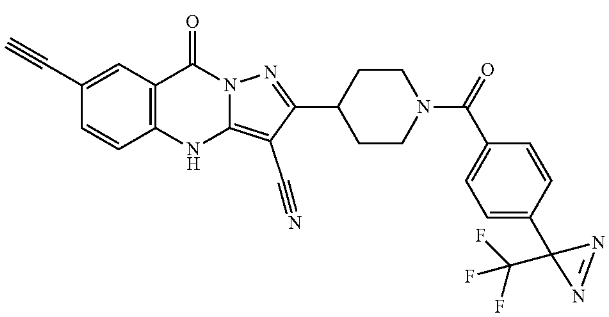 [SMILES: C#Cc1ccc2[nH]c3c(C#N)c(C4CCN(C(=O)c5ccc(C6(C(F)(F)F)N=N6)cc5)CC4)nn3c(=O)c2c1] | 9 | | | |
| 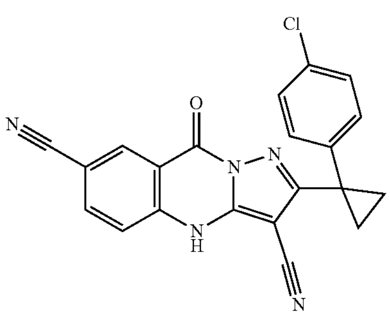 [SMILES: N#Cc1ccc2[nH]c3c(C#N)c(C4(c5ccc(Cl)cc5)CC4)nn3c(=O)c2c1] | 10 | 70.1 | 10 | |
| 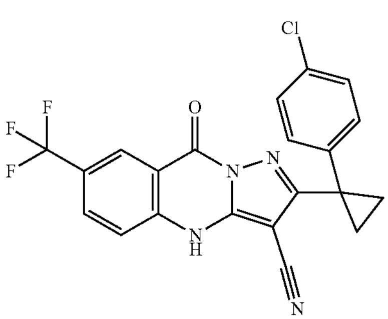 [SMILES: N#Cc1c(C2(c3ccc(Cl)cc3)CC2)nn2c(=O)c3cc(C(F)(F)F)ccc3[nH]c12] | 11 | 0.73 | 17.7 | −4.1 |

TABLE 2-continued
| Structure | Example # | Shh-light IC50, μM | SHH-light % residual @ 2 μM | SHH-light % residual @ 20 μM |
|---|---|---|---|---|
| 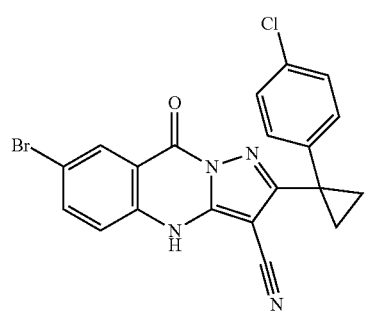 | 12 | 0.29 | −3.1 | −1.9 |
| 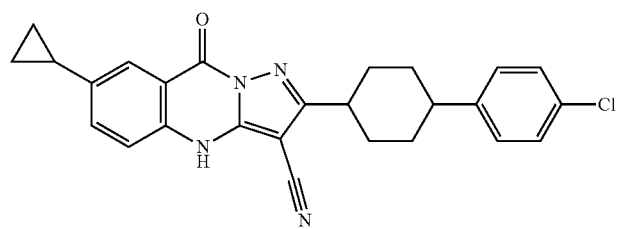 [SMILES: N#Cc1c(C2CCC(c3ccc(Cl)cc3)CC2)nn2c(=O)c3cc(C4CC4)ccc3[nH]c12] | 13 | 0.34 | −3.1 | −3.6 |
| 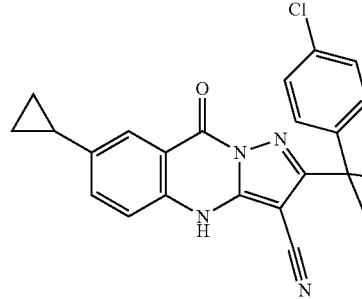 | 14 | 0.47 | −2.3 | −1.8 |
| 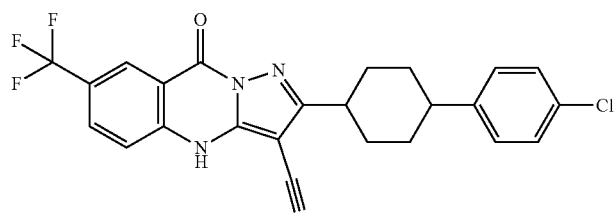 | 15 | 0.32 | −3.1 | −4 |
| 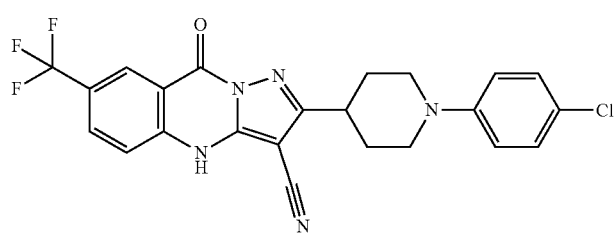 | 16 | 33.7 | −4.1 | |

TABLE 2-continued

| Structure | Example # | Shh-light IC50, μM | SHH-light % residual @ 2 μM | SHH-light % residual @ 20 μM |
|---|---|---|---|---|
| 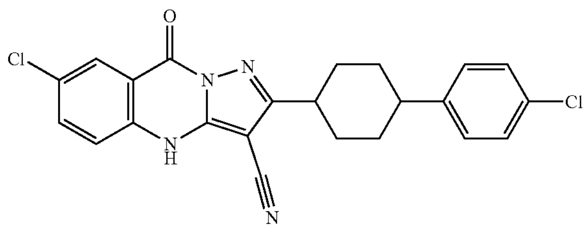 [SMILES: N#Cc1c(C2CCC(c3ccc(Cl)cc3)CC2)nn2c(=O)c3cc(Cl)ccc3[nH]c12] | 17 | 0.6 | −2.3 | −3.9 |
| 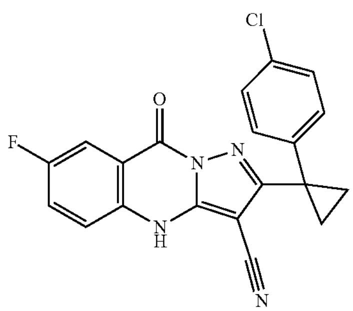 [SMILES: N#Cc1c(C2(c3ccc(Cl)cc3)CC2)nn2c(=O)c3cc(F)ccc3[nH]c12] | 19 | 1.6 | 1.4 | −0.4 |
| 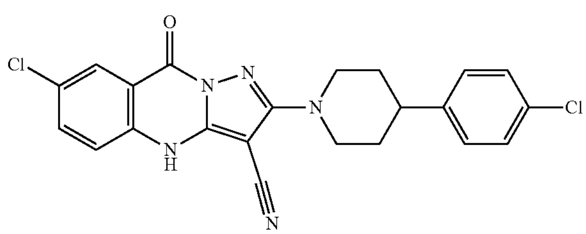 [SMILES: N#Cc1c(N2CCC(c3ccc(Cl)cc3)CC2)nn2c(=O)c3cc(Cl)ccc3[nH]c12] | 20 | 0.33 | −2.5 | −3.1 |
| 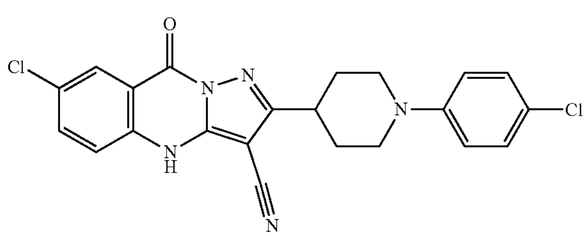 [SMILES: N#Cc1c(C2CCN(c3ccc(Cl)cc3)CC2)nn2c(=O)c3cc(Cl)ccc3[nH]c12] | 21 | | −2 | −2.6 |
| 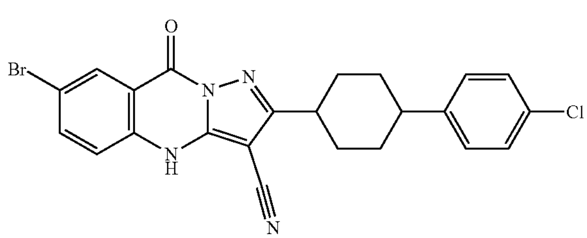 | 22 | 0.67 | −2.9 | −2.8 |

TABLE 2-continued

| Structure | Example # | Shh-light IC50, μM | SHH-light % residual @ 2 μM | SHH-light % residual @ 20 μM |
|---|---|---|---|---|
| 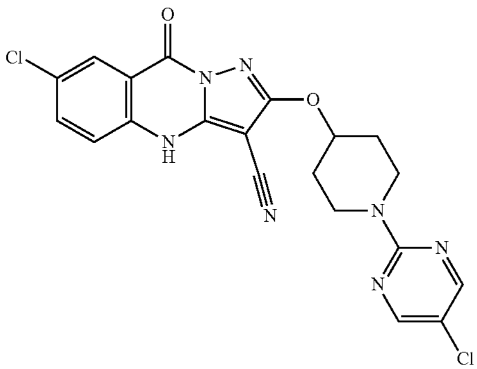 [SMILES: N#Cc1c(OC2CCN(c3ncc(Cl)cn3)CC2)nn2c(=O)c3cc(Cl)ccc3[nH]c12] | 23 | | 8.2 | −2.9 |
| 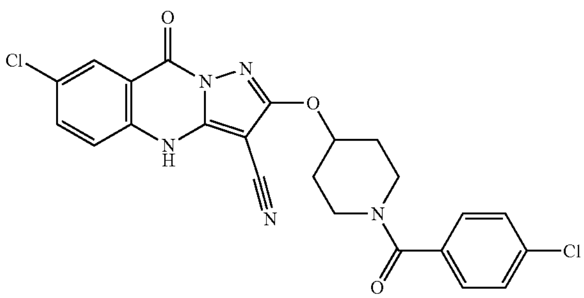 [SMILES: N#Cc1c(OC2CCN(C(=O)c3ccc(Cl)cc3)CC2)nn2c(=O)c3cc(Cl)ccc3[nH]c12] | 24 | | 72.4 | 1.6 |
| 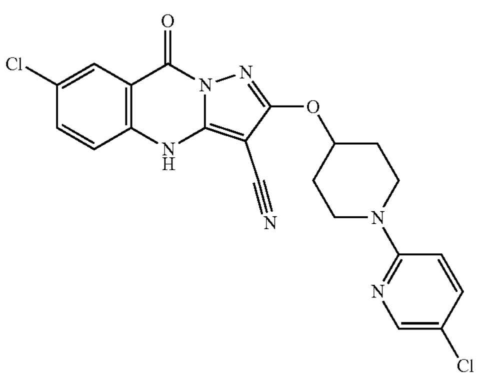 [SMILES: N#Cc1c(OC2CCN(c3ccc(Cl)cn3)CC2)nn2c(=O)c3cc(Cl)ccc3[nH]c12] | 25 | | 41.7 | −3.8 |
| 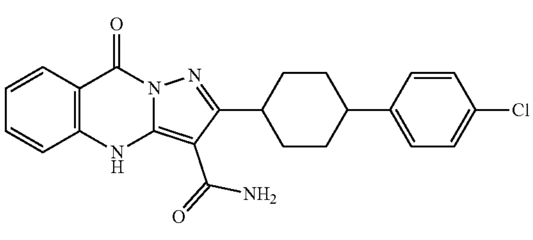 [SMILES: NC(=O)c1c(C2CCC(c3ccc(Cl)cc3)CC2)nn2c(=O)c3ccccc3[nH]c12] | 26 | | 68.8 | −4.5 |
| 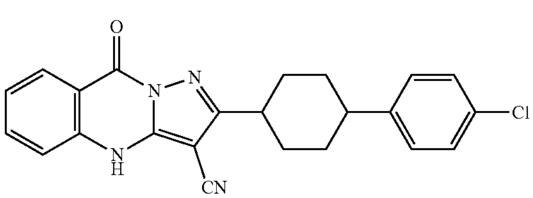 [SMILES: N#Cc1c(C2CCC(c3ccc(Cl)cc3)CC2)nn2c(=O)c3ccccc3[nH]c12] | 27 | 0.6 | 27.3 | −1.5 |

TABLE 2-continued

| Structure | Example # | Shh-light IC50, μM | SHH-light % residual @ 2 μM | SHH-light % residual @ 20 μM |
|---|---|---|---|---|
| 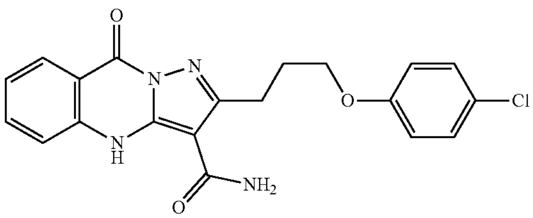 [SMILES: NC(=O)c1c(CCCOc2ccc(Cl)cc2)nn2c(=O)c3ccccc3[nH]c12] | 28 | | 68.9 | 40.3 |
| 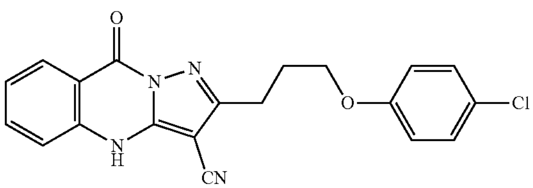 [SMILES: N#Cc1c(CCCOc2ccc(Cl)cc2)nn2c(=O)c3ccccc3[nH]c12] | 29 | 0.68 | 33.5 | 3.8 |
| 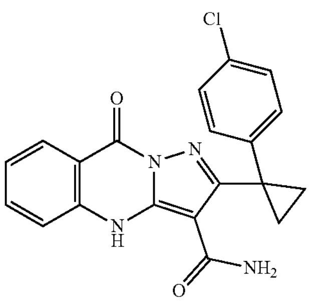 [SMILES: NC(=O)c1c(C2(c3ccc(Cl)cc3)CC2)nn2c(=O)c3ccccc3[nH]c12] | 30 | | 100.8 | 22.1 |
| 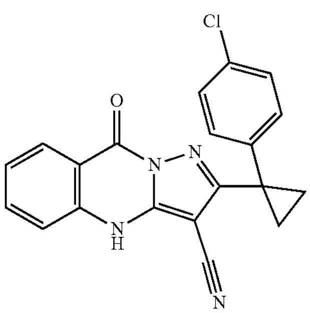 [SMILES: N#Cc1c(C2(c3ccc(Cl)cc3)CC2)nn2c(=O)c3ccccc3[nH]c12] | 31 | 0.66 | 30.4 | −1.6 |
| 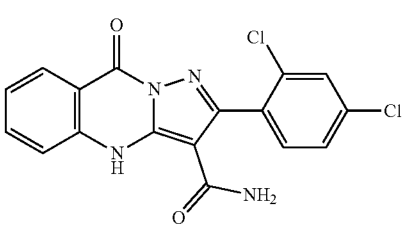 [SMILES: NC(=O)c1c(-c2ccc(Cl)cc2Cl)nn2c(=O)c3ccccc3[nH]c12] | 32 | | | 57.5 |
| 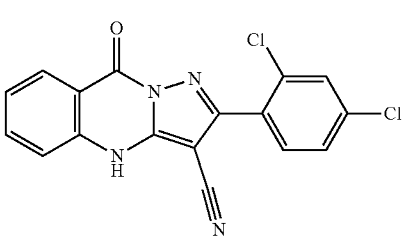 [SMILES: N#Cc1c(-c2ccc(Cl)cc2Cl)nn2c(=O)c3ccccc3[nH]c12] | 33 | 2 | | −3.6 |

TABLE 2-continued
| Structure | Example # | Shh-light IC50, μM | SHH-light % residual @ 2 μM | SHH-light % residual @ 20 μM |
|---|---|---|---|---|
| 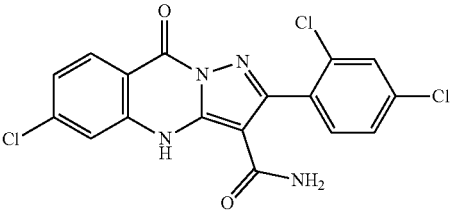 [SMILES: NC(=O)c1c(-c2ccc(Cl)cc2Cl)nn2c(=O)c3ccc(Cl)cc3[nH]c12] | 34 | 3.6 | | −3.4 |
| 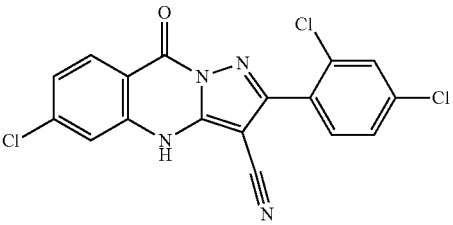 [SMILES: N#Cc1c(-c2ccc(Cl)cc2Cl)nn2c(=O)c3ccc(Cl)cc3[nH]c12] | 35 | 2.1 | | |
| 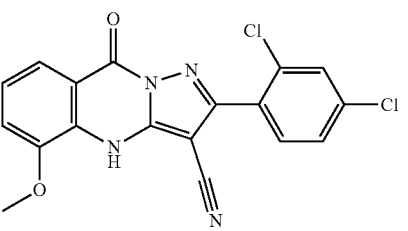 [SMILES: COc1cccc2c(=O)n3nc(-c4ccc(Cl)cc4Cl)c(C#N)c3[nH]c12] | 36 | 10 | | |
| 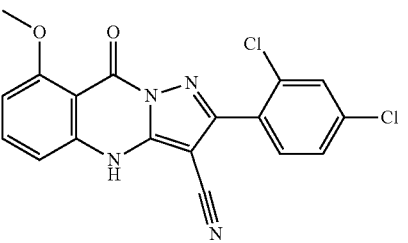 [SMILES: COc1cccc2[nH]c3c(C#N)c(-c4ccc(Cl)cc4Cl)nn3c(=O)c12] | 37 | 100 | | 18 |
| 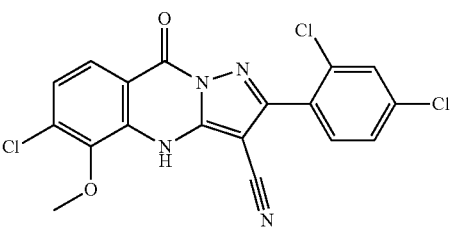 [SMILES: COc1c(Cl)ccc2c(=O)n3nc(-c4ccc(Cl)cc4Cl)c(C#N)c3[nH]c12] | 38 | 2 | 74 | 19 |
| 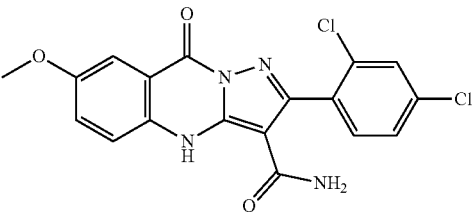 [SMILES: COc1ccc2[nH]c3c(C(N)=O)c(-c4ccc(Cl)cc4Cl)nn3c(=O)c2c1] | 39 | 13 | | 121 |

TABLE 2-continued

| Structure | Example # | Shh-light IC50, μM | SHH-light % residual @ 2 μM | SHH-light % residual @ 20 μM |
|---|---|---|---|---|
| 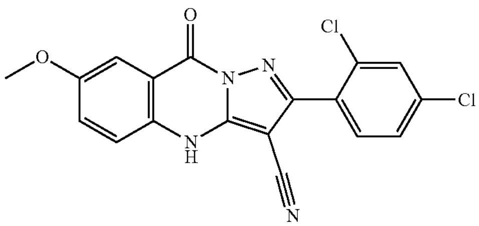 [SMILES: COc1ccc2[nH]c3c(C#N)c(-c4ccc(Cl)cc4Cl)nn3c(=O)c2c1] | 40 | 0.594 | 37 | 14 |
| 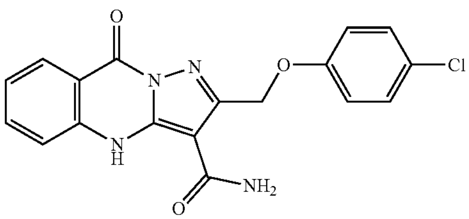 [SMILES: NC(=O)c1c(COc2ccc(Cl)cc2)nn2c(=O)c3ccccc3[nH]c12] | 41 | | 73.7 | |
| 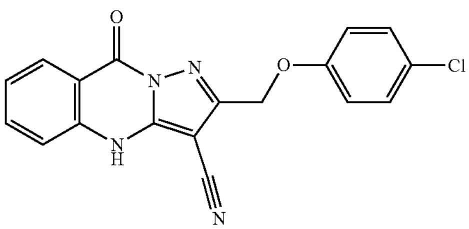 [SMILES: N#Cc1c(COc2ccc(Cl)cc2)nn2c(=O)c3ccccc3[nH]c12] | 42 | | 105.4 | 4.5 |
| 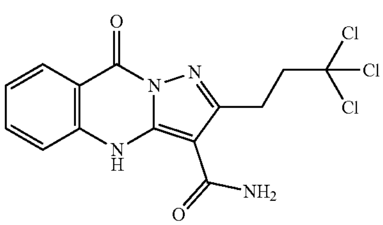 [SMILES: NC(=O)c1c(CCC(Cl)(Cl)Cl)nn2c(=O)c3ccccc3[nH]c12] | 43 | | 65 | 15.4 |
| 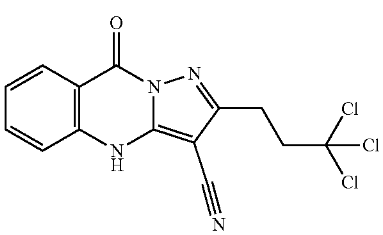 [SMILES: N#Cc1c(CCC(Cl)(Cl)Cl)nn2c(=O)c3ccccc3[nH]c12] | 44 | | 45.8 | 3.4 |
| 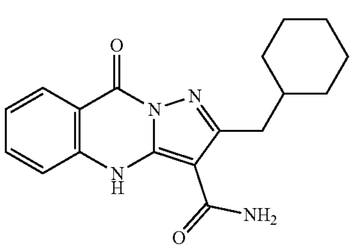 [SMILES: NC(=O)c1c(CC2CCCCC2)nn2c(=O)c3ccccc3[nH]c12] | 45 | | 82.4 | 4 |

TABLE 2-continued

| Structure | Example # | Shh-light IC50, μM | SHH-light % residual @ 2 μM | SHH-light % residual @ 20 μM |
|---|---|---|---|---|
| 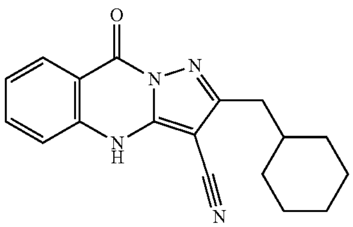 [SMILES: N#Cc1c(CC2CCCCC2)nn2c(=O)c3ccccc3[nH]c12] | 46 | | 67.1 | 5 |
| 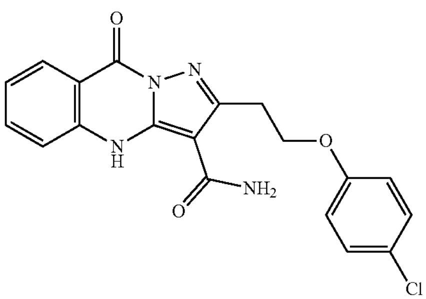 [SMILES: NC(=O)c1c(CCOc2ccc(Cl)cc2)nn2c(=O)c3ccccc3[nH]c12] | 47 | | 54.7 | 11 |
| 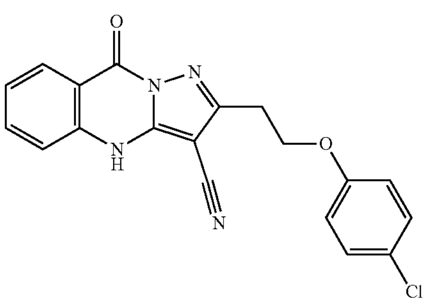 [SMILES: N#Cc1c(CCOc2ccc(Cl)cc2)nn2c(=O)c3ccccc3[nH]c12] | 48 | | 75.5 | 10.9 |
| 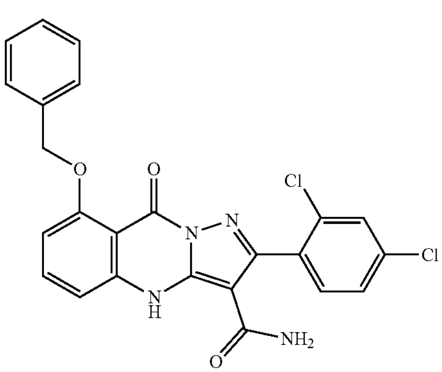 [SMILES: NC(=O)c1c(-c2ccc(Cl)cc2Cl)nn2c(=O)c3c(OCc4ccccc4)cccc3[nH]c12] | 49 | | 78.3 | 10.8 |

TABLE 2-continued

| Structure | Example # | Shh-light IC50, μM | SHH-light % residual @ 2 μM | SHH-light % residual @ 20 μM |
|---|---|---|---|---|
| 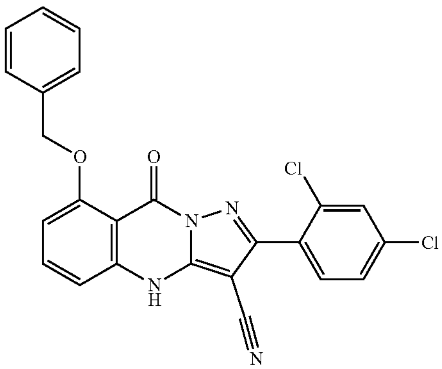 [SMILES: N#Cc1c(-c2ccc(Cl)cc2Cl)nn2c(=O)c3c(OCc4ccccc4)cccc3[nH]c12] | 50 | | 75.8 | |
| 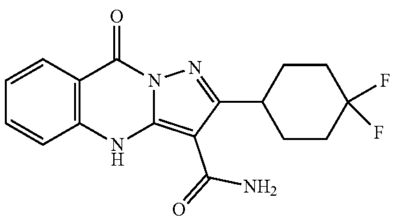 [SMILES: NC(=O)c1c(C2CCC(F)(F)CC2)nn2c(=O)c3ccccc3[nH]c12] | 51 | | 92.4 | 103.2 |
| 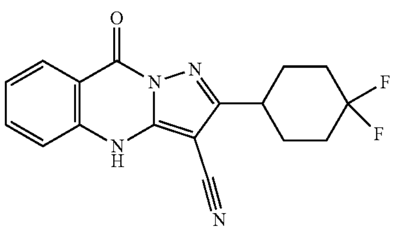 [SMILES: N#Cc1c(C2CCC(F)(F)CC2)nn2c(=O)c3ccccc3[nH]c12] | 52 | | 110.4 | 76.9 |
| 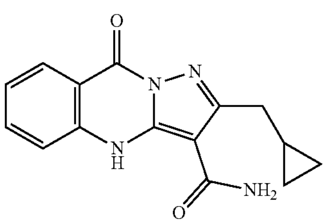 [SMILES: NC(=O)c1c(CC2CC2)nn2c(=O)c3ccccc3[nH]c12] | 53 | | 75.2 | 122.7 |
| 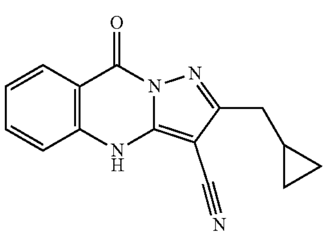 [SMILES: N#Cc1c(CC2CC2)nn2c(=O)c3ccccc3[nH]c12] | 54 | | 81.7 | |
| 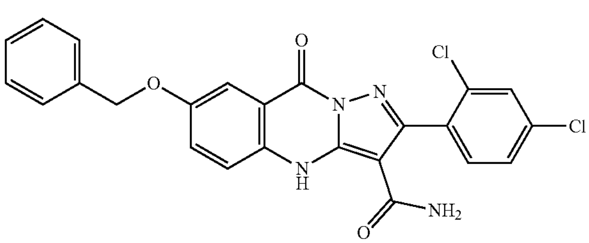 [SMILES: NC(=O)c1c(-c2ccc(Cl)cc2Cl)nn2c(=O)c3cc(OCc4ccccc4)ccc3[nH]c12] | 55 | | 62.8 | |

TABLE 2-continued
| Structure | Example # | Shh-light IC50, μM | SHH-light % residual @ 2 μM | SHH-light % residual @ 20 μM |
|---|---|---|---|---|
| 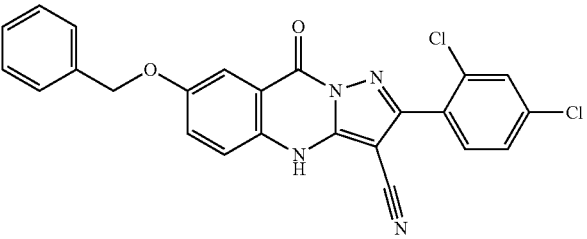 [SMILES: N#Cc1c(-c2ccc(Cl)cc2Cl)nn2c(=O)c3cc(OCc4ccccc4)ccc3[nH]c12] | 56 | | 49.6 | |
| 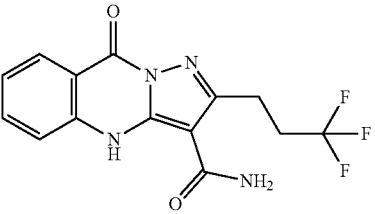 [SMILES: NC(=O)c1c(CCC(F)(F)F)nn2c(=O)c3ccccc3[nH]c12] | 57 | | 67.9 | |
| 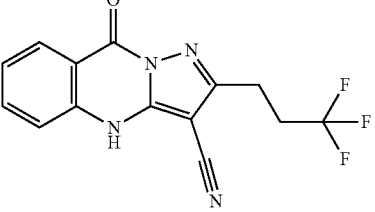 | 58 | | 55.5 | 35.1 |
| 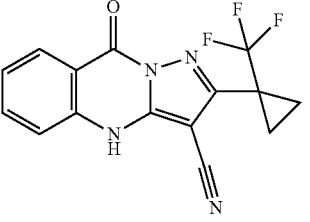 [SMILES: N#Cc1c(C2(C(F)(F)F)CC2)nn2c(=O)c3ccccc3[nH]c12] | 59 | | 89.3 | 45.1 |
| 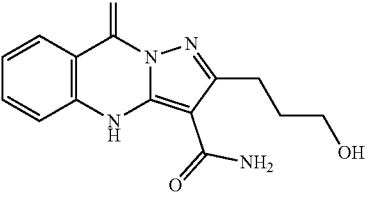 | 60 | | 78.1 | 99 |
| 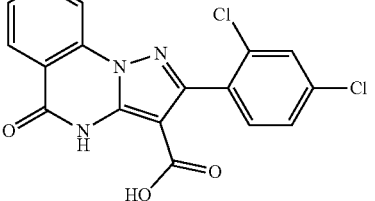 | 61 | | 66.7 | |

TABLE 2-continued

| Structure | Example # | Shh-light IC50, μM | SHH-light % residual @ 2 μM | SHH-light % residual @ 20 μM |
|---|---|---|---|---|
| 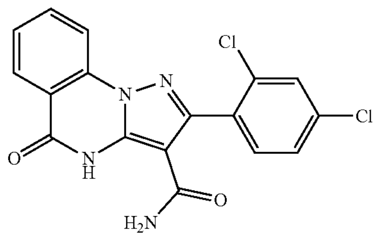 [SMILES: NC(=O)c1c(-c2ccc(Cl)cc2Cl)nn2c1[nH]c(=O)c1ccccc12] | 62 | | | 42.1 |
| 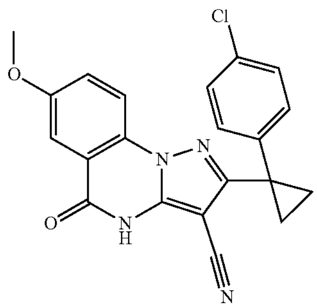 [SMILES: COc1ccc2c(c1)c(=O)[nH]c1c(C#N)c(C3(c4ccc(Cl)cc4)CC3)nn12] | 64 | | 91.6 | 90.4 |
| 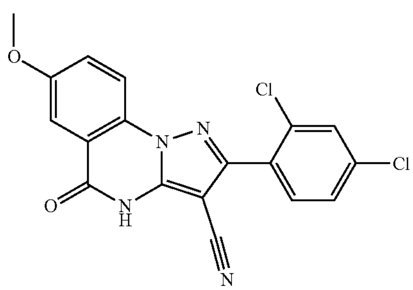 [SMILES: COc1ccc2c(c1)c(=O)[nH]c1c(C#N)c(-c3ccc(Cl)cc3Cl)nn12] | 65 | | 76.9 | −1 |
| 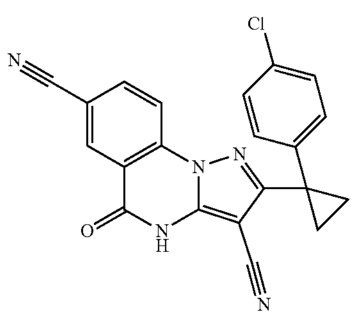 [SMILES: N#Cc1ccc2c(c1)c(=O)[nH]c1c(C#N)c(C3(c4ccc(Cl)cc4)CC3)nn12] | 66 | 1.5 | 39.6 | −3.8 |
| 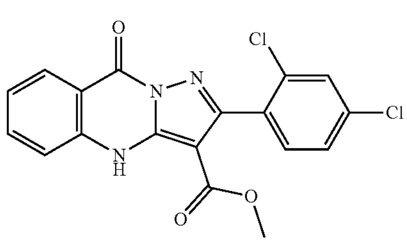 [SMILES: COC(=O)c1c(-c2ccc(Cl)cc2Cl)nn2c(=O)c3ccccc3[nH]c12] | 67 | | | 80.3 |

TABLE 2-continued
| Structure | Example # | Shh-light IC50, μM | SHH-light % residual @ 2 μM | SHH-light % residual @ 20 μM |
|---|---|---|---|---|
| 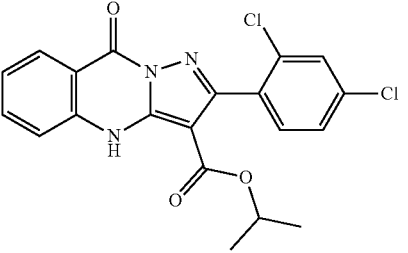 [SMILES: CC(C)OC(=O)c1c(-c2ccc(Cl)cc2Cl)nn2c(=O)c3ccccc3[nH]c12] | 68 | | 90.5 | 109.7 |
| 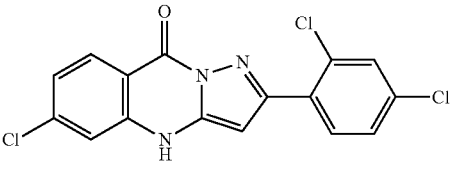 [SMILES: O=c1c2ccc(Cl)cc2[nH]c2cc(-c3ccc(Cl)cc3Cl)nn12] | 69 | | 75 | 65.4 |
| 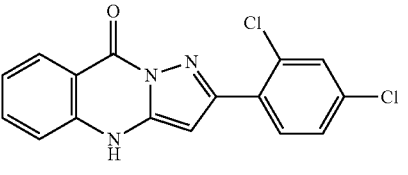 [SMILES: O=c1c2ccccc2[nH]c2cc(-c3ccc(Cl)cc3Cl)nn12] | 70 | | 109.3 | 112.9 |
| 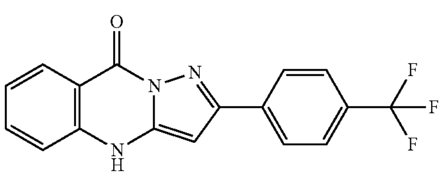 [SMILES: O=c1c2ccccc2[nH]c2cc(-c3ccc(C(F)(F)F)cc3)nn12] | 71 | | 107.6 | 115 |
| 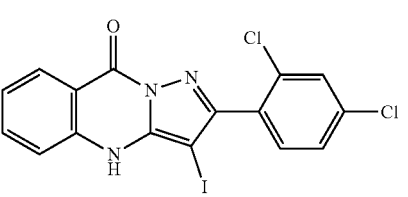 | 72 | | 122.2 | 20.1 |
| 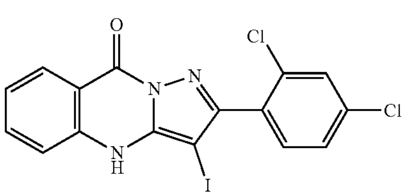 [SMILES: O=c1c2ccccc2[nH]c2c(I)c(-c3ccc(Cl)cc3Cl)nn12] | 73 | | 99.1 | 34.6 |

The invention claimed is:
1. A compound of formula

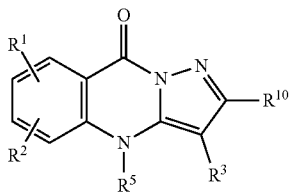

wherein
$R^1$ and $R^2$ are independently chosen from hydrogen, halogen, $(C_1\text{-}C_{10})$hydrocarbon, —O—$(C_1\text{-}C_{10})$hydrocarbyl, fluoro$(C_1\text{-}C_6)$alkyl, —O$(C_1\text{-}C_6)$fluoroalkyl, —CN, and nitro;
$R^3$ is chosen from hydrogen, cyano, $(C_1\text{-}C_6)$alkoxycarbonyl, aminocarbonyl, carboxy, $(C_1\text{-}C_6)$alkylaminocarbonyl, $(C_1\text{-}C_6)$dialkylaminocarbonyl, halo, amino$(C_1\text{-}C_6)$alkyl, $(C_1\text{-}C_6)$alkylamino$(C_1\text{-}C_6)$alkyl, $(C_1\text{-}C_6)$dialkylamino$(C_1\text{-}C_6)$alkyl, and nitro;
$R^5$ is chosen from hydrogen and methyl;
$R^{10}$ is:
(a)

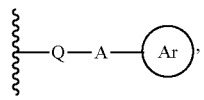

in which
Ar is chosen from substituted aryl, optionally substituted heteroaryl, said aryl or heteroaryl substituted or optionally substituted, respectively, with one, two or three substituents chosen independently from, halogen, $(C_1\text{-}C_{10})$hydrocarbon, —O—$(C_1\text{-}C_6)$alkyl, fluoro$(C_1\text{-}C_6)$alkyl, —O—$(C_1\text{-}C_6)$fluoroalkyl, hydroxy, methylenedioxy, ethylenedioxy, —CN, nitro, —S—$(C_1\text{-}C_6)$alkyl, $(C_1\text{-}C_6)$alkoxycarbonyl, $(C_1\text{-}C_6)$acyl, amino, $(C_1\text{-}C_6)$alkylamino, di$(C_1\text{-}C_6)$alkylamino, $(C_1\text{-}C_6)$acylamino, and

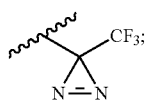

Q is a direct bond or a linker chosen from —O—, —$(C_1\text{-}C_{10})$hydrocarbyl-, —$(C_1\text{-}C_{10})$oxaalkyl, fluoro$(C_1\text{-}C_{10})$alkyl, —O—$(C_1\text{-}C_6)$fluoroalkyl,

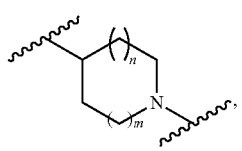

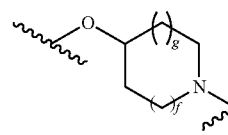 and

-continued

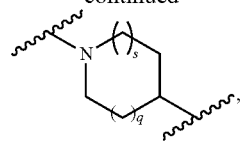

wherein the left wavy line indicates the point of attachment to the pyrazole ring and the right wavy line indicates the point of attachment to A;
A is a direct bond or a linker chosen from:
—$CR^6R^7$— and —C(═O)—; and
$R^6$ and $R^7$ are independently selected from methyl and hydrogen;
or
(b) $R^{10}$ is chosen from $(C_2\text{-}C_{10})$ hydrocarbyl, $(C_1\text{-}C_{10})$halohydrocarbyl, $(C_1\text{-}C_6)$hydroxyalkyl, and

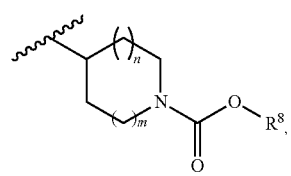

wherein the left wavy line indicates the point of attachment to the pyrazole ring and $R^8$ is $(C_1\text{-}C_{10})$ hydrocarbyl;
n is 0 or 1;
m is 0, 1, or 2;
p is 0 or 1;
t is 0, 1, or 2;
g is 0 or 1;
f is 0, 1, or 2;
s is 0 or 1; and
q is 0, 1, or 2.
2. A compound according to claim 1 wherein $R^{10}$ is chosen from $(C_1\text{-}C_{10})$ hydrocarbyl, and $(C_1\text{-}C_{10})$halohydrocarbyl.
3. A compound according to claim 1 wherein $R^{10}$ is

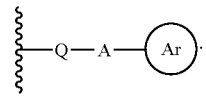

4. A compound according to claim 3, wherein A is a direct bond between Q and Ar.
5. A compound according to claim 3, wherein both A and Q are a single direct bond between the pyrazole ring and Ar.
6. A compound according to claim 3 wherein:
$R^1$ and $R^2$ are independently chosen from hydrogen, halogen, methoxy, benzyloxy, trifluoromethyl, cyclopropyl, ethynyl, —CN, and nitro;
$R^3$ is chosen from hydrogen, cyano, COO$(C_1\text{-}C_3)$alkyl, CONH$_2$, and dimethylaminomethyl;
Ar is monocyclic aryl or heteroaryl, optionally substituted with one, two or three substituents chosen independently from, halogen, fluoro$(C_1\text{-}C_6)$alkyl, —O—$(C_1\text{-}C_6)$fluoroalkyl; and
Q is a direct bond or a linker chosen from —O—, —$(C_1\text{-}C_{10})$hydrocarbyl-, —$(C_1\text{-}C_{10})$oxaalkyl, fluoro$(C_1\text{-}C_{10})$alkyl, and —O—$(C_1\text{-}C_6)$fluoroalkyl.

7. A compound according to claim 6 wherein $R^{10}$ is

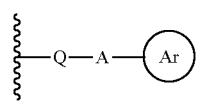

and A is a direct bond, said compound having the formula

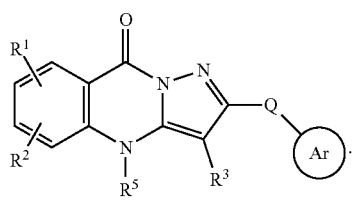

8. A compound according to claim 6 wherein Ar is chosen from phenyl, naphthyl, thiophenyl, furanyl, pyrrolyl, and pyridinyl, any of which may be optionally substituted with from one to three substituents independently chosen from halogen, $(C_1-C_{10})$hydrocarbyl, fluoro$(C_1-C_6)$alkyl, —O—$(C_1-C_6)$fluoroalkyl, —CN, nitro, $(C_1-C_6)$alkoxycarbonyl and $(C_1-C_6)$acyl.

9. A compound according to claim 1 wherein $R^2$ is H and $R^1$ is chosen from H, halogen, trifluoromethyl, trifluoromethoxy and methyl.

10. A compound according to claim 8 wherein $R^3$ is CN; $R^2$ and $R^5$ are H; and $R^1$ is chosen from H and halogen.

11. A compound according to claim 7 wherein Ar is chlorophenyl; $R^3$ is CN; $R^2$, $R^5$ is H; and Q is $(C_3-C_6)$hydrocarbyl or —$(CH_2)_3O$—.

12. A compound according to claim 1 wherein Q is a direct bond or $(C_3-C_6)$cycloalkyl.

13. A compound according to claim 6 wherein Q is cyclopropyl, cyclobutyl, cyclopentyl or cyclohexyl.

14. A compound according to claim 13 wherein $R^1$ is chosen from H, halogen, and trifluoromethyl; $R^2$ is H; $R^3$ is chosen from hydrogen and cyano; and $R^5$ is chosen from hydrogen and methyl.

15. A method of inhibiting intraflagellar transport in a cell comprising bringing said cell into contact with a compound of claim 1.

16. A method according to claim 15 wherein said method of inhibiting is an in vitro method.

17. A method according to claim 15 wherein said method of inhibiting is an in vivo method.

18. A method of inhibiting the growth of a solid tumor comprising bringing said solid tumor into contact with a compound of claim 1.

19. A method according to claim 18 wherein said solid tumor is chosen from basal cell carcinoma, glioblastoma and medulloblastoma.

20. A compound of formula

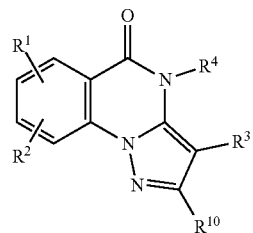

wherein
  $R^1$ and $R^2$ are independently chosen from hydrogen, fluoro, chloro, bromo, $(C_1-C_{10})$hydrocarbyl, —O—$(C_1-C_{10})$hydrocarbyl, fluoro$(C_1-C_6)$alkyl, —O$(C_1-C_6)$fluoroalkyl, —CN, and nitro;
  $R^3$ is chosen from hydrogen, cyano, $(C_1-C_6)$alkoxycarbonyl, aminocarbonyl, carboxy, $(C_1-C_6)$alkylaminocarbonyl, $(C_1-C_6)$dialkylaminocarbonyl, halo, amino$(C_1-C_6)$alkyl, $(C_1-C_6)$alkylamino$(C_1-C_6)$alkyl, $(C_1-C_6)$dialkylamino$(C_1-C_6)$alkyl, and nitro;
  $R^4$ is chosen from hydrogen and methyl;
  $R^{10}$ is:
    (a)

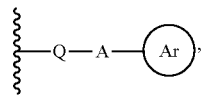

in which
  Ar is chosen from optionally substituted aryl, optionally substituted heteroaryl, said aryl or heteroaryl optionally substituted with one, two or three substituents chosen independently from, halogen, $(C_1-C_{10})$hydrocarbyl, —O—$(C_1-C_6)$alkyl, fluoro $(C_1-C_6)$alkyl, —O—$(C_1-C_6)$fluoroalkyl, hydroxy, methylenedioxy, ethylenedioxy, —CN, nitro, —S—$(C_1-C_6)$alkyl, $(C_1-C_6)$alkoxycarbonyl, $(C_1-C_6)$acyl, amino, $(C_1-C_6)$alkylamino, di$(C_1-C_6)$alkylamino, $(C_1-C_6)$acylamino, and

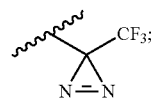

Q is a linker chosen from O—, —$(C_1-C_{10})$hydrocarbyl-, —$(C_1-C_{10})$oxaalkyl, fluoro$(C_1-C_{10})$alkyl, —O—$(C_1-C_6)$fluoroalkyl,

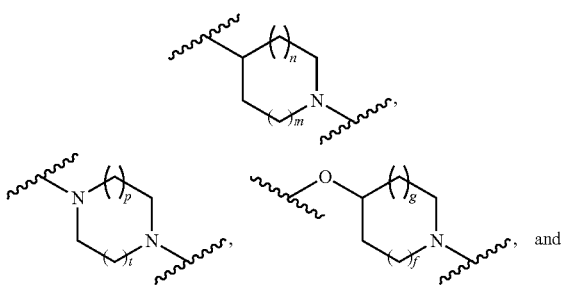

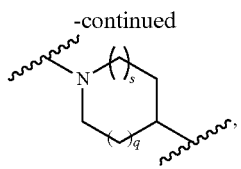

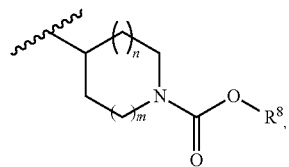

wherein the left wavy line indicates the point of attachment to the pyrazole ring and the right wavy line indicates the point of attachment to A;

A is a direct bond or a linker chosen from: —$CR^6R^7$— and —C(=O)—; and $R^6$ and $R^7$ are independently selected from methyl and hydrogen;

or (b) $R^{10}$ is chosen from $(C_8-C_{10})$ hydrocarbyl, $(C_1-C_{10})$ halohydrocarbyl, $(C_2-C_6)$hydroxyalkyl, and wherein the left wavy line indicates the point of attachment to the pyrazole ring and $R^8$ is $(C_1-C_{10})$hydrocarbyl;

n is 0 or 1;
m is 0, 1, or 2;
p is 0 or 1;
t is 0, 1, or 2;
g is 0 or 1;
f is 0, 1, or 2;
s is 0 or 1; and
q is 0, 1, or 2.

* * * * *